United States Patent
Chaplin et al.

(10) Patent No.: US 11,279,745 B2
(45) Date of Patent: Mar. 22, 2022

(54) TOLEROGENIC DNA VACCINE

(71) Applicant: Novo Nordisk A/S, Bagsvaerd (DK)

(72) Inventors: Jay Chaplin, Mountlake Terrace, WA (US); Michael Wijaranakula, Seattle, WA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/395,865

(22) Filed: Apr. 26, 2019

(65) Prior Publication Data

US 2020/0339650 A1   Oct. 29, 2020

(51) Int. Cl.

| C07K 14/62 | (2006.01) |
|---|---|
| C12N 15/85 | (2006.01) |
| A61K 9/00 | (2006.01) |
| A61P 3/10 | (2006.01) |
| C07K 14/54 | (2006.01) |
| C07K 14/495 | (2006.01) |

(52) U.S. Cl.
CPC ............ *C07K 14/62* (2013.01); *A61K 9/0019* (2013.01); *A61P 3/10* (2018.01); *C07K 14/495* (2013.01); *C07K 14/5428* (2013.01); *C12N 15/85* (2013.01)

(58) Field of Classification Search
None
See application file for complete search history.

(56) References Cited

U.S. PATENT DOCUMENTS

| 6,083,919 | A | 7/2000 | Johnson et al. | |
|---|---|---|---|---|
| D459,798 | S | 7/2002 | Desesquelle et al. | |
| 7,544,669 | B2 | 6/2009 | Fontoura et al. | |
| 9,339,500 | B2 | 5/2016 | Wennogle | |
| 9,550,998 | B2 | 1/2017 | Williams | |
| D835,258 | S | 12/2018 | Parikh et al. | |
| 10,487,334 | B2 | 11/2019 | Audonnet et al. | |
| 2002/0107210 | A1 | 8/2002 | Herrath | |
| 2002/0193330 | A1 | 12/2002 | Hone et al. | |
| 2003/0148983 | A1* | 8/2003 | Fontoura | A61K 38/2026 514/44 R |
| 2004/0110295 | A1* | 6/2004 | Punnonen | C07K 14/005 435/455 |
| 2004/0234984 | A1 | 11/2004 | Isaksson et al. | |
| 2005/0026189 | A1 | 2/2005 | Wang et al. | |
| 2005/0147621 | A1 | 7/2005 | Higgins et al. | |
| 2005/0261215 | A1 | 11/2005 | Garren et al. | |
| 2006/0234964 | A1* | 10/2006 | Strober | A01K 67/027 514/44 R |
| 2009/0016968 | A1* | 1/2009 | Wang | A61K 39/0008 424/45 |
| 2009/0042301 | A1 | 2/2009 | Owttrim et al. | |
| 2010/0160415 | A1 | 6/2010 | Solvason et al. | |
| 2011/0034543 | A1 | 2/2011 | Steinman et al. | |
| 2014/0234423 | A1 | 8/2014 | Sands et al. | |
| 2019/0241898 | A1 | 8/2019 | Chaplin | |
| 2020/0339650 | A1 | 10/2020 | Chaplin et al. | |

FOREIGN PATENT DOCUMENTS

| JP | 2012527249 | A | 11/2012 | |
|---|---|---|---|---|
| JP | 2014526472 | A | 10/2014 | |
| RU | 2228198 | | 5/2004 | |
| WO | 9824469 | A1 | 6/1998 | |
| WO | 2005089101 | A2 | 9/2005 | |
| WO | 2007016764 | A1 | 2/2007 | |
| WO | 07147011 | A2 | 12/2007 | |
| WO | 11091138 | A1 | 7/2011 | |
| WO | 12041867 | A2 | 4/2012 | |
| WO | 2012062697 | A1 | 5/2012 | |
| WO | 2013036914 | | 3/2013 | |
| WO | 2014144965 | | 9/2014 | |
| WO | WO-2016057986 | A1 * | 4/2016 | ......... A61K 39/0008 |
| WO | 2016162385 | A1 | 10/2016 | |
| WO | 2017097383 | A1 | 6/2017 | |

OTHER PUBLICATIONS

Chinnasamy et al. Multicistronic Lentiviral Vectors Containing the FMDV 2A Cleavage Factor Demonstrate Robust Expression of Encoded Genes at Limiting MOI. Virology Journal, 2006. 3:14, 6 pages.*
Bot et al., Plasmid Vaccination with Insulin B Chain Prevents; Autoimmune Diabetes in Nonobese Diabetic Mice, The Journal of Immunology, 2001, vol. 167, pp. 2950-2955.
Harrison C et al., Vaccination against self to prevent autoimmune; disease: the type 1 diabetes model, Immunology and Cell Biology, 2008, vol. 86, pp. 139-145.
Johnson C. et al., Genetic vaccination for re-establishing T-cell tolerance; in type 1 diabetes, Human Vaccines, 2011, vol. 7, No. 1, pp. 27-36.
Prud'Homme et al., DNA vaccines that induce regulatory T cells and protect against autoimmune diabetes, Gene Ther Mol Biol, 2005, vol. 9, pp. 183-192.
Prud'Homme et al., Plasmid-based gene therapy of diabetes mellitus, Gene Therapy, 2007, vol. 14, pp. 553-564.
Roep et al., Plasmid-Encoded Proinsulin Preserves C-Peptide WhileSpecifically Reducing Proinsulin-Specific CD8+ T Cells in Type 1 Diabetes, www.ScienceTranslationalMedicine.org, 2013, vol. 5, No. 191, pp. 191ra82.
Sarikonda et al., "Transient B-Cell Depletion with Anti-CD20 in Combination with Proinsulin DNA Vaccine or Oral Insulin: Immunologic Effects and Efficacy in NOD Mice," PLoS One, 2013, vol. 8, No. 2, p. e54712.
Solvason et al., Improved Efficacy of a Tolerizing DNA Vaccine for Reversal; of Hyperglycemia through Enhancement of Gene Expression; and Localization to Intracellular Sites, The Journal of Immunology, 2008, vol. 181, pp. 8298-8307.

(Continued)

*Primary Examiner* — James D Schultz
*Assistant Examiner* — Kimberly A Aron
(74) *Attorney, Agent, or Firm* — Jianjie Hu

(57) ABSTRACT

The present invention relates to plasmids useful for prevention and/or delay of e.g. type 1 diabetes.

16 Claims, 4 Drawing Sheets

Specification includes a Sequence Listing.

(56) References Cited

OTHER PUBLICATIONS

Coppieters et al., "Trials in Type 1 Diabetes: Antigen-Specific Therapies," Clinical Immunology, 2013, vol. 149, No. 3, pp. 345-355.

Gottlieb et al., "Clinical Optimization of Antigen Specific Modulation of Type 1 Diabetes with the Plasmid DNA Platform," Clinical Immunology, 2013, vol. 149, No. 3, pp. 297-306.

Torres-Aguilar et al., "IL-10/TGF-I-Treated Dendritic Cells Pulsed with Insulin, Specifically Reduce the Response to Insulin of CD4+ Effector/Memory T Cells from Type 1 Diabetic Individuals," Journal of Clinical Immunology, 2010, vol. 30, No. 5, pp. 659-668.

Yu et al., Identification of Candidate Tolerogenic CD8 + T Cell Epitopes for Therapy of Type 1 Diabetes in the NOD Mouse Model, Journal of Diabetes Research, 2016, vol. 2016, pp. 1-12.

Croitoru et al., "Generation and characterization of functional mutants in the translation initiation factor IF1 of *Escherichia coli*," Eur J Biochem., 2004, vol. 271, No. 3, pp. 534-544.

Goransson et al., "Regulatory genes in the thermoregulation Of *Escherichia coli* pili gene transcription," Genes & Development, 1989, vol. 3, pp. 123-130.

Goransson et al., "Transcriptional silencing and thermoregulation of gene expression in *Escherichia coli*," Nature, 1990, vol. 34, p. 682-685.

Hägg et al., "A host/plasmid system that is not dependent on antibiotics and antibiotic resistance genes for stable plasmid maintenance in *Escherichia coli*," J Biotechnol., 2004, vol. 111, No. 1, pp. 17-30.

Johansson et al., "An RNA thermosensor controls expression of virulence genes in Listeria monocytogenes," Cell, 2002, vol. 110, No. 5, pp. 551-561.

Matsunaga et al., "Role for cis-Acting RNA Sequences in the Temperature-Dependent Expression of the Multiadhesive Lig Proteins in Leptospira Interrogans," Journal of Bacteriology, 2013, vol. 195, No. 22, pp. 5092-5101.

Sodoyer et al., "Antibiotic-Free Selection for Bio-Production: Moving Towards a New "Gold Standard,"" Apr. 4, 2012, pp. 531-538.

Waldminghaus et al., "Generation of Synthetic RNA-based Thermosensors," Biological Chemistry, 2008, vol. 389, No. 10, abstract.

Muller S. et al., "Spliceosomal peptide P140 for immunotherapy of systemic lupus erythematosus: results of an early phase II clinical trial," Arthritis & Rheumatism: Official Journal of the American College of Rheumatology, Dec. 2008, vol. 58, No. 12, pp. 3873-3883.

Lev Kisselev, Polypeptide Release Factors in Prokaryotes and Eukaryotes Same Function Different Structure, "Structure" Year 2002, vol. 10, No. (1) pp. 8-9.

Whisstock, J.C et al., Journal Title: Quaterly Reviews of Biophysics,Title: Prediction of Protein Function from Protein Sequence and Structure, 2003,vol. 36,Part: 3,pp. 307-340.

Witkowski Andrzej et al.Conversion of a beta-Ketoacyl Synthase to a Malonyl Decarboxylase by Replacementof the Active-Site Cysteine with Glutamine, Biochemistry, Year 1999, vol. 38 No. (36): pp. 11643-11650.

Loh et al., "An unstructured 5'-coding region of the prfA mRNA is required for efficient translation", Nucleic Acids Research, Nov. 3, 2011, vol. 40, No. 4, pp. 1818-1827.

\* cited by examiner

Passages 1-50.

Passages 51-100.

TOLEROGENIC DNA VACCINE

SEQUENCE LISTING

The instant application contains a Sequence Listing which has been submitted in ASCII format via EFS-Web and is hereby incorporated by reference in its entirety. Said ASCII copy, created on Apr. 24, 2019, is named 190050US01_SeqList.txt and is 55 kilobytes in size.

TECHNICAL FIELD

The present invention relates to tolerogeneic DNA immuno-therapy vaccines for reducing antigen-specific T cell reactivity.

BACKGROUND

According to traditional vaccine approaches, purified protein/antigen is injected in a person/patient/animal in order to stimulate immune responses specifically to that protein/antigen. This vaccine approach tends to impact primarily antibody production, while the T cells tend not to be significantly affected, other than to generate T cell memory of the antigen. Traditional vaccine approaches are thus not considered suitable in connection with treatment and/or prevention of T cell driven diseases such as e.g. Type 1 diabetes (T1D), as activation of T cells, especially $CD8^+$ T cells, are considered the causative agent of this disease. Experimental approaches with tolerogenic, protein-based vaccines have targeted primarily antibody producing B cells rather than disease relevant T cells.

DNA based vaccines, in contrast to protein-based vaccines, are usually plasmids encoding particular antigens—these plasmids are taken up by cells in the host's body ("transfected"). These transfected host cells then produce the antigen and process the antigen into small fragments (T-cell epitopes) for presentation to the immune system, in particular to circulating T cells. As T cells can only detect these small antigen fragments and not whole proteins, this approach preferentially leads to a modification of T cell responses, especially for $CD8^+$ T cells (or cytotoxic T cells), the key drivers of e.g. T1D pathology. Thus, DNA vaccines, rather than protein vaccines, are suitable for inducing T cell responses. While no DNA vaccines are currently available for human use, there are three stimulatory plasmid DNA vaccines licensed for veterinary use, inducing immunity to Equine Infectious Anemia Virus, West Nile Virus, and certain canine cancers.

In contrast to stimulatory DNA vaccines, tolerogenic DNA immuno-therapy vaccines are intended to suppress immune reactivity towards an antigen, rather than activating immune responses against it. These vaccines do not stimulate immunity against the encoded antigen, or change the type of stimulation (as e.g. antigenic desensitization vaccination approaches for allergies does), but instead cause depletion, and/or lack of function, and/or death of self-reactive T cells. In order to do so, the antigen must be presented to the immune system without co-stimulation or inflammatory effects, which would otherwise prime stimulatory immune responses. This approach of presenting an antigen to be ignored by the immune system, or tolerized against, could be of value in treating autoimmune diseases, as the specific mechanism of the disease would thus be targeted rather than systemically suppressing the entire immune response. A tolerogenic DNA immuno-therapy vaccine is thus a mild method of modulating undesired immune responses.

The end goal of a T1D-specific tolerogenic DNA immuno-therapy vaccine is to preserve beta cell function and endogenous insulin production. This may occur through prevention or delay of disease (especially valuable in pediatric and young adult cohorts where monitoring is difficult and "normalcy" of life is a major patient driver) or extension of the "honey moon phase" of minimal monitoring and insulin usage that often occurs for the first six months after T1D diagnosis.

While DNA based vaccines are known to be safe, none of the (stimulatory or tolerogenic) DNA vaccines that have been tested in clinical studies have sufficient potency as a stand-alone approach for treatment of e.g. T1D. Tolerogenic DNA vaccines known in the art showed little efficacy and typically required highly artificial systems to induce the desired effects. There is thus a need in the art for tolerogenic DNA immuno-therapy vaccines with significantly increased potency, without compromising the safety profile and preferably also without requiring an inconvenient administration regimen.

SUMMARY

The present invention relates to a multi-cistronic vector/plasmid which co-expresses/encodes a cellularly retained antigen, such as insulin, as well as secreted immune modifiers such as TGF-β, IL-10, and optionally IL-2. The present invention furthermore relates to DNA immuno-therapy vaccines comprising such plasmids as well as such pharmaceutical formulations and kits thereof. The present invention finally relates to the medicinal use of such products as well as methods for producing such plasmids.

The plasmids/DNA immuno-therapy vaccines herein have therapeutic potential in treatment of autoimmune diseases that are mainly T cell driven, such as e.g. type 1 diabetes (T1D).

In one aspect the present invention provides plasmid which encodes:
  i. an insulin antigen;
  ii. TGF-β; and
  iii. IL-10.

DESCRIPTION

Figure 1:
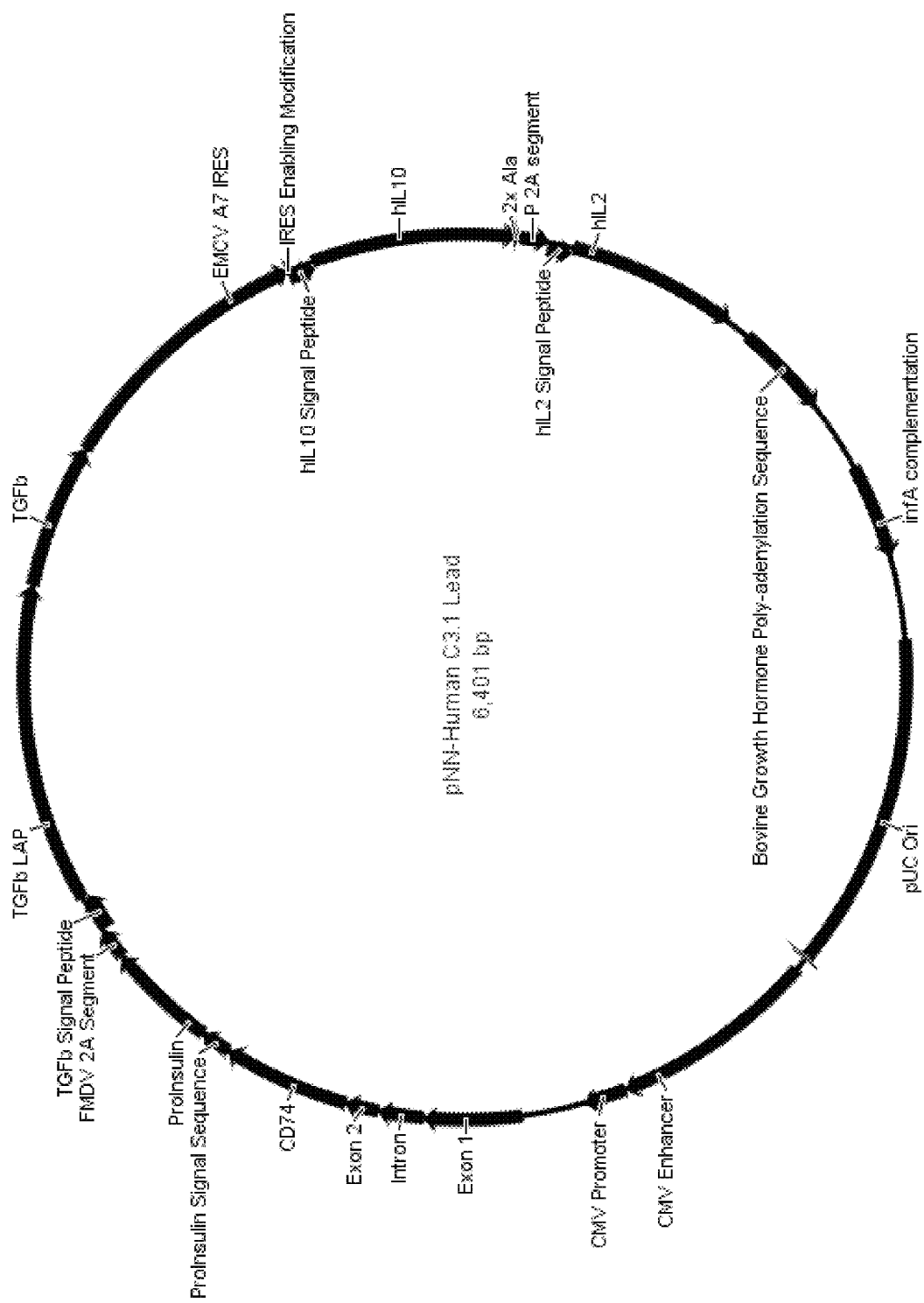
FIG. 1. Circular plasmid map.
Figure 2:
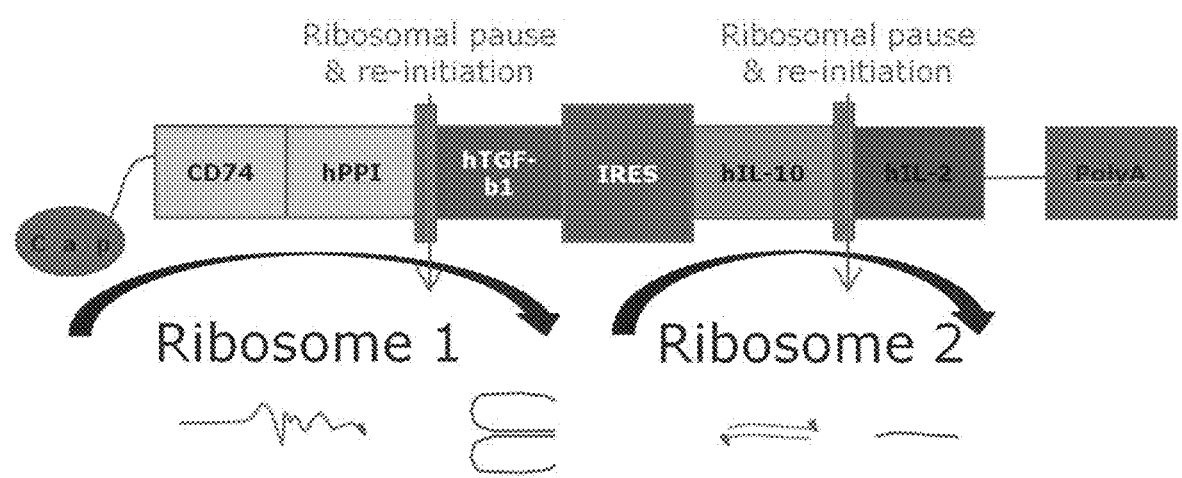
FIG. 2. mRNA and translated protein map for the vector products of the plasmid from FIG. 1.
Figure 3:
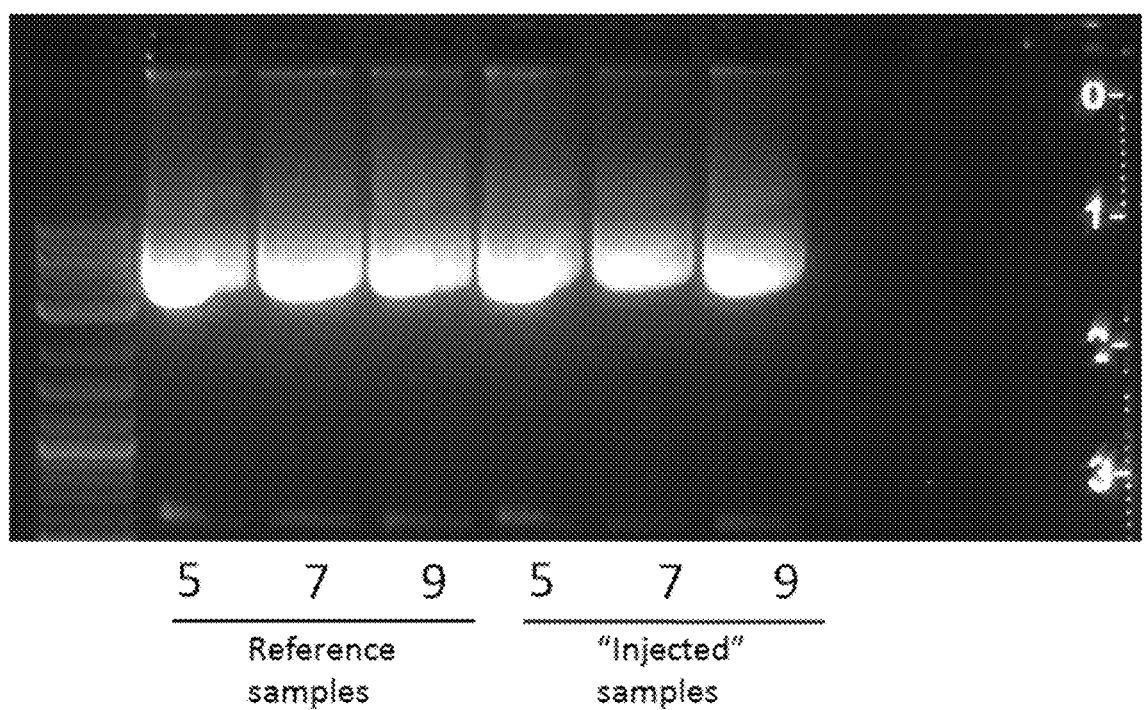
FIG. 3. Plasmid shear stability on three injection passages via a G30 needle.
Figure 4:
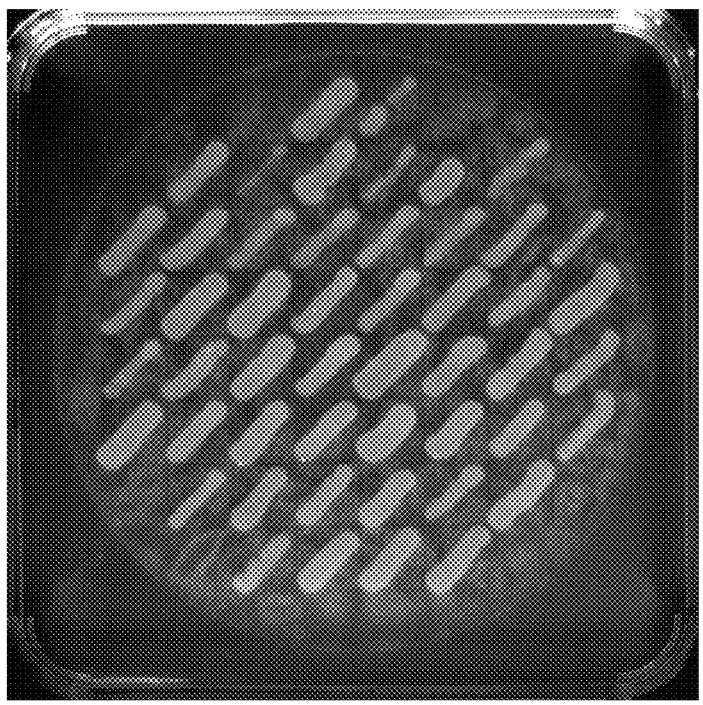
FIG. 4. Confirmation of plasmid retention phenotype by growth at 30° C. (passages 1-50 using 17 hours incubation and passages 51-100 using 22 hours incubation).
Figure 4:
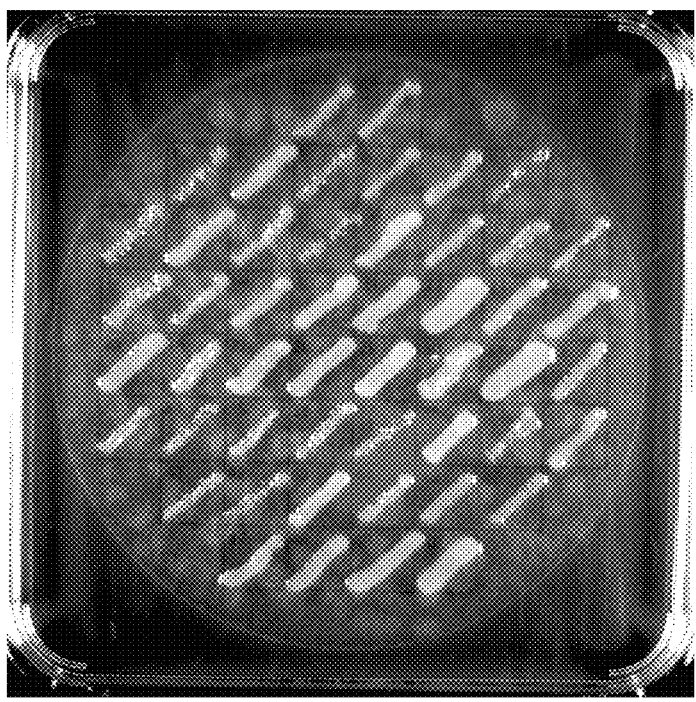

The inventor of the present invention has herein provided a single vector which drives expression of multiple secreted cytokines, as well as an cellularly retained antigen, from a single promoter/multi-cistronic mRNA.

DNA immuno-therapy vaccination with a single vector encoding all components of the therapy in a single cell is highly preferred over immuno-therapy vaccination with a mixture of separate vectors/plasmids each driving expression of single components, as random transfection of cells with different vectors does not guarantee expression of all components, or even any specific ratio of components, from a given, specific transfected cell.

Transfection of a single multi-cistronic plasmid/vector results in a specifically engineered local environment/micro-environment around the transfected cell. In this way, combinations of immuno-modulators can be added to the antigen such that they potentiate the desired immunologic effect of single T cells without the requirement of high systemic immuno-modulator doses that could otherwise cause adverse events and broad immunosuppression.

This local restriction of immuno-modulator production of host cells transfected with the DNA immuno-therapy vaccine allows for the safe use of highly potent cytokine hormones, which are synergistic for modification of T cell responses, but cannot be dosed either frequently enough for effect, and/or titrated to give the desired response, without unacceptable adverse events.

For example, Interleukin-10 (IL-10) and Transforming Growth Factor-beta1 (TGF-β1) are both known to be able to induce regulatory T cells (Tregs) from naïve $CD4^+$ T cells. However, the IL-10/TGF-β1 combination provides a synergistic effect (15 to 20 fold more efficacious) in inducing Tregs than either of the two cytokines alone (U.S. Pat. No. 6,083,919 A) and this combination furthermore results in immune tolerance in a broader population of target cells than either cytokine alone (Zeller J C, Panoskaltsis-Mortari A, Murphy W J, et. al. 1999 J Immunol. 163(7):3684-91).

Additionally, Interleukin-2 (IL-2) is known to both expand and stabilize Tregs but may on the other hand also contribute to inflammatory responses. The combination of IL-2 and IL-10, however, results in suppressive Tregs rather than inflammatory stimulation. As circulating T cells encounter cells that are transfected with the DNA immuno-therapy vaccine herein, they are temporarily exposed to sub-optimal concentrations of IL-10 and IL-2. The circulating T cells are slightly biased toward tolerance, and if they are also reactive toward the co-expressed antigen (e.g. insulin) they will bind to the transfected cell and thus receive a longer duration of immuno-modulator exposure and in addition they will also receive another signal that programs/re-educates them for suppressive effects. In this way, those T cells which are responsive to the encoded antigen are selectively re-educated to a suppressive phenotype when they encounter the transfected cell.

The plasmids/vectors/DNA immuno-therapy vaccines herein are thus designed for induction of antigen specific Tregs accumulating at sites of autoimmunity to dampen disease (e.g. the pancreas in T1D) rather than to directly impact disease through the expressed cytokine hormones.

In addition to an antigen (insulin in the example of T1D), the vector/operon/plasmid herein encodes at least two cytokines (e.g. TGF-β1 and IL-10) which together synergistically suppress antigen presenting cells, as well as T cell function, and drive induction of Tregs. This effect is enhanced if it also occurs in combination with effective exposure to antigen.

In one embodiment, TGF-β1 is in a constitutively active form that does not require processing or an inflammatory environment for function. While Tregs can be produced from naïve T cells via exposure to antigen and TGF-β1, Tregs are, however, "plastic" meaning that they can de-differentiate and convert into Th17 effector cells and then cause more, not less, autoimmune destruction. The combination of IL-10 with TGF-β1, in addition to being a more potent immuno-modulator, suppresses the environment that would produce pathogenic Th17 cells rather than Tregs.

In one embodiment, the multi-cistronic vector herein also encodes IL-2 in addition to antigen, TGF-β1, IL-10. IL-2 expands Treg numbers and stabilizes their phenotype (prevents Treg cells from de-differentiation into effector T cells) and thus increases their functional lifespan in inflamed target tissues.

These three cytokines (TGF-β1, IL-10, and IL-2), in combination with antigen, thus have well-known synergistic effects for inducing tolerance by the following mechanisms: (i) significantly enhanced generation of antigen-specific suppressive Tregs, (ii) longer Treg lifespan, and (iii) greater efficacy per individual Treg cell in suppressing inflammation/auto-reactivity. However, the required concentrations of systemically infused purified cytokine would have a number of serious, or maybe even lethal, side effects, such as: (i) lethal fibrosis from excess TGF-β1, (ii) flu-like symptoms, (iii) capillary leak syndrome from excess IL-2, (iv) broad immunosuppression leading to chronic infections, (v) enhanced tumor development as well as (vi) anemia from excess IL-10.

By co-expressing these cytokines from the same vector/plasmid, and therefore by the same cell presenting the antigen to the immune system, the vector achieves the desired local environment for tolerance induction without systemic action and corresponding side-effects that would otherwise result from high-dose purified cytokine administration.

Injection of "naked"/"bare" plasmid/vector DNA (vector and buffer alone) has a very low uptake and transfection rate—fewer than one in about 100,000 plasmid molecules transfects a cell, while the rest are degraded and thus without any biological effect. This extremely low inefficiency of transfection provides a safety mechanism for distributing and limiting the transfected cells.

Administration of systemically active quantities of any of these cytokines, either by administration of mature proteins or by high-efficiency viral vector transduction, would be difficult, if not impossible, to titrate for a safe and effective dose. Limiting the total exposure to a very small systemic dose distributed in a few high expressing micro-environments leads to a highly advantageous safety and efficacy profile.

The combination of antigen and these three cytokines herein produces an efficient protection from T1D development and even appears to be able to stably reverse disease progression. Due to the low transfection efficiency of the bare DNA plasmid/vector injection, very few cells produce these recombinant proteins and there is thus no detectable change in serum cytokine levels from plasmid/vector encoded cytokines—and therefore no detectable immune stimulation or immuno-suppression toward any other antigens than the antigen encoded by the plasmid/vector (pre-proinsulin). This results in a desirable safety profile.

Normally, DNA vaccines perform poorly in connection with subcutaneous (s.c.) injection and are therefore typically administered using intramuscular injection (often with electroporation) or alternatively using intradermal jet injection requiring a cumbersome device as well as significant maintenance and calibration. As most side effect issues with intramuscular injection are adjuvant-related (injection site irritation) they are therefore not a concern for the bare DNA immuno-therapy vaccine format herein. Additionally, the volumes injected are usually relatively small and therefore do not cause significant muscle distension and pain. In one embodiment, the volumes injected are 1 ml or less. In another embodiment, the volumes injected are approximately 0.6 or 0.5 ml. Regardless, the multi cytokine plasmid/vector provided herein unexpectedly appears to provide protection from T1D even when administered through the s.c. route, thereby allowing multiple potential dosing formats for patients.

In addition to providing local synergy, by encoding all three or four of the translated products by a single plasmid/vector and a single promoter, the regulatory burden and drug substance release criteria are furthermore simplified with the provision of the multi-cistronic plasmid herein.

In contrast, if each of the protein products is produced from a separate plasmid, then the synergistic value of co-expression from the same transfected cell would then potentially be lost or reduced as each plasmid/vector transfection would be an independent event, likely targeting different cells. If the three to four recombinant proteins are produced from two, three, or four individual plasmids/vectors, any synergistic effects in the local environment of the transfected cell are potentially lost; in addition, several individual clinical trials would thus be necessary (one for each plasmid and each combination). Producing all proteins from a single plasmid/vector and single mRNA relieves the requirements to test multiple individual molecules and determining ideal co-packaging ratios inherent to a multiple plasmid/vector format.

Any vector formats suitable for the present invention can be used herein, such as plasmids (replicating or passive), mini-circles, linear vectors (MiLVs), viral vectors (both integrating [e.g. lentiviral] and non-integrating [e.g. adenoviral]), cosmids, bacterial artificial chromosomes (BACs), human artificial chromosomes (HACs), etc.

Furthermore, any permissible transfection enhancement method can be used herein: e.g. electroporation, sonoporation (ultrasound enhancement, with or without microbubble contrast enhancement), lipid/polymer aggregates, hydrodynamics (pressure via high injection volume), bio-ballistics/gene-gun (deposition through skin via compressed gas), etc.

In one embodiment, non-replicating episomal plasmid DNA is used herein due to: i) multiple copies of mRNA derived from a single plasmid transfection, and ii) extended stability and function of plasmid nucleic acids over mRNA and other DNA vector formats. Thus, while both mRNA and DNA-based expression systems can provide intracellular delivery and co-localization, plasmid based systems provide greater control and persistence of dosing.

In one embodiment, plasmids/vectors encode four proteins:
  i) an antigen,
  ii) TGF beta 1 (TGF-β1),
  iii) Interleukin-10, and
  iv) Interleukin-2.

In one embodiment, the antigen is an endosomally-targeted T1D relevant antigen, such as insulin or GAD65. Endosomal targeting can be done via e.g. a li/CD74 fusion, a LIMPII/SCARB fusion, or a transferrin receptor fusion.

In one embodiment, TGF-β1 is in an activated form.

Expression of four proteins from one plasmid/vector is possible e.g. if the desired sequences are separated either with A) separate promoters, B) an IRES (Internal Ribosome Entry Site) sequences which recruit a new ribosome to translate each segment, or C) viral 2A sequences (e.g. FMDV 2A or TaV 2A sequences) which are translated and induce a ribosomal pause/skip which results in production of separate polypeptides from a single open reading frame. However, in practice, each of these strategies is complex and difficult to enable.

Expression of four independent proteins from a single plasmid/vector is most easily achieved by having a separate promoter for each gene. However, this format has significant disadvantages in that it A) results in a very large, unstable, and hard to produce plasmid due to the excess length of multiple promoters, B) results in unpredictable behaviour of the translated proteins relative to each other (they are no longer produced in fixed ratios to each other), C) each promoter may be independently silenced, leading to selective expression of some genes but not others required for full efficacy, and D) a lack of regulatory simplicity. In contrast, IRES elements and 2A sequences operate on the mRNA and translation levels and reproducibly co-express fixed ratios of each protein from a single promoter.

Each of the four classes of IRES elements has different co-factor requirements for function as well as different sequence requirements for the downstream gene to be translated. For instance, the EMCV (EndoMyoCarditis Virus) IRES is a 630 base pair type 1 IRES which utilizes all eukaryotic translation initiation factors while the CrPv (Cricket Paralysis virus) IRES is a 200 base pair type 4 IRES that has no required cofactors but utilizes a non-standard initiation codon.

When IRES elements from different classes are utilized, they interfere with each other such that each type of IRES element can only be used once in each plasmid, and when used together, different types of IRES elements attenuate each other (decrease in efficacy) in ways that are difficult to predict.

Furthermore, shuffling the gene/IRES combinations result in unpredictable ratios of translated products as the interactions of the genes with the IRES elements are not static but context dependant on the flanking nucleotide sequences. In addition, IRES elements impose restrictions on the first few amino acid positions at or immediately following initiation. For instance, the CrPv IRES requires that the first amino acid be an alanine rather than the standard methionine and the EMCV IRES cannot tolerate P, W, C, R, or K amino acids within the first three codons. In one embodiment, to accommodate the N-terminal amino acid restrictions imposed by the EMCV IRES, the DNA vaccine contains a three Alanine extension to the N-terminal of the IL-10 gene.

In addition, each IRES element comprises a substantial number of base pairs, ranging from 230 bp to over 700 bp; the inclusion of multiple IRES elements thus increases the size and complexity of plasmids/vectors to the extent that many become unstable and difficult to be industrially produced due to spontaneous deletions and recombinations. Further, due to the high degree of secondary structure that IRES elements impart on the transcribed mRNAs that contain them, they increase the probability of activating pathogen recognition receptors (Dabo S, Meurs E F. 2012 Viruses 4(11):2598-635) in the transfected cell and producing stimulatory effects counter to the tolerance induction that is intended.

2A sequences, unlike IRES elements, do not interact with each other and therefore provide stable and consistent performance. However, they are translated themselves and therefore affect the folding, function, and stability of the final translated protein products. All 2A sequences result in a significant C-terminal fusion (19-22 aa) onto the 5' end of the sequences to be separated and also begin the 3' sequence with a proline. Some proteins are permissive of these modifications and some are not, leading to practical restrictions to the use of 2A sequences. For instance, the Interleukin-10 product is permissive of the 2A tail but both Interleukin-2 and TGF-β1 mis-fold and lose function if expressed upstream of a 2A tag. Therefore, while it is possible to express several independent proteins separated by 2A sequences, two of the four proteins herein cannot terminate in 2A tags and therefore other strategies must be utilized.

As each type of 2A amino acid sequence modifies ribosomal function during protein translation, it will have different efficiencies in the two core properties of the 2A family namely (i) separation of the juxtaposed gene products and (ii) processivity (re-initiation) into the second gene product. Different 2A sequences have different efficiencies at generating the ribosomal pause that breaks the peptide backbone (resulting in the two separate proteins) as well as different efficiencies at re-initiating the peptide synthesis of the second gene product.

The ability of the 2A sequences to separate protein products and re-initiate protein translation are dependent on the 2A amino acid sequence (Donnelly M L, Hughes L E, Luke G, et. al. 2001 J Gen Virol. 82(Pt 5):1027-41). Small variations in 2A amino acid sequences result in significantly different mixes of separated and fused flanking gene products, ranging from under 5% (>95% fused) to completely separated (0% fused or 100% separated).

Furthermore, the inventor has herein discovered that adjacent amino acid sequences encoding the two flanking protein products also affect efficiency of re-initiation and separation of the 2A sequences, leading to significant deviations from reported results. Re-initiation efficiency thus varies depending on the type of 2A amino acid sequence used as well as the environment provided by the adjacent amino acid sequences, and thus the ratio of the pre-2A gene product and separation of the proteins will be determined by both the 2A amino acid sequence used and its context.

In one embodiment, "FMDV 2A" is inserted between the antigen encoding sequence and the TGF-β1 encoding sequence herein; resulting in 100% separation, as well as a 1:1 ratio, of the protein products.

In another embodiment, "TaV 2A" may be inserted between the IL-10 encoding sequence and the IL-2 encoding sequence herein, resulting in about 50% separate products as well as a 10 to 6 ratio of the protein products. Each transfected cell thus delivers a relatively low dose of Interleukin-2, that is incapable of stimulating effector T cells, and a higher dose of Interleukin-10 to bias the T cells toward the Treg phenotype. Since the production of fused IL-10/IL-2 is disadvantageous, attempts to engineer increased cleavage efficiency of the TaV 2A segment were made. An attempt to precede the 2A segment with an "insulator segment", which is an element that extends the translated region upstream of the TaV 2A to reduce upstream sequence impact on the 2A element, did not improve separation. In a different attempt to solve the fusion problem, an upstream uncoupler segment with a translated protein sequence of GSG was added; however, this approach resulted only in an incremental improvement of cleavage efficiency.

As such, cytokine fusions, resulting from separation of the IL-10 and IL-2 encoding genes by a TAV 2A, are likely to be immunogenic, In a further embodiment, the vector/plasmid herein has a "P 2A" segment. Separation of the IL-10 and IL-2 encoding genes by a P2A results in complete or near-complete separation of the protein products as well as a ratio of at least twice as much (or maybe even up to four or five times as much) IL-10 compared to IL-2.

In order to address the shortcomings of the IRES-only and 2A-only systems described above, the four cDNA sequences herein (antigen, TGF-β1, IL-10, IL-2) are arranged in pairs before and after a single IRES. Each pair is further separated by a 2A sequence, which induces ribosomal skipping and production of independent proteins from each sequence in the polyprotein pair. As TGF-β1 and IL-2 may not be on the N-terminal side of the fusion, one of them must terminate at the central IRES site and the other one must end the translated portion of the mRNA sequence.

The chronology/sequence of expressed proteins and IRES/2A elements herein may therefore be as follows: (i) Antigen, (ii) FMDV 2A, (iii) TGF beta 1, (iv) IRES, (v) IL-10, (vi) P 2A, and (vii) IL-2. As a consequence, all four proteins can be independently expressed from a single operon/gene segment in a stable and predictable fashion. As each of these proteins is expressed from a single mRNA, the ratios of each product are fixed—it is not possible to generate an excess of IL-2 over IL-10 for instance.

Besides using a combination of IRES and 2A elements for separation of encoded genes, an alternative solution herein could be use of a bidirectional promoter to generate 2 mRNAs—these mRNAs would each encode a pair of proteins rather than all four in one mRNA molecule. Equivalent arrangements may therefore be constructed utilizing pairs of expression cassettes appropriately arranged around a bidirectional mammalian promoter and utilizing separating 2A sequences and/or IRES elements. This approach is, however, associated with disadvantages, primarily due to the large size of bi-directional promoters but also a potential increased regulatory burden having separate mRNA elements included in one medicinal product. Preferred embodiments herein therefore utilize a single promoter and a combination of IRES and 2A elements rather than a bidirectional promoter.

In theory, some 2A sequences could be replaced with intracellular endogenous protease sensitive sequences. However, the inventor has herein discovered that such proteases are associated with significant disadvantages (e.g. lack of reported function resulting in secretion of fused protein products).

In order for the antigen to be processed and presented to the immune system within the local environment of the plasmid encoded cytokine hormones, the antigen must be retained within the transfected cell. In the case of type 1 diabetes, production of active insulin would potentially lead to undesirable lowering of blood glucose if it were to be secreted or otherwise released from the transfected cell.

In order to avoid antigen secretion, any secretion signals can be removed from the antigen encoding sequence, e.g. remove secretion signal coding sequence from the nucleic acid sequence encoding pre-proinsulin, thus proinsulin rather than pre-proinsulin would be generated, thus allowing the antigen to accumulate inside the transfected cell. While this translated antigen product (e.g. insulin) would not be actively secreted, it could be released during lysis due to necrosis resulting from attack by $CD8^+$ T cells. Additionally, the signal sequence of insulin is a region known to contain disease-relevant epitopes (potentially inducing auto-immunity) and the inclusion of the signal sequence therefore ensures broader tolerance induction and a higher probability of reducing disease.

Additionally, cytoplasmic retention of antigen only allows for processing via the proteasome and presentation via the MHC class I pathway, which detects intracellular pathogens via $CD8^+$ T cells. As $CD4^+$ T cells are significant contributors to pro-inflammatory cytokines and most, if not all, autoimmunity suppressing Tregs are $CD4^+$, broadening the presentation of antigen to include MHC class II, which is recognized by $CD4^+$ T cells, may be advantageous.

MHC class II processing and CD4+ T cell stimulation normally do not include intracellular antigen, as access to this pathway is via endocytosis of extra cellular antigen. Normally, protein products produced within a transfected cell are only presented via the default intracellular/proteasomal processing pathway and MHC class I, resulting in CD8+ T cell effects but not CD4+ T cell effects. In order to target both CD4+ and CD8+ T cells for immunomodulation the preferred embodiment also includes factors leading to MHC class II presentation.

In principle, to induce MHC class II presentation, the antigen can be fused to any partner that directs the fusion to an endosomal compartment, but there are functional differences in activity and exposure. Transferrin receptor, also known as iron transporting protein receptor, fusions cycle from the plasma membrane/extracellular space to the endosome and therefore may also expose other immune cells to whole antigen, such as B cells, macrophages, etc. LimpII/SCARB fusions target directly to the endosome, but preferentially to the early endosome and sometimes result in over processing and total destruction of the antigen. Ii (CD74) fusions, utilizing the same chaperone signal that MHC class II uses for late endosome localization, deliver the antigen and MHC class II to the same vesicles at the same developmental stage and maximize the likelihood of effectively presenting antigen in the context of MHC class II. Additionally, even with endosomal sorting from Ii fusions, the preproinsulin secretion sequence must be rendered inactive or the antigen would also be secreted and lost prior to processing.

Blockade of insulin antigen secretion has alternatively been accomplished herein by mutating two amino acids required for secretion tag removal by the SRP (Signal Recognition Particle) on the Rough Endoplasmic Reticulum. Ala (A) to Glu (E) mutations completely abolish preproinsulin maturation and secretion, while maintaining the required epitope structure of the antigen for best tolerance induction.

In one embodiment, the plasmid DNA vaccine is used herein. The plasmid is grown/replicated for example in $E.$ $coli$, and isolated/purified from the media, and subsequently formulated in liquid formulations e.g. water, saline, PBS liquid formulations, or as a lyophilized powder for intradermal jet injection, intranasal administration, or inhalation. In one embodiment, the plasmid herein is formulated in an aqueous pharmaceutical formulation optionally comprising stabilisers. Any suitable microbial system may be utilized for plasmid production.

Stabilizers in the formulation include, but are not limited to, chelating agents, such as EDTA, EGTA, or DPTA for scavenging $Mg^{++}$ and $Fe^{+++}$ which may otherwise be involved in degradation of DNA, and/or citrate, which protects the plasmid from non-specific degradation effects. In one embodiment, the plasmid herein may be formulated in isotonic PBS or alternatively TRIS+citrate+EDTA. Such plasmids have the advantages of being stable, easy to produce and being safe and convenient in use.

In another embodiment, delivery agents, such as virus, lipids, liposomes, co-packaging etc., could be added in connection with the present invention. However, the use of delivery agents herein may have potential problems with immunity, viral integration, etc.

Definitions

Antigen: the DNA immuno-therapy vaccine herein encodes an antigen. The antigen herein can be any type of immunogenic disease-associated protein or fragment thereof that can be recognized by the T cell component of the immune system. For example, in the case of type 1 diabetes treatment or prevention, an insulin antigen may be used. In one example, the insulin antigen is the InsB 9-23 immunodominant peptide. For multiple sclerosis DNA immunotherapy vaccines herein, a myelin basic protein (MBP), myelin oligodendrocyte protein (MOG), and/or proteolipid protein (PLP) antigen may be used as antigen. Similar protein antigen encoding sequences for representative antigens from alopecia, polymyositis/dermatomyositis, celiac sprue, and protein allergens (e.g. peanut protein ara h 2) are also examples of antigens suitable for use in the DNA immuno-therapy vaccines herein.

Antigen targeting: In one embodiment, antigen herein is endosomally targeted. Antigens herein include whole protein, secretion-deficient pre-proteins, or a functional or immuno-dominant peptide fragment thereof.

For example, insulin antigen herein is an antigen for use in immune modulatory therapy and not a glucose lowering agent. It should therefore not be fully processed/matured or secreted in order to make sure that it is presented on MHC molecules to circulatory T cells. The DNA immuno-therapy vaccine herein does therefore not result in increased insulin levels in the blood but rather results in an increased presentation of antigens to the immune system, in particular the T cells.

Therefore, insulin antigen herein can be small immunodominant peptide encoding fragments (e.g. insulin B chain 9-23 peptide, including shifted register peptides displaying equivalent T cell epitopes), whole proinsulin, which lacks the required secretion sequence but otherwise intact, or pre-proinsulin muteins that contain the secretion sequence but are modified to prevent secretory function.

Examples of Insulin antigens herein include:

```
Mouse proinsulin (SEQ ID NO: 1):
FVNQHLCGSHLVEALYLVCGERGFFYTPKTRREAEDLQVGQVELGGGPGA

GSLQPLALEGSLQKRGIVEQCCTSICSLYQLENYCN

Human proinsulin (SEQ ID NO: 2):
FVNQHLCGSHLVEALYLVCGERGFFYTPKTRREAEDLQVGQVELGGGPGA

GSLQPLALEGSLQKRGIVEQCCTSICSLYQLENYCN

Modified mouse pre-proinsulin that is not secreted
(substitutions in relation to wt pre-proinsulin
shown with bold and underline (SEQ ID NO: 3)):
MALWMRLLPLLALLALWGPDPEQEFVNQHLCGSHLVEALYLVCGERGFFY

TPKTRREAEDLQVGQVELGGGPGAGSLQPLALEGSLQKRGIVEQCCTSIC

SLYQLENYCN

Modified Human pre-proinsulin that is not secreted
(substitutions in relation to wt pre-proinsulin
shown with bold and underline (SEQ ID NO: 4)):
MALWMRLLPLLALLALWGPDPEQEFVNQHLCGSHLVEALYLVCGERGFFY

TPKTRREAEDLQVGQVELGGGPGAGSLQPLALEGSLQKRGIVEQCCTSIC

SLYQLENYCN

Mouse wt pre-proinsulin (SEQ ID NO: 5):
ALWMRLLPLLALLALWGPDPAQAFVNQHLCGSHLVEALYLVCGERGFFYT

PKTRREAEDLQVGQVELGGGPGAGSLQPLALEGSLQKRGIVEQCCTSICS

LYQLENYCN
```

```
Human wt pre-proinsulin (SEQ ID NO: 6):
MALWMRLLPLLALLALWGPDPAQAFVNQHLCGSHLVEALYLVCGERGFFY

TPKTRREAEDLQVGQVELGGGPGAGSLQPLALEGSLQKRGIVEQCCTSIC

SLYQLENYCN

Insulin peptide "InsB 9-23" identical between
mouse and human: (SEQ ID NO: 7)
SHLVEALYLVCGERG Modified InsB 9-23 (substitutions in relation to
wt InsB 9-23 shown with bold and underline
(SEQ ID NO: 8) and (SEQ ID NO: 27)):
SHLVEALYLVCGEEG
and

SHLVEALYLVCGGEG
```

Insulin antigens herein may thus accumulate in the cytosol of the transfected host cell and can thus be presented via MHC class I, or be released upon cytolysis.

Endosomal targeting resulting in MHC class II presentation may be accomplished herein via fusion of the antigen sequence with leader sequences which form transmembrane segments with cytoplasmic "YXXØ" (SEQ ID NO:30) sequences, in which Y is tyrosine, X is any amino acid, and Ø is a bulky hydrophobic amino acid such as tryptophan or isoleucine, "[DE]XXXL[LI]" (SEQ ID NO:31) where D and E are aspartic or glutamic acid respectively, while L and I are leucine and isoleucine respectively, or "DXXLL" (SEQ ID NO:32) endosomal/lysosomal sorting signals, which are underlined in the following exemplary sequences. Protein domains that include these signals therefore target or cycle to the endosome/lysosome include: transferrin receptor, LimpII, or CD74, also known as Invariant chain, MHC II chaperone, or Ii, or any similar domain.

Examples of endosomal targeting domains herein include, but are not limited to:

```
Mouse CD74/Invariant chain (Ii) endosomal
targeting domain (SEQ ID NO; 9):
MDDQRDLISNHEQLPILGNRPREPERCSRGALYTGVSVLVALLLAGQATT

AYFLYQQQGRLDKLTITSQNLQLESLRMKLP

Human CD74/Invariant chain (Ii) endosomal
targeting domain (SEQ ID NO: 10):
MHRRRSRSCREDQKPVMDDQRDLISNNEQLPMLGRRPGAPESKCSRGALY

TGFSILVTLLLAGQATTAYFLYQQQGRLDKLTITSQNLQLESLRMKLP
```

Type 1 diabetes: Type 1 diabetes (T1D) is considered to be a chronic autoimmune disease, where auto-aggressive T cells infiltrate the islets of Langerhans in the pancreas and play an important role by specifically destroying the insulin-producing beta-cell population. Once a significant number of islet cells are destroyed, reduced amounts of insulin, or no insulin at all, will result in insulin deficiency and hyperglycemia in the patient. T1D patients are thus unable to produce enough insulin and need regular injections of the hormone are needed throughout life. Some Type 1 Diabetes patients are diagnosed with "type 1.5 Diabetes", "latent autoimmune diabetes"/LADA, "double diabetes" etc., which are diabetes diseases carrying symptoms of both Type 1 Diabetes and Type 2 Diabetes—all diabetes diseases carrying trains of both Type 1 and Type 2 Diabetes are thus also contained in the term "Type 1 Diabetes" herein.

Tolerogenic DNA vaccine: DNA-based immuno-therapy vaccines/vectors/plasmids herein are designed to switch off or down-regulate the part of the immune system responsible for destroying normal healthy "self" cells and thus prevent or ameliorate T cell-based autoimmunity.

The term "DNA immuno-therapy vaccine" as used herein is intended to mean a compound or composition comprising a DNA molecule and which is administered to a subject in order to reduce the risk of said subject developing one or more diseases.

In some embodiments, DNA based immuno-therapy vaccines herein are plasmids/vectors encoding particular antigens. Following vaccination, these plasmids are taken up by, in other words, transfected into antigen presenting cells in the host's body. The "transfected" host cells then produce the antigen and present small fragments of the antigen to the immune system, in particular the T cells. This approach leads to a modification of specific T cell responses to the encoded antigen as well as minimal modification to immune responses to other (non-encoded or "irrelevant") antigens. Only a very few host cells are typically transformed with the DNA vaccine plasmid/vector herein, meaning that likely fewer than one out of hundred thousand, one out of five hundred thousand, or even fewer than one out of a million plasmid/vector molecules eventually enter a host cell. DNA vaccines herein thus represent a very mild and specific approach for modulating immune responses to antigens such as insulin in T1D patients or patients at risk of developing T1D.

Plasmid: A plasmid is a small DNA molecule that is most commonly found in bacteria as small, circular, double-stranded DNA molecules. Artificial plasmids are widely used as vectors in molecular cloning, serving to drive the replication of recombinant DNA sequences within host organisms. Plasmids can be engineered to be suitable for use as immuno-therapy DNA vaccines. Plasmids are considered replicons, a unit of DNA capable of replicating autonomously within a suitable host. Plasmids can be transmitted from one bacterium to another bacterium, which could be of the same or different bacterial species via three main mechanisms: transformation, transduction, and conjugation. DNA vaccine plasmids can be taken up by a host cell by passive transformation—usually at a relatively low rate. The plasmids herein replicate efficiently—but do not drive protein expression—in bacteria. The plasmids herein furthermore drive protein expression—but not replication of plasmid—in humans and other mammals, e.g. mice. In one embodiment, a pVAX1 vector (Invitrogen/LifeTechnologies) is used as a scaffold herein for inserting the elements that are part of the present invention. Other suitable vector scaffolds herein include any vector backbone containing a eukaryotic promoter element, a prokaryotic high copy origin of replication, and a selection system for plasmid maintenance.

Selection gene and selection system: In one aspect, DNA immuno-therapy vaccines herein comprise a selection gene/selection marker for manufacturing purposes. The selectable marker herein is e.g. a gene that confers resistance to a cell toxin—e.g. an antibiotic such as ampicillin, kanamycin, chloramphenicol, streptomycin, etc.

Other types of suitable selection systems herein include e.g. conditional lethal silencing systems (e.g. CcdA/CcdB or ParD/ParE Hok/Sok type systems), or sequences that complements a genomic defect in the production cell strain and thus permits growth of an otherwise inviable host (e.g. dapD$^-$ or pyrF$^-$ auxotrophic complementation, infA$^-$ translation initiation complementation, etc.)

Production cells harbouring the plasmid/DNA vaccine, which includes the selection marker, will survive when exposed to the toxin/antibiotic/condition, while those that have failed to take up plasmid sequences will die. As such, in one embodiment, DNA vaccines herein comprises the nucleic acid sequence encoding a selection marker in order to provide for higher yield/purity and more efficient production/replication in production cells, such as E. coli.

While antibiotic selection is a common laboratory strategy there may be advantages associated with antibiotic-free selection systems—e.g. in relation to more efficient regulatory processes. While vectors which do not contain a selection mechanism such as minicircles, synthetic linear vectors, etc., can also be used herein, these implementations are associated with certain drawbacks in production, in particular due to increased production and quality control costs.

Examples of complementation ("rescue") strategies are known in the prior art, however these strategies suffer from various disadvantages.

Metabolic complementation systems such as dapD [lysine biosynthesis] or pyrF [uridine biosynthesis] systems, often result in "cross-feeding" during high density E. coli production, where a plasmid-containing bacterium will produce and secrete an excess of the required compound and thereby "relaxing" the selection pressure for neighbouring bacteria without the plasmid.

Another example of a suitable selection system herein are plasmids encoding essential proteins, such as infA, encoding IF1/Initiation Factor 1 which is required for protein synthesis. In this selection system, cross-feeding does not occur because the infA protein is not secreted. However, it is not possible to further modify the plasmid or expand plasmid-deficient cells as there is no way to exogenously complement the required protein/infA (J Bacteriol. 1994 January; 176(1):198-205 and J Biotechnol. 2004 Jul. 1; 111(1):17-30).

In order to circumvent the disadvantages associated with the infA selection system, an alternative selection system has been provided herein with a temperature-sensitive translation switch (or "thermosensor") from the invasion protein gene prfA of L. monocytogenes (Cell. 2002 Sep. 6; 110(5): 551-61). By placing the hairpin forming portion of an RNA "thermosensor" sequence upstream of the E. coli genomic copies of infA via standard recombination technology, expression thereof becomes regulated via control of the fermentation temperature, enabling slow growth of plasmid free cells at 37° C., and rapid cell death at temperatures <30° C. Transformation of the engineered thermo sensitive E. coli production strain with plasmids expressing wt infA thus allow full normal growth rates at all temperatures, allowing for plasmid-free expansion at 37° C. as well as stringent selection for plasmid at 30° C. Additionally, this system generates no selective pressure for wt E. coli to retain the plasmid and it is thus lost within 8 hours in culture—ensuring no environmental persistence of the therapeutic plasmid.

```
wt E. coli infA nucleotide sequence (SEQ ID
NO: 11):
ATGGCCAAAGAAGACAATATTGAAATGCAAGGTACCGTTCTTGAAACGTT

GCCTAATACCATGTTCCGCGTAGAGTTAGAAAACGGTCACGTGGTTACTG

CACACATCTCCGGTAAAATGCGCAAAAACTACATCCGCATCCTGACGGGC

GACAAAGTGACTGTTGAACTGACCCCGTACGACCTGAGCAAAGGCCGCAT

TGTCTTCCGTAGTCGCTGA
```

-continued

```
wt E. coli IF1 protein sequence resulting from
translation of the infA gene (initial methionine/M
not included in prfA fusion-(SEQ ID NO: 12)):
MAKEDNIEMQGTVLETLPNTMFRVELENGHVVTAHISGKMRKNYIRILTG

DKVTVELTPYDLSKGRIVFRSR
```

E. coli production cell lines used herein for production of DNA immuno-therapy vaccine plasmids may thus harbour the following thermo sensitive prfA nucleotide sequence:

```
wt L. monocytogenes prfA ("thermo sensor
hairpin") nucleotide sequence (Shine Dalgarno
underlined, ATG start bolded-(SEQ ID NO: 13)):
TGTAAAAAACATCATTTAGCGTGACTTTCTTTCAACAGCTAACAATTGTT

GTTACTGCCTAATGTTTTTAGGGTATTTTAAAAAAGGGCGATAAAAAACG

ATTGGGGGATGAGAAATGAACGCTCAA wt L. monocytogenes prfA protein sequence (fused
upstream of E. coli IF1-resulting from translation
of SEQ ID NO: 13):
MNAQ
```

Origin of replication ("Ori"): The origin of replication, also called the replication origin, is a particular sequence in a genome at which replication of the DNA strand is initiated. In one embodiment, origin of replication sites herein includes the "pUC Ori" which allows replication in the bacterial E. coli production cell line—but not in the mammalian host cells, i.e., cells from the body of the vaccinated subject/person/patient. Other suitable bacterial replication origins herein include but are not limited to: R6K, pBR322, ColE1, pMB1, 15A, pSC101, etc. In one aspect, the origin of replication herein is a high copy version which yields a high plasmid/biomass ratio for more efficient production. Vectors which do not contain an origin of replication, such as minicircles, synthetic linear vectors, etc., can also be used herein.

Promoter: A promoter is a region of DNA that initiates transcription of a particular gene. Promoters are located near the transcription start sites of genes, on the same strand and upstream on the DNA, which towards the 5' region of the sense strand. For the transcription to take place, the RNA polymerase must attach to the DNA near a gene. Promoters contain specific DNA sequences, such as response elements, that provide a secure initial binding site for RNA polymerase and for transcription factors that recruit RNA polymerase. Transcription factors have specific activator or repressor sequences that attach to specific promoters and regulate gene expression. Promoters thus represent critical elements that can work in concert with other regulatory regions, such as enhancers, silencers, boundary elements/insulators, to direct the level of transcription of a given gene. A classical promoter drives the production of a single messenger RNA (mRNA), whereas bidirectional promoters herein drive the production of two mRNAs immediately adjacent to the promoter, both upstream and downstream of the promoter.

In one embodiment, eukaryotic promoters are used herein. Eukaryotic promoters do not necessarily obey the one gene/one promoter rule, such as several viral promoters as well as promoters that exhibit broad expression (i.e. do not have narrow cell type specificities such as neuron-only expression). Examples of promoters herein that are capable of driving broad transcription of large multi-gene mRNA molecules include: the viral CMV immediate-early (IE) and SV40 promoters; endogenous EF1a, PGK1, Ubc, and beta actin promoters; and synthetic promoters such as the CAG hybrid promoter. Many other suitable mammalian promoters exist and more are being designed via synthetic biology efforts. Any promoter that results in the desired expression characteristics in human cells may be used in the DNA immuno-therapy vaccine plasmids herein.

Enhancers: Enhancers are DNA elements that increase the efficiency of promoters in producing mRNA transcripts. The enhancers herein may be matched (e.g. SV40 enhancer/CMV promoter) or unmatched. Any suitable enhancer/promoter combination for eukaryotic function can be used herein.

Eukaryotic translation start: The eukaryotic translation start sequence is usually referred to as the "Kozak" consensus sequence. The Kozak sequence on an mRNA molecule is recognized by the ribosome as the translational start site, from which a protein is encoded. The eukaryotic ribosome requires this sequence, or a variation thereof, to initiate protein translation. Kozak sequences are degenerate or variable and rarely match consensus sequences. In fact, consensus Kozak sequences are typically less efficient than wild type variants isolated from mammalian mRNAs. While weak Kozak sequences are regularly isolated from native mRNAs and likely play a role in translational control of low abundance proteins, DNA immuno-therapy vaccines herein preferably encode a medium or high efficiency Kozak sequence. Examples of useful Kozak sequences herein comprise the following nucleotide sequence: gccRccATGG (SEQ ID NO: 14), where lower case bases are the most common nucleotides but may vary while upper case nucleotides are fixed (R is the IUPAC uncertainty code for A or G bases), and the ATG indicates the translational start site of Methionine codon at position +1.

Endosome sorting signal: An endosome is a membrane-bounded compartment inside eukaryotic cells. Some proteins can be transported to endosomes and therein be degraded into peptide fragments. The peptide fragments can bind to MHC molecules present in the endosome to form MHC/peptide complexes, which can subsequently be transported to the cell surface in order to be presented to circulating T cells, particularly CD4$^+$ T cells. Sorting of proteins to endosomes is mediated by signals present within the cytosolic domains of the proteins. The endosomal signals are usually short linear amino acid sequences. Antigens herein are preferably targeted to the endosomes using an endosome sorting signal, such as e.g. YXXØ (SEQ ID NO:30), [DE]XXXL[LI] (SEQ ID NO:31), or DXXLL (SEQ ID NO:32) endosomal/lysosomal sorting signals. Endosome sorting signals include various naturally occurring or synthetic endosomal sorting signals. Examples herein include the endosome sorting signals present on Cd74/invariant chain/Ii, LimpII/SCARB, or transferrin receptor. Any endosomal targeting domain which is pharmaceutically acceptable and provides the desired function may be utilized. Fusion of such endosomal targeting domains to the antigens directs them to the endosomal compartment upon translation for increased efficacy. Endosomal sorting of antigens confers processing and presentation to the immune system in MHC class II complexes, in addition to constitutive presentation in MHC class I complexes, for more complete and robust induction of tolerance and possible expansion of Tregs (which cannot be accomplished via MHC class I/antigen complexes). In one embodiment, tolerogenic DNA vaccines herein encode a fusion of the antigen with the CD74/invariant chain/Ii to drive endosomal targeting and presentation of the antigen via MHC class II.

Introns: Introns are non-coding sequences within an mRNA. It is known that some introns significantly increase translation and function of mRNA. Accordingly, the inclusion of intron sequences may also be used herein. Standard introns, such as beta-globin, or any intron obeying mammalian splicing conventions, such as MCM7, may be utilized. In one embodiment, DNA immuno-therapy vaccine vectors herein comprise sequences encoding one or more introns. In another embodiment, DNA immunotherapy vaccine vectors herein do not possess sequences encoding introns.

Ribosomal pause tag: In connection with the present invention, it may be an advantage to include one or more ribosomal pause tag sequence(-s) between the protein coding sequences in the DNA immuno-therapy vaccine vector/plasmid herein in order to separate protein products.

An example is the viral "FMDV 2A tag" (Foot-and-mouth disease virus 2A tag). The translated amino acid sequence of FMDV 2A is APVKQTLNFDLLKLAGDVESNPGP— (SEQ ID NO: 15). FMDV 2A tag is capable of pausing and reinitiating the ribosome. The ratio of translated product before and after the FMDV 2A tag is close to 1:1 and the resulting protein products are normally completely separated. These types of ribosome tags have previously been used in connection with co-expression of two different domains, e.g. heavy chain and light chain in recombinant antibody production. However, the inventor of the present invention has made the surprising discovery that they are useful in connection with multi-cistronic DNA vaccines both for separation of flanking products and for control of the ratios of expressed proteins due to inherent efficiencies of ribosomal re-initiation. Sequence tags which favour a 1:1 ratio of translated products are herein preferably inserted between two protein encoding sequences that should preferably be produced in (or close to) a 1:1 ratio such as e.g. an insulin antigen and a potent cytokine such as e.g. TGF-β.

Another example of a ribosomal pause tag sequence herein is the viral sequence tag "TaV 2A" (*Thosea asigna* virus 2A—translated amino acid sequence of TaV 2A: RAEGRGSLLTCGDVEENPGP (SEQ ID NO: 16). The ratio of translated product before/upstream and after/downstream of this tag is reported to be 50:1 (or close to). The inventor of the present invention has made the surprising discovery that while this type of tag can be used to control expression levels in cases where it is vital that one translated product absolutely dominates another, the separation of flanking cytokine products is less than 50% relative to the sequences disclosed in literature and the expression ratio is thus about 10:6. In connection with the present invention, a 2A type of ribosomal pause tag sequence should preferably result in different expression levels of two proteins encoded by the same vector/plasmid. Expression of small amounts of a pleiotropic cytokine (such as IL-2) relative to an anti-inflammatory cytokine, such as IL-10, is desirable herein and fused products are not desirable.

A further example of a ribosomal pause tag amino acid sequence herein is the viral sequence "P 2A" (*Porcine teschovirus*-1 2A, ATNFSLLKQAGDVEENPGP—(SEQ ID NO: 17)). P 2A sequences function appropriately when inserted between IL-10 and IL-2 herein, resulting in near complete separation with an expression ratio of >5:1 between IL-10 and IL-2.

Alternatively, proteinase sensitive sequences, allowing for endogenous cleavage between plasmid expressed poly proteins, may be used herein. A furin sensitive sequence (recognizing RAKR (SEQ ID NO:33) motifs) or carboxypeptidase sensitive sequence (recognizing RRRR (SEQ ID NO:34), RKRR (SEQ ID NO:35), or RRKR (SEQ ID NO:36) motifs) may be used herein for separating protein products. However, the inventor of the present invention has made the surprising discovery that neither furin nor carboxypeptidase cleavage sequences result in separated products herein thus leading to secretion of undesired IL-10/IL-2 fusion proteins.

TGF-b/β/β1 (Transforming growth factor beta/β1): TGF-β is a secreted protein that controls proliferation, cellular differentiation, and other functions in most cells. TGF-β is a very potent cytokine with significant effects on cell fate and phenotype in a context-dependent manner, e.g. depending upon the other cytokine signals received contemporaneously. Endogenous TGF-β is produced in a latent form associated with the outer membrane surface of the producing cell and requires activation (e.g. by inflammatory macrophages expressing CD36 and plasmin proteinase) for maturation and release of the active form. In one embodiment, TGF-β herein is a modified form that is constitutively active. This is achieved by replacing the cysteines at positions 223 and 225 with amino acids incapable of forming disulfide bridges. For example, serine or valine are used to replace cysteines at positions 223 and 225. This results in an active pro-protein structure that is released into the local microenvironment.

```
Human endogenous TGF-β1 sequence-SEQ ID NO: 18:
MPPSGLRLLLLLLPLLWLLVLTPGRPAAGLSTCKTIDMELVKRKRIEAIR

GQILSKLRLASPPSQGEVPPGPLPEAVLALYNSTRDRVAGESAEPEPEPE

ADYYAKEVTRVLMVETHNEIYDKFKQSTHSIYMFFNTSELREAVPEPVLL

SRAELRLLRLKLKVEQHVELYQKYSNNSWRYLSNRLLAPSDSPEWLSFDV

TGVVRQWLSRGGEIEGFRLSAHCSCDSRDNTLQVDINGFTTGRRGDLATI

HGMNRPFLLLMATPLERAQHLQSSRHRRALDTNYCFSSTEKNCCVRQLYI

DFRKDLGWKWIHEPKGYHANFCLGPCPYIWSLDTQYSKVLALYNQHNPGA

SAAPCCVPQALEPLPIVYYVGRKPKVEQLSNMIVRSCKCS.

Modified human TGF-β1 sequence that is
constitutively active and secreted (substitutions
in relation to wt TGF-β1 shown with bold
and underline)-SEQ ID NO: 19:
MPPSGLRLLLLLLPLLWLLVLTPGRPAAGLSTCKTIDMELVKRKRIEAIR

GQILSKLRLASPPSQGEVPPGPLPEAVLALYNSTRDRVAGESAEPEPEPE

ADYYAKEVTRVLMVETHNEIYDKFKQSTHSIYMFFNTSELREAVPEPVLL

SRAELRLLRLKLKVEQHVELYQKYSNNSWRYLSNRLLAPSDSPEWLSFDV

TGVVRQWLSRGGEIEGFRLSAHVSVDSRDNTLQVDINGFTTGRRGDLATI

HGMNRPFLLLMATPLERAQHLQSSRHRRALDTNYCFSSTEKNCCVRQLYI

DFRKDLGWKWIHEPKGYHANFCLGPCPYIWSLDTQYSKVLALYNQHNPGA

SAAPCCVPQALEPLPIVYYVGRKPKVEQLSNMIVRSCKCS.

Another modified human TGF-β1 sequence that may
be used is SEQ ID NO: 25:
MPPSGLRLLLLLLPLLWLLVLTPGRPAAGLSTCKTIDMELVKRKRIEAIR

GQILSKLRLASPPSQGEVPPGPLPEAVLALYNSTRDRVAGESAEPEPEPE

ADYYAKEVTRVLMVETHNEIYDKFKQSTHSIYMFFNTSELREAVPEPVLL

SRAELRLLRLKLKVEQHVELYQKYSNNSWRYLSNRLLAPSDSPEWLSFDV

TGVVRQWLSRGGEIEGFRLSAHSSSDSRDNTLQVDINGFTTGRRGDLATI

HGMNRPFLLLMATPLERAQHLQSSRHRRALDTNYCFSSTEKNCCVRQLYI

DFRKDLGWKWIHEPKGYHANFCLGPCPYIWSLDTQYSKVLALYNQHNPGA

SAAPCCVPQALEPLPIVYYVGRKPKVEQLSNMIVRSCKCS.
```

Terminator sequence: a transcription terminator is a section of a nucleic acid sequence that marks the end of a gene during transcription. Release of the transcriptional complex frees RNA polymerase and related transcriptional machinery to begin transcription of new mRNAs. Additionally, the same cellular factors add a non-templated "poly-A tail" which significantly enhances the lifetime and functionality of the mRNA. An example of a suitable transcription terminator herein includes the "bGH_PA" terminator,

```
                                        (SEQ ID NO: 20)
CGACTGTGCCTTCTAGTTGCCAGCCATCTGTTGTTTGCCCCTCCCCCGTG

CCTTCCTTGACCCTGGAAGGTGCCACTCCCACTGTCCTTTCCTAATAAAA

TGAGGAAATTGCATCGCATTGTCTGAGTAGGTGTCATTCTATTCTGGGGG

GTGGGGTGGGGCAGGACAGCAAGGGGGAGGATTGGGAAGACAATAGCAGG

CATGCTGGGGATGCGGTGGGCTCTATGG.
```

Any acceptable terminator sequence may be utilized herein. Variations include use of two different flanking terminator sequences in the instance of bidirectional promoters producing two oppositely-oriented mRNAs.

In one embodiment the plasmid of the invention has the sequence as set out in SEQ ID NO: 24.

In a second embodiment the plasmid of the invention has the sequence SEQ ID NO: 26: full (non-annotated) plasmid sequence

```
GACTCTTCGCGATGTACGGGCCAGATATACGCGTTGACATTGATTATTGA

CTAGTTATTAATAGTAATCAATTACGGGGTCATTAGTTCATAGCCCATAT

ATGGAGTTCCGCGTTACATAACTTACGGTAAATGGCCCGCCTGGCTGACC

GCCCAACGACCCCCGCCCATTGACGTCAATAATGACGTATGTTCCCATAG

TAACGCCAATAGGGACTTTCCATTGACGTCAATGGGTGGACTATTTACGG

TAAACTGCCCACTTGGCAGTACATCAAGTGTATCATATGCCAAGTACGCC

CCCTATTGACGTCAATGACGGTAAATGGCCCGCCTGGCATTATGCCCAGT

ACATGACCTTATGGGACTTTCCTACTTGGCAGTACATCTACGTATTAGTC

ATCGCTATTACCATGGTGATGCGGTTTTGGCAGTACATCAATGGGCGTGG

ATAGCGGTTTGACTCACGGGGATTTCCAAGTCTCCACCCCATTGACGTCA

ATGGGAGTTTGTTTTGGCACCAAAATCAACGGGACTTTCCAAAATGTCGT

AACAACTCCGCCCCATTGACGCAAATGGGCGGTAGGCGTGTACGGTGGGA

GGTCTATATAAGCAGAGCTCTCTGGCTAACTAGAGAACCCACTGCTTACT

GGCTTATCGAAATTAATACGACTCACTATAGGGAGACCCAAGCTGGCTAG

CGTTTAAACTTAAGCTTGGTACCGAGCTCGGATCCACTAGTCCAGTGTGG

TGGAATTCTGCACTGCAGCTCGCATCTCTCCTTCACGCGCCCGCCGCCCT

ACCTGAGGCCGCCATCCACGCCGGTTGAGTCGCGTTCTGCCGCCTCCCGC

CTGTGGTGCCTCCTGAACTGCGTCCGCCGTCTAGGTAAGTTTAAAGCTCA

GGTCGAGACCGGGCCTTTGTCCGGCGCTCCCTTGGAGCCTACCTAGACTC
```

-continued

AGCCGGCTCTCCACGCTTTGCCTGACCCTGCTTGCTCAACTCTAGGTAAG
TTAATGAGACAGATAGAAACTGGTCTTGTAGAAACAGAGTAGTCGCCTGC
TTTTCTGCCAGGTGCTGACTTCTCTCCCCTGGGCTTTTTTCTTTTTCTCA
GGTTGAAAAGAAGAAGACGAAGAAGACGAAGAAGACAAACCGTCGTCGAC
TGCCATGCGCCGCTGATTAACGCCGCCACCATGGCCCACCGACGCAGATC
CAGAAGCTGCCGTGAGGACCAGAAGCCCGTGATGGATGATCAGAGGGACC
TTATCTCTAACAATGAACAACTGCCAATGCTCGGCAGACGGCCTGGGGCC
CCGGAGAGCAAGTGCAGCAGAGGAGCCTTGTACACGGGGTTCTCCATTTT
AGTGACTCTCCTTCTCGCCGGCCAAGCTACCACCGCCTACTTTCTGTACC
AACAGCAAGGCAGACTAGACAAACTGACAATCACAAGCCAGAACCTTCAG
CTGGAGTCTCTGCGGATGAAGCTGCCCGCTTTGTGGATGAGATTGCTTCC
TCTACTTGCTCTCCTGGCGCTCTGGGGACCTGACCCCGAGCAAGAGTTTG
TTAATCAGCACCTGTGTGGGAGTCATCTGGTGGAGGCACTCTATTTAGTG
TGCGGAGAGAGGGGCTTCTTCTACACTCCAAAGACCAGACGGGAGGCCGA
AGACCTTCAAGTGGGGCAAGTAGAACTGGGTGGCGGACCCGGTGCCGGGA
GCCTTCAGCCGCTCGCCCTGGAGGGCTCTCTTCAGAAACGCGGCATCGTG
GAGCAGTGTTGCACATCCATTTGCTCACTCTACCAGCTGGAGAACTACTG
CAACGGAAGCGGAGTGAAGCAGACGTTGAATTTTGATTTGTTGAAGTTGG
CGGGGGATGTGGAGAGCAATCCGGGGCCGATGCCCCCTAGTGGCCTCAGA
CTTTTGTTATTGTTATTACCGCTTTTATGGCTCTTGGTGCTGACACCGGG
CCGTCCGGCTGCTGGCTTGTCGACTTGTAAGACAATTGATATGGAATTGG
TGAAACGAAAACGGATTGAGGCCATCCGAGGACAGATTTTGAGCAAGCTG
CGGCTTGCCTCGCCACCCTCGCAAGGGGAAGTCCCACCCGGACCTCTACC
AGAAGCAGTCCTAGCGCTGTACAACAGTACAAGAGATAGAGTGGCCGGGG
AATCCGCAGAACCAGAGCCTGAGCCTGAAGCCGATTATTATGCAAAGGAA
GTGACTAGGGTCCTGATGGTCGAGACCCATAACGAAATCTACGACAAATT
CAAACAAAGTACCCACTCTATCTACATGTTCTTCAACACCAGTGAGCTAA
GAGAAGCCGTGCCCGAACCTGTGCTTCTTTCCCGCGCAGAACTCCGCCTC
TTGAGACTCAAATTGAAAGTTGAACAACACGTAGAGCTTTACCAGAAATA
CTCTAATAATTCATGGCGATATCTTTCTAATCGTCTCCTCGCCCCATCTG
ACAGCCCTGAATGGCTCTCCTTCGACGTTACGGGAGTTGTGCGCCAGTGG
CTCAGCAGAGGCGGAGAGATAGAGGGCTTTCGGCTGAGCGCACATAGCTC
TAGCGACTCAAGGGACAACACATTGCAAGTGGATATTAACGGTTTTACAA
CTGGACGGAGAGGGGACCTGGCGACCATCCACGGCATGAATAGACCTTTC
CTGCTGCTGATGGCTACTCCCCTGGAGAGGGCACAGCACTTACAGTCTTC
CAGACACCGGCGCGCCCTGGATACAAACTACTGCTTCAGCTCCACCGAAA
AGAACTGTTGCGTGCGGCAGCTGTACATTGACTTCAGAAAGGATCTGGGC
TGGAAGTGGATTCATGAGCCCAAGGGGTATCATGCCAACTTCTGTCTTGG
GCCATGCCCATACATCTGGTCACTGGATACCCAGTACTCCAAAGTTCTGG
CCTTGTACAATCAACACAACCCTGGAGCTTCCGCCGCTCCTTGCTGTGTG
CCCCAAGCCCTAGAGCCCCTGCCCATCGTTTATTATGTCGGACGCAAGCC

-continued

CAAAGTAGAACAGCTATCAAATATGATCGTGAGAAGCTGCAAGTGTAGCT
GATAAACGCGTCGAGCATGCATCTAGGGCGGCCAATTCCGCCCCTCTCCC
CCCCACCCCTCTCCCTCCCCCCCCCCCTAACGTTACTGGCCGAAGCCGCTT
GGAATAAGGCCGGTGTGCGTTTGTCTATATGTTATTTTCCACCATATTGC
CGTCTTTTGGCAATGTGAGGGCCCGGAAACCTGGCCCTGTCTTCTTGACG
AGCATTCCTAGGGGTCTTTCCCCTCTCGCCAAAGGAATGCAAGGTCTGTT
GAATGTCGTGAAGGAAGCAGTTCCTCTGGAAGCTTCTTGAAGACAAACAA
CGTCTGTAGCGACCCTTTGTAGACAGCGGAACCCCCCACCTGGCGATAGA
TGCCTCTGCGGCCAAAAGCCACGTGTATAAGATACACCTGCAAAGGCGGC
ACAACCCCAGTGCCACGTTGTGAGTTGGATAGTTGTGGAAAGAGTCAAAT
GGCTCTCCTCAAGCGTATTCAACAAGGGGCTGAAGGATGCCCAGAAGGTA
CCCCATTGTATGGGATCTGATCTGGGGCCTCGGTGCACATGCTTTACATG
TGTTTAGTCGAGGTTAAAAAACGTCTAGGCCCCCCGAACCACGGGGACGT
GGTTTTCCTTTGAAAAACACGATGATAATATGATGCACAGCTCAGCACTG
CTCTGTTGCCTGGTCCTCCTGACTGGGGTGAGGGCCAGCCCAGGCCAGGG
CACCCAGTCTGAGAACAGCTGCACCCACTTCCCAGGCAACCTGCCTAACA
TGCTTCGAGATCTCCGAGATGCCTTCAGCAGAGTGAAGACTTTCTTTCAA
ATGAAGGATCAGCTGGACAACTTGTTGTTAAAGGAGTCCTTGCTGGAGGA
CTTTAAGGGTTACCTGGGTTGCCAAGCCTTGTCTGAGATGATCCAGTTTT
ACCTGGAGGAGGTGATGCCCCAAGCTGAGAACCAAGACCCAGACATCAAG
GCGCATGTGAACTCCCTGGGGGAGAACCTGAAGACCCTCAGGCTGAGGCT
ACGGCGCTGTCATCGATTTCTTCCCTGTGAAAACAAGAGCAAGGCCGTGG
AGCAGGTGAAGAATGCCTTTAATAAGCTCCAAGAGAAAGGCATCTACAAA
GCCATGAGTGAGTTTGACATCTTCATCAACTACATAGAAGCCTACATGAC
AATGAAGATACGAAACGGGAGCGGCGCTACTAACTTCAGCCTGCTGAAGC
AGGCTGGAGACGTGGAGGAGAACCCTGGACCTATGTACAGAATGCAGCTG
CTGAGCTGCATCGCCCTGAGCCTGGCCCTGGTGACCAACAGCGCACCCAC
GTCCTCTAGCACCAAGAAGACCCAGTTACAGTTGGAGCATCTACTTTTAG
ACCTGCAAATGATTTTGAACGGCATCAACAACTACAAGAATCCTAAACTT
ACTCGCATGCTTACCTTCAAATTTTACATGCCCAAGAAGGCCACCGAACT
GAAGCACTTGCAATGTCTGGAGGAAGAACTCAAGCCGCTGGAGGAAGTTC
TCAACCTCGCGCAGTCCAAGAATTTCCACCTCCGGCCAAGAGACCTGATC
AGTAACATTAATGTGATAGTGCTGGAGCTGAAGGGAAGCGAGACTACATT
TATGTGCGAGTACGCCGATGAAACCGCTACAATCGTCGAGTTCCTGAATA
GATGGATCACATTTTGCCAGTCAATTATCTCTACTCTGACATGATAACTC
GAGGTCTAGAGGGCCCGTTTAAACCCGCTGATCAGCCTCGACTGTGCCTT
CTAGTTGCCAGCCATCTGTTGTTTGCCCCTCCCCCGTGCCTTCCTTGACC
CTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGC
AGGACAGCAAGGGGGAGGATTGGGAAGACAATAGCAGGCATGCTGGGGAT

```
GCGGTGGGCTCTATGGCTTCTACTGGGCGGTTTTATGGACAGCAAGCGAA
CCGGAATTGCCAGCTGGGGCGCCCTCTGGTAAGGTTGGGAAGCCCTGCAA
AGTAAACTGGATGGCTTTCTCGCCGCCAAGGATCTGATGGCGCAGGGGAT
CAAGCTCTGATCAAGAGACAGGATGAGGATCGTTTCGCATGGCCAAAGAA
GACAATATTGAAATGCAAGGTACCGTTCTTGAAACGTTGCCTAATACCAT
GTTCCGCGTAGAGTTAGAAAACGGTCACGTGGTTACTGCACACATCTCCG
GTAAAATGCGCAAAAACTACATCCGCATCCTGACGGGCGACAAAGTGACT
GTTGAACTGACCCCGTACGACCTGAGCAAAGGCCGCATTGTCTTCCGTAG
TCGCTGATAAATTATTAACGCTTACAATTTCCTGATGCGGTATTTTCTCC
TTACGCATCTGTGCGGTATTTCACACCGCATACAGGTGGCACTTTTCGGG
GAAATGTGCGCGGAACCCCTATTTGTTTATTTTTCTAAATACATTCAAAT
ATGTATCCGCTCATGAGACAATAACCCTGATAAATGCTTCAATAATAGCA
CGTGCTAAAACTTCATTTTTAATTTAAAAGGATCTAGGTGAAGATCCTTT
TTGATAATCTCATGACCAAAATCCCTTAACGTGAGTTTTCGTTCCACTGA
GCGTCAGACCCCGTAGAAAAGATCAAAGGATCTTCTTGAGATCCTTTTTT
TCTGCGCGTAATCTGCTGCTTGCAAACAAAAAAACCACCGCTACCAGCGG
TGGTTTGTTTGCCGGATCAAGAGCTACCAACTCTTTTTCCGAAGGTAACT
GGCTTCAGCAGAGCGCAGATACCAAATACTGTTCTTCTAGTGTAGCCGTA
GTTAGGCCACCACTTCAAGAACTCTGTAGCACCGCCTACATACCTCGCTC
TGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGG
CTGAACGGGGGGTTCGTGCACACAGCCCAGCTTGGAGCGAACGACCTACA
CCGAACTGAGATACCTACAGCGTGAGCTATGAGAAAGCGCCACGCTTCCC
GAAGGGAGAAAGGCGGACAGGTATCCGGTAAGCGGCAGGGTCGGAACAGG
AGAGCGCACGAGGGAGCTTCCAGGGGGAAACGCCTGGTATCTTTATAGTC
CTGTCGGGTTTCGCCACCTCTGACTTGAGCGTCGATTTTTGTGATGCTCG
TCAGGGGGGCGGAGCCTATGGAAAAACGCCAGCAACGCGGCCTTTTTACG
GTTCCTGGCTTTTGCTGGCCTTTTGCTCACATGTTCTT.
```

In a third embodiment the plasmid of the invention has the sequence SEQ ID NO: 28: full (non-annotated) plasmid sequence

```
GACTCTTCGCGATGTACGGGCCAGATATACGCGTTGACATTGATTATTGA
CTAGTTATTAATAGTAATCAATTACGGGGTCATTAGTTCATAGCCCATAT
ATGGAGTTCCGCGTTACATAACTTACGGTAAATGGCCCGCCTGGCTGACC
GCCCAACGACCCCCGCCCATTGACGTCAATAATGACGTATGTTCCCATAG
TAACGCCAATAGGGACTTTCCATTGACGTCAATGGGTGGACTATTTACGG
TAAACTGCCCACTTGGCAGTACATCAAGTGTATCATATGCCAAGTACGCC
CCCTATTGACGTCAATGACGGTAAATGGCCCGCCTGGCATTATGCCCAGT
ACATGACCTTATGGGACTTTCCTACTTGGCAGTACATCTACGTATTAGTC
ATCGCTATTACCATGGTGATGCGGTTTTGGCAGTACATCAATGGGCGTGG
ATAGCGGTTTGACTCACGGGGATTTCCAAGTCTCCACCCCATTGACGTCA
ATGGGAGTTTGTTTTGGCACCAAAATCAACGGGACTTTCCAAAATGTCGT
AACAACTCCGCCCCATTGACGCAAATGGGCGGTAGGCGTGTACGGTGGGA
GGTCTATATAAGCAGAGCTCTCTGGCTAACTAGAGAACCCACTGCTTACT
GGCTTATCGAAATTAATACGACTCACTATAGGGAGACCCAAGCTGGCTAG
CGTTTAAACTTAAGCTTGGTACCGAGCTCGGATCCACTAGTCCAGTGTGG
TGGAATTCTGCACTGCAGCTCGCATCTCTCCTTCACGCGCCCGCCGCCCT
ACCTGAGGCCGCCATCCACGCCGGTTGAGTCGCGTTCTGCCGCCTCCCGC
CTGTGGTGCCTCCTGAACTGCGTCCGCCGTCTAGGTAAGTTTAAAGCTCA
GGTCGAGACCGGGCCTTTGTCCGGCGCTCCCTTGGAGCCTACCTAGACTC
AGCCGGCTCTCCACGCTTTGCCTGACCCTGCTTGCTCAACTCTAGGTAAG
TTAATGAGACAGATAGAAACTGGTCTTGTAGAAACAGAGTAGTCGCCTGC
TTTTCTGCCAGGTGCTGACTTCTCTCCCCTGGGCTTTTTCTTTTTCTCA
GGTTGAAAAGAAGAAGACGAAGAAGACGAAGAAGACAAACCGTCGTCGAC
TGCCATGCGCCGCTGATTAACGCCGCCACCATGGCCCACCGACGCAGATC
CAGAAGCTGCCGTGAGGACCAGAAGCCCGTGATGGATGATCAGAGGGACC
TTATCTCTAACAATGAACAACTGCCAATGCTCGGCAGACGGCCTGGGGCC
CCGGAGAGCAAGTGCAGCAGAGGAGCCTTGTACACGGGGTTCTCCATTTT
AGTGACTCTCCTTCTCGCCGGCCAAGCTACCACCGCCTACTTTCTGTACC
AACAGCAAGGCAGACTAGACAAACTGACAATCACAAGCCAGAACCTTCAG
CTGGAGTCTCTGCGGATGAAGCTGCCCGCTTTGTGGATGAGATTGCTTCC
TCTACTTGCTCTCCTGGCGCTCTGGGGACCTGACCCCGAGCAAGAGTTTG
TTAATCAGCACCTGTGTGGGAGTCATCTGGTGGAGGCACTCTATTTAGTG
TGCGGAGAGAGGGGCTTCTTCTACACTCCAAAGACCAGACGGGAGGCCGA
AGACCTTCAAGTGGGGCAAGTAGAACTGGGTGGCGGACCCGGTGCCGGGA
GCCTTCAGCCGCTCGCCCTGGAGGGCTCTCTTCAGAAACGCGGCATCGTG
GAGCAGTGTTGCACATCCATTTGCTCACTCTACCAGCTGGAGAACTACTG
CAACGGAAGCGGAGTGAAGCAGACGTTGAATTTTGATTTGTTGAAGTTGG
CGGGGGATGTGGAGAGCAATCCGGGGCCGATGCCCCCTAGTGGCCTCAGA
CTTTTGTTATTGTTATTACCGCTTTTATGGCTCTTGGTGCTGACACCGGG
CCGTCCGGCTGCTGGCTTGTCGACTTGTAAGACAATTGATATGGAATTGG
TGAAACGAAAACGGATTGAGGCCATCCGAGGACAGATTTTGAGCAAGCTG
CGGCTTGCCTCGCCACCCTCGCAAGGGGAAGTCCCACCCGGACCTCTACC
AGAAGCAGTCCTAGCGCTGTACAACAGTACAAGAGATAGAGTGGCCGGGG
AATCCGCAGAACCAGAGCCTGAGCCTGAAGCCGATTATTATGCAAAGGAA
GTGACTAGGGTCCTGATGGTCGAGACCCATAACGAAATCTACGACAAATT
CAAACAAAGTACCCACTCTATCTACATGTTCTTCAACACCAGTGAGCTAA
GAGAAGCCGTGCCCGAACCTGTGCTTCTTTCCCGCGCAGAACTCCGCCTC
TTGAGACTCAAATTGAAAGTTGAACAACACGTAGAGCTTTACCAGAAATA
CTCTAATAATTCATGGCGATATCTTTCTAATCGTCTCCTCGCCCCATCTG
ACAGCCCTGAATGGCTCTCCTTCGACGTTACGGGAGTTGTGCGCCAGTGG
```

```
CTCAGCAGAGGCGGAGAGATAGAGGGCTTTCGGCTGAGCGCACATAGCTC
TAGCGACTCAAGGGACAACACATTGCAAGTGGATATTAACGGTTTTACAA
CTGGACGGAGAGGGGACCTGGCGACCATCCACGGCATGAATAGACCTTTC
CTGCTGCTGATGGCTACTCCCCTGGAGAGGGCACAGCACTTACAGTCTTC
CAGACACCGGCGCGCCCTGGATACAAACTACTGCTTCAGCTCCACCGAAA
AGAACTGTTGCGTGCGGCAGCTGTACATTGACTTCAGAAAGGATCTGGGC
TGGAAGTGGATTCATGAGCCCAAGGGGTATCATGCCAACTTCTGTCTTGG
GCCATGCCCATACATCTGGTCACTGGATACCCAGTACTCCAAAGTTCTGG
CCTTGTACAATCAACACAACCCTGGAGCTTCCGCCGCTCCTTGCTGTGTG
CCCCAAGCCCTAGAGCCCCTGCCCATCGTTTATTATGTCGGACGCAAGCC
CAAAGTAGAACAGCTATCAAATATGATCGTGAGAAGCTGCAAGTGTAGCT
GATAAACGCGTCGAGCATGCATCTAGGGCGGCCAATTCCGCCCCTCTCCC
CCCCACCCCTCTCCCTCCCCCCCCCCTAACGTTACTGGCCGAAGCCGCTT
GGAATAAGGCCGGTGTGCGTTTGTCTATATGTTATTTTCCACCATATTGC
CGTCTTTTGGCAATGTGAGGGCCCGGAAACCTGGCCCTGTCTTCTTGACG
AGCATTCCTAGGGGTCTTTCCCCTCTCGCCAAAGGAATGCAAGGTCTGTT
GAATGTCGTGAAGGAAGCAGTTCCTCTGGAAGCTTCTTGAAGACAAACAA
CGTCTGTAGCGACCCTTTGTAGACAGCGGAACCCCCCACCTGGCGATAGA
TGCCTCTGCGGCCAAAAGCCACGTGTATAAGATACACCTGCAAAGGCGGC
ACAACCCCAGTGCCACGTTGTGAGTTGGATAGTTGTGGAAAGAGTCAAAT
GGCTCTCCTCAAGCGTATTCAACAAGGGGCTGAAGGATGCCCAGAAGGTA
CCCCATTGTATGGGATCTGATCTGGGGCCTCGGTGCACATGCTTTACATG
TGTTTAGTCGAGGTTAAAAAACGTCTAGGCCCCCCGAACCACGGGGACGT
GGTTTTCCTTTGAAAAACACGATGATAATATGATGCACAGCTCAGCACTG
CTCTGTTGCCTGGTCCTCCTGACTGGGGTGAGGGCCAGCCCAGGCCAGGG
CACCCAGTCTGAGAACAGCTGCACCCACTTCCCAGGCAACCTGCCTAACA
TGCTTCGAGATCTCCGAGATGCCTTCAGCAGAGTGAAGACTTTCTTTCAA
ATGAAGGATCAGCTGGACAACTTGTTGTTAAAGGAGTCCTTGCTGGAGGA
CTTTAAGGGTTACCTGGGTTGCCAAGCCTTGTCTGAGATGATCCAGTTTT
ACCTGGAGGAGGTGATGCCCCAAGCTGAGAACCAAGACCCAGACATCAAG
GCGCATGTGAACTCCCTGGGGGAGAACCTGAAGACCCTCAGGCTGAGGCT
ACGGCGCTGTCATCGATTTCTTCCCTGTGAAAACAAGAGCAAGGCCGTGG
AGCAGGTGAAGAATGCCTTTAATAAGCTCCAAGAGAAAGGCATCTACAAA
GCCATGAGTGAGTTTGACATCTTCATCAACTACATAGAAGCCTACATGAC
AATGAAGATACGAAACGGGAGCGGCGCTACTAACTTCAGCCTGCTGAAGC
AGGCTGGAGACGTGGAGGAGAACCCTGGACCTATGTACAGAATGCAGCTG
CTGAGCTGCATCGCCCTGAGCCTGGCCCTGGTGACCAACAGCGCACCCAC
GTCCTCTAGCACCAAGAAGACCCAGTTACAGTTGGAGCATCTACTTTTAG
ACCTGCAAATGATTTTGAACGGCATCAACAACTACAAGAATCCTAAACTT
ACTCGCATGCTTACCTTCAAATTTTACATGCCCAAGAAGGCCACCGAACT
GAAGCACTTGCAATGTCTGGAGGAAGAACTCAAGCCGCTGGAGGAAGTTC
TCAACCTCGCGCAGTCCAAGAATTTCCACCTCCGGCCAAGAGACCTGATC
AGTAACATTAATGTGATAGTGCTGGAGCTGAAGGGAAGCGAGACTACATT
TATGTGCGAGTACGCCGATGAAACCGCTACAATCGTCGAGTTCCTGAATA
GATGGATCACATTTTGCCAGTCAATTATCTCTACTCTGACATGATAACTC
GAGGTCTAGAGGGCCCGTTTAAACCCGCTGATCAGCCTCGACTGTGCCTT
CTAGTTGCCAGCCATCTGTTGTTTGCCCCTCCCCCGTGCCTTCCTTGACC
CTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGC
AGGACAGCAAGGGGGAGGATTGGGAAGACAATAGCAGGCATGCTGGGGAT
GCGGTGGGCTCTATGGCTTCTACTGGGCGGTTTTATGGACAGCAAGCGAA
CCGGAATTGCCAGCTGGGGCGCCCTCTGGTAAGGTTGGGAAGCCCTGCAA
AGTAAACTGGATGGCTTTCTCGCCGCCAAGGATCTGATGGCGCAGGGGAT
CAAGCTCTGATCAAGAGACAGGATGAGGATCGTTTCGCATGGCAAAGAA
GACAATATTGAAATGCAAGGTACCGTTCTTGAAACGTTGCCTAATACCAT
GTTCCGCGTAGAGTTAGAAAACGGTCACGTGGTTACTGCACACATCTCCG
GTAAAATGCGCAAAAACTACATCCGCATCCTGACGGGCGACAAAGTGACT
GTTGAACTGACCCCGTACGACCTGAGCAAAGGCCGCATTGTCTTCCGTAG
TCGCTGATAAATTATTAACGCTTACAATTTCCTGATGCGGTATTTTCTCC
TTACGCATCTGTGCGGTATTTCACACCGCATACAGGTGGCACTTTTCGGG
GAAATGTGCGCGGAACCCCTATTTGTTTATTTTTCTAAATACATTCAAAT
ATGTATCCGCTCATGAGACAATAACCCTGATAAATGCTTCAATAATAGCA
CGTGCTAAAACTTCATTTTTAATTTAAAAGGATCTAGGTGAAGATCCTTT
TTGATAATCTCATGACCAAAATCCCTTAACGTGAGTTTTCGTTCCACTGA
GCGTCAGACCCCGTAGAAAAGATCAAAGGATCTTCTTGAGATCCTTTTTT
TCTGCGCGTAATCTGCTGCTTGCAAACAAAAAAACCACCGCTACCAGCGG
TGGTTTGTTTGCCGGATCAAGAGCTACCAACTCTTTTTCCGAAGGTAACT
GGCTTCAGCAGAGCGCAGATACCAAATACTGTTCTTCTAGTGTAGCCGTA
GTTAGGCCACCACTTCAAGAACTCTGTAGCACCGCCTACATACCTCGCTC
TGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGG
CTGAACGGGGGGTTCGTGCACACAGCCCAGCTTGGAGCGAACGACCTACA
CCGAACTGAGATACCTACAGCGTGAGCTATGAGAAAGCGCCACGCTTCCC
GAAGGGAGAAAGGCGGACAGGTATCCGGTAAGCGGCAGGGTCGGAACAGG
AGAGCGCACGAGGGAGCTTCCAGGGGGAAACGCCTGGTATCTTTATAGTC
CTGTCGGGTTTCGCCACCTCTGACTTGAGCGTCGATTTTTGTGATGCTCG
TCAGGGGGGCGGAGCCTATGGAAAAACGCCAGCAACGCGGCCTTTTTACG
GTTCCTGGCCTTTTGCTGGCCTTTTGCTCACATGTTCTT.
```

In a fourth embodiment the plasmid of the invention has the sequence SEQ ID NO: 29: full (non-annotated) plasmid sequence GACTCTTCGCGATGTACGGGCCAGATATACGCGTTGACATTGATTATTGA
CTAGTTATTAATAGTAATCAATTACGGGGTCATTAGTTCATAGCCCATAT
ATGGAGTTCCGCGTTACATAACTTACGGTAAATGGCCCGCCTGGCTGACC
GCCCAACGACCCCCGCCCATTGACGTCAATAATGACGTATGTTCCCATAG
TAACGCCAATAGGGACTTTCCATTGACGTCAATGGGTGGACTATTTACGG
TAAACTGCCCACTTGGCAGTACATCAAGTGTATCATATGCCAAGTACGCC
CCCTATTGACGTCAATGACGGTAAATGGCCCGCCTGGCATTATGCCCAGT
ACATGACCTTATGGGACTTTCCTACTTGGCAGTACATCTACGTATTAGTC
ATCGCTATTACCATGGTGATGCGGTTTTGGCAGTACATCAATGGGCGTGG
ATAGCGGTTTGACTCACGGGGATTTCCAAGTCTCCACCCCATTGACGTCA
ATGGGAGTTTGTTTTGGCACCAAAATCAACGGGACTTTCCAAAATGTCGT
AACAACTCCGCCCCATTGACGCAAATGGGCGGTAGGCGTGTACGGTGGGA
GGTCTATATAAGCAGAGCTCTCTGGCTAACTAGAGAACCCACTGCTTACT
GGCTTATCGAAATTAATACGACTCACTATAGGGAGACCCAAGCTGGCTAG
CGTTTAAACTTAAGCTTGGTACCGAGCTCGGATCCACTAGTCCAGTGTGG
TGGAATTCTGCAGCTCGCATCTCTCCTTCACGCGCCCGCCGCCCTACCTG
AGGCCGCCATCCACGCCGGTTGAGTCGCGTTCTGCCGCCTCCCGCCTGTG
GTGCCTCCTGAACTGCGTCCGCCGTCTAGGTAAGTTTAAAGCTCAGGTCG
AGACCGGGCCTTTGTCCGGCGCTCCCTTGGAGCCTACCTAGACTCAGCCG
GCTCTCCACGCTTTGCCTGACCCTGCTTGCTCAACTCTAGGTAAGTTAAT
GAGACAGATAGAAACTGGTCTTGTAGAAACAGAGTAGTCGCCTGCTTTTC
TGCCAGGTGCTGACTTCTCTCCCCTGGGCTTTTTTCTTTTTCTCAGGTTG
AAAAGAAGAAGACGAAGAAGACGAAGAAGACAAACCGTCGTCGACTGCCA
TGCGCCGCTGATTAACGCCGCCACCATGGCCCACCGACGCAGATCCAGAA
GCTGCCGTGAGGACCAGAAGCCCGTGATGGATGATCAGAGGGACCTTATC
TCTAACAATGAACAACTGCCAATGCTCGGCAGACGGCCTGGGGCCCCGGA
GAGCAAGTGCAGCAGAGGAGCCTTGTACACGGGGTTCTCCATTTTAGTGA
CTCTCCTTCTCGCCGGCCAAGCTACCACCGCCTACTTTCTGTACCAACAG
CAAGGCAGACTAGACAAACTGACAATCACAAGCCAGAACCTTCAGCTGGA
GTCTCTGCGGATGAAGCTGCCCGCTTTGTGGATGAGATTGCTTCCTCTAC
TTGCTCTCCTGGCGCTCTGGGGACCTGACCCCGAGCAAGAGTTTGTTAAT
CAGCACCTGTGTGGGAGTCATCTGGTGGAGGCACTCTATTTAGTGTGCGG
AGAGAGGGGCTTCTTCTACACTCCAAAGACCAGACGGGAGGCCGAAGACC
TTCAAGTGGGGCAAGTAGAACTGGGTGGCGGACCCGGTGCCGGGAGCCTT
CAGCCGCTCGCCCTGGAGGGCTCTCTTCAGAAACGCGGCATCGTGGAGCA
GTGTTGCACATCCATTTGCTCACTCTACCAGCTGGAGAACTACTGCAACG
GAAGCGGAGTGAAGCAGACGTTGAATTTTGATTTGTTGAAGTTGGCGGGG
GATGTGGAGAGCAATCCGGGGCCGATGCCCCTAGTGGCCTCAGACTTTT GTTATTGTTATTACCGCTTTTATGGCTCTTGGTGCTGACACCGGGCCGTC
CGGCTGCTGGCTTGTCGACTTGTAAGACAATTGATATGGAATTGGTGAAA
CGAAAACGGATTGAGGCCATCCGAGGACAGATTTTGAGCAAGCTGCGGCT
TGCCTCGCCACCCTCGCAAGGGGAAGTCCCACCCGGACCTCTACCAGAAG
CAGTCCTAGCGCTGTACAACAGTACAAGAGATAGAGTGGCCGGGGAATCC
GCAGAACCAGAGCCTGAGCCTGAAGCCGATTATTATGCAAAGGAAGTGAC
TAGGGTCCTGATGGTCGAGACCCATAACGAAATCTACGACAAATTCAAAC
AAAGTACCCACTCTATCTACATGTTCTTCAACACCAGTGAGCTAAGAGAA
GCCGTGCCCGAACCTGTGCTTCTTTCCCGCGCAGAACTCCGCCTCTTGAG
ACTCAAATTGAAAGTTGAACAACACGTAGAGCTTTACCAGAAATACTCTA
ATAATTCATGGCGATATCTTTCTAATCGTCTCCTCGCCCCATCTGACAGC
CCTGAATGGCTCTCCTTCGACGTTACGGGAGTTGTGCGCCAGTGGCTCAG
CAGAGGCGGAGAGATAGAGGGCTTTCGGCTGAGCGCACATAGCTCTAGCG
ACTCAAGGGACAACACATTGCAAGTGGATATTAACGGTTTTACAACTGGA
CGGAGAGGGGACCTGGCGACCATCCACGGCATGAATAGACCTTTCCTGCT
GCTGATGGCTACTCCCCTGGAGAGGGCACAGCACTTACAGTCTTCCAGAC
ACCGGCGCGCCCTGGATACAAACTACTGCTTCAGCTCCACCGAAAAGAAC
TGTTGCGTGCGGCAGCTGTACATTGACTTCAGAAAGGATCTGGGCTGGAA
GTGGATTCATGAGCCCAAGGGGTATCATGCCAACTTCTGTCTTGGGCCAT
GCCCATACATCTGGTCACTGGATACCCAGTACTCCAAAGTTCTGGCCTTG
TACAATCAACACAACCCTGGAGCTTCCGCCGCTCCTTGCTGTGTGCCCCA
AGCCCTAGAGCCCCTGCCCATCGTTTATTATGTCGGACGCAAGCCCAAAG
TAGAACAGCTATCAAATATGATCGTGAGAAGCTGCAAGTGTAGCTGATAA
ACGCGTCGAGCATGCATCTAGGGCGGCCAATTCCGCCCCTCTCCCCCCCA
CCCCTCTCCCTCCCCCCCCCCTAACGTTACTGGCCGAAGCCGCTTGGAAT
AAGGCCGGTGTGCGTTTGTCTATATGTTATTTTCCACCATATTGCCGTCT
TTTGGCAATGTGAGGGCCCGGAAACCTGGCCCTGTCTTCTTGACGAGCAT
TCCTAGGGGTCTTTCCCCTCTCGCCAAAGGAATGCAAGGTCTGTTGAATG
TCGTGAAGGAAGCAGTTCCTCTGGAAGCTTCTTGAAGACAAACAACGTCT
GTAGCGACCCTTTGTAGACAGCGGAACCCCCCACCTGGCGATAGATGCCT
CTGCGGCCAAAAGCCACGTGTATAAGATACACCTGCAAAGGCGGCACAAC
CCCAGTGCCACGTTGTGAGTTGGATAGTTGTGGAAAGAGTCAAATGGCTC
TCCTCAAGCGTATTCAACAAGGGGCTGAAGGATGCCCAGAAGGTACCCCA
TTGTATGGGATCTGATCTGGGGCCTCGGTGCACATGCTTTACATGTGTTT
AGTCGAGGTTAAAAAACGTCTAGGCCCCCGAACCACGGGGACGTGGTTT
TCCTTTGAAAAACACGATGATAATATGATGCACAGCTCAGCACTGCTCTG
TTGCCTGGTCCTCCTGACTGGGGTGAGGGCCAGCCCAGGCCAGGGCACCC
AGTCTGAGAACAGCTGCACCCACTTCCCAGGCAACCTGCCTAACATGCTT
CGAGATCTCCGAGATGCCTTCAGCAGAGTGAAGACTTTCTTTCAAATGAA
GGATCAGCTGGACAACTTGTTGTTAAAGGAGTCCTTGCTGGAGGACTTTA
AGGGTTACCTGGGTTGCCAAGCCTTTGTCTGAGATGATCCAGTTTTACCTG

```
GAGGAGGTGATGCCCCAAGCTGAGAACCAAGACCCAGACATCAAGGCGCA

TGTGAACTCCCTGGGGGAGAACCTGAAGACCCTCAGGCTGAGGCTACGGC

GCTGTCATCGATTTCTTCCCTGTGAAAACAAGAGCAAGGCCGTGGAGCAG

GTGAAGAATGCCTTTAATAAGCTCCAAGAGAAAGGCATCTACAAAGCCAT

GAGTGAGTTTGACATCTTCATCAACTACATAGAAGCCTACATGACAATGA

AGATACGAAACGGGAGCGGCGCTACTAACTTCAGCCTGCTGAAGCAGGCT

GGAGACGTGGAGGAGAACCCTGGACCTATGTACAGAATGCAGCTGCTGAG

CTGCATCGCCCTGAGCCTGGCCCTGGTGACCAACAGCGCACCCACGTCCT

CTAGCACCAAGAAGACCCAGTTACAGTTGGAGCATCTACTTTTAGACCTG

CAAATGATTTTGAACGGCATCAACAACTACAAGAATCCTAAACTTACTCG

CATGCTTACCTTCAAATTTTACATGCCCAAGAAGGCCACCGAACTGAAGC

ACTTGCAATGTCTGGAGGAAGAACTCAAGCCGCTGGAGGAAGTTCTCAAC

CTCGCGCAGTCCAAGAATTTCCACCTCCGGCCAAGAGACCTGATCAGTAA

CATTAATGTGATAGTGCTGGAGCTGAAGGGAAGCGAGACTACATTTATGT

GCGAGTACGCCGATGAAACCGCTACAATCGTCGAGTTCCTGAATAGATGG

ATCACATTTTGCCAGTCAATTATCTCTACTCTGACATGATAACTCGAGTC

TAGAGGGCCCGTTTAAACCCGCTGATCAGCCTCGACTGTGCCTTCTAGTT

GCCAGCCATCTGTTGTTTGCCCCTCCCCCGTGCCTTCCTTGACCCTGGAA

GGTGCCACTCCCACTGTCCTTTCCTAATAAAATGAGGAAATTGCATCGCA

TTGTCTGAGTAGGTGTCATTCTATTCTGGGGGGTGGGGTGGGGCAGGACA

GCAAGGGGGAGGATTGGGAAGACAATAGCAGGCATGCTGGGGATGCGGTG

GGCTCTATGGCTTCTACTGGGCGGTTTTATGGACAGCAAGCGAACCGGAA

TTGCCAGCTGGGGCGCCCTCTGGTAAGGTTGGGAAGCCCTGCAAAGTAAA

CTGGATGGCTTTCTCGCCGCCAAGGATCTGATGGCGCAGGGGATCAAGCT

CTGATCAAGAGACAGGATGAGGATCGTTTCGCATGGCCAAAGAAGACAAT

ATTGAAATGCAAGGTACCGTTCTTGAAACGTTGCCTAATACCATGTTCCG

CGTAGAGTTAGAAAACGGTCACGTGGTTACTGCACACATCTCCGGTAAAA

TGCGCAAAAACTACATCCGCATCCTGACGGGCGACAAAGTGACTGTTGAA

CTGACCCCGTACGACCTGAGCAAAGGCCGCATTGTCTTCCGTAGTCGCTG

ATAAATTATTAACGCTTACAATTTCCTGATGCGGTATTTTCTCCTTACGC

ATCTGTGCGGTATTTCACACCGCATACAGGTGGCACTTTTCGGGGAAATG

TGCGCGGAACCCCTATTTGTTTATTTTTCTAAATACATTCAAATATGTAT

CCGCTCATGAGACAATAACCCTGATAAATGCTTCAATAATAGCACGTGCT

AAAACTTCATTTTTAATTTAAAAGGATCTAGGTGAAGATCCTTTTTGATA

ATCTCATGACCAAAATCCCTTAACGTGAGTTTTCGTTCCACTGAGCGTCA

GACCCCGTAGAAAGATCAAAGGATCTTCTTGAGATCCTTTTTTTCTGCG

CGTAATCTGCTGCTTGCAAACAAAAAAACCACCGCTACCAGCGGTGGTTT

GTTTGCCGGATCAAGAGCTACCAACTCTTTTTCCGAAGGTAACTGGCTTC

AGCAGAGCGCAGATACCAAATACTGTTCTTCTAGTGTAGCCGTAGTTAGG

CCACCACTTCAAGAACTCTGTAGCACCGCCTACATACCTCGCTCTGCTAA

TCCTGTTACCAGTGGCTGCTGCCAGTGGCGATAAGTCGTGTCTTACCGGG

TTGGACTCAAGACGATAGTTACCGGATAAGGCGCAGCGGTCGGGCTGAAC

GGGGGGTTCGTGCACACAGCCCAGCTTGGAGCGAACGACCTACACCGAAC

TGAGATACCTACAGCGTGAGCTATGAGAAAGCGCCACGCTTCCCGAAGGG

AGAAAGGCGGACAGGTATCCGGTAAGCGGCAGGGTCGGAACAGGAGAGCG

CACGAGGGAGCTTCCAGGGGGAAACGCCTGGTATCTTTATAGTCCTGTCG

GGTTTCGCCACCTCTGACTTGAGCGTCGATTTTTGTGATGCTCGTCAGGG

GGGCGGAGCCTATGGAAAAACGCCAGCAACGCGGCCTTTTTACGGTTCCT

GGGCTTTTGCTGGCCTTTTGCTCACATGTTCTT
```

The term "GLP-1/GLP-1 peptide/GLP-1R agonist peptide" as used herein refers to GLP-1 (Glucagon-like peptide-1) molecules/peptides/proteins/variants/agonists herein are molecules having GLP-1R (Glucagon-like peptide-1 receptor) agonist function meaning that they are agonists of the GLP-1 receptor. This class of drugs is normally used for the treatment of diabetes, in particular type 2 diabetes. The amino acid sequence of mature "human GLP-1" is: HAEGTFTSDVSSYLEGQAAKEFIAWLVKGRG (SEQ ID NO: 21).

The term "GLP-1 analogue" as used herein refers to a peptide or a compound, which is a variant of GLP-1 (SEQ ID NO: 15). The terms "GLP-1 analog" and "analogue" may be used interchangeably herein.

GLP-1 analogues may be described by reference to i) the number of the amino acid residue in human GLP-1 (SEQ ID NO: 15) which corresponds to the amino acid residue which is modified (i.e. the corresponding position in GLP-1 (SEQ ID NO: 15)), and to ii) the actual modification.

The term GLP-1 Derivatives refer to derivatives of GLP-1 analogues. The term "derivative" as used herein in the context of a GLP-1 analogue means a chemically modified GLP-1 analogue in which one or more substituents have been covalently attached to the GLP-1 analogue. The term "substituent" as used herein, means a chemical moiety or group/side group conjugated to the GLP-1 protein/agonist/analogue. The derivative may comprise one or more modifications selected from amides, carbohydrates, alkyl groups, acyl groups, esters and the like.

In some embodiments the substituent is covalently attached via an amino acid residue in said polypeptide e.g. at one of the amino acid positions selected from the group consisting of position 22, 23, 27, 34, 35, and 36.

In some embodiments the GLP-1 derivative comprises a substituent comprising a lipophilic moiety. The term "lipophilic moiety" as used herein, means an aliphatic or cyclic hydrocarbon moiety with more than 6 and less than 30 carbon atoms, wherein said hydrocarbon moiety may comprise additional substituents.

Examples of GLP-1 agonists include (but are not limited to) exenatide, liraglutide, lixisentide, albiglutide, dulaglutide, taspoglutide, and semaglutide. DNA immunotherapy vaccines using the plasmids herein may be combined initially with a parallel GLP-1R agonist treatment in treatment of e.g. recent onset T1D patients. GLP-1 co-administration may be chronic or temporary and include oral routes in addition to parenteral routes.

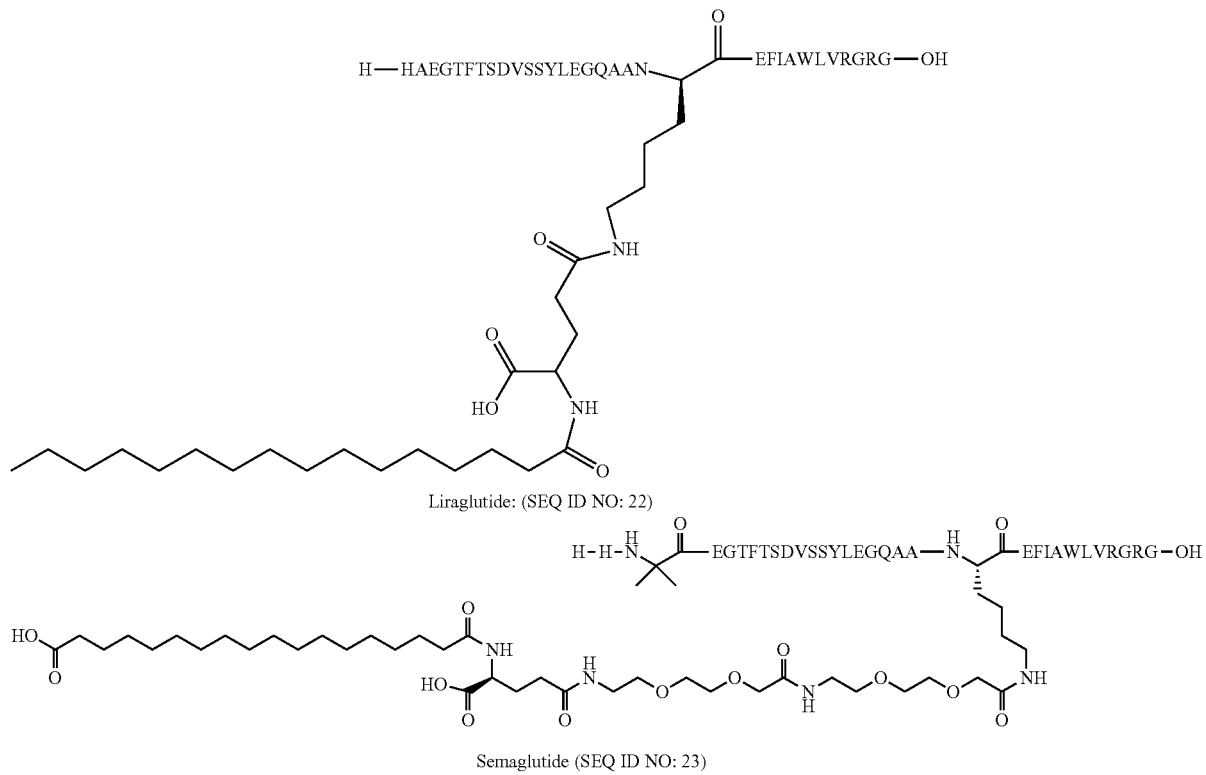

Liraglutide: (SEQ ID NO: 22)

Semaglutide (SEQ ID NO: 23)

Pharmaceutical compositions herein are preferably aqueous formulations comprising at least 50% water, more preferably at least 60% water, more preferably at least 75% water, more preferably at least 90% water, more preferably at least 95% water, and most preferably at least 99% water. The pharmaceutical compositions herein may alternatively be dry formulations, such as lyophilized formulations, intended for reconstitution, inhalation, intranasal instillation, intradermal administration, etc.

Pharmaceutical formulations herein are preferably administered without the use of methods for enhancing transformation, such as electroporation. In one embodiment, pharmaceutical formulations are intended for parenteral administration, e.g. subcutaneous administration, intradermal administration, intravenous administration, intramuscular administration, etc. In another embodiment, pharmaceutical compositions herein may furthermore be administered topically, orally, rectally, or by inhalation.

Pharmaceutical compositions herein are preferably without addition of any condensation agents or other excipients that may induce local reactions. Formulations herein preferably contain free-radical scavengers (e.g. 1% ethanol) and/or chelators such as e.g. divalent cation scavengers (e.g. EDTA [CAS #60-00-4], EGTA [CAS #67-42-5], or DPTA [CAS #67-43-6]) in order to enhance stability of aqueous plasmid DNA. Pharmaceutical compositions herein may furthermore be in the form of a saline solution and/or a buffer solution or comprise a saline solution and/or comprise a buffer solution (e.g. PBS—phosphate buffered saline, TRIS buffer, or equivalent pharmaceutically acceptable buffers). Pharmaceutical formulations herein are preferably free from any adjuvants as well other typical vaccine ingredients such as e.g. aluminium hydroxide, phenol, sorbitol, silicone, etc.

Administration: The DNA immuno-therapy vaccine herein may be administered to a T1D patient, or a patient in risk of developing T1D. The vaccine may be administered e.g on a daily basis, every second day, twice a week, once a week, twice monthly, once a month, every second month, four times a year, or once a year—frequency may be adjusted according to general or individual needs. The immuno-therapy herein may be chronic. The duration of therapy may be e.g. one month, two months, three months, 6 months, one year, two years, three years, five years, six years, seven years, eight years, nine years, or 10 years.

Embodiments

The following embodiments illustrate the invention and are not to be understood in any limiting way. It is understood that all embodiments can be combined in all possible ways.
 1. A plasmid which encodes:
  i. an antigen;
  ii. TGF-β; and
  iii. IL-10.
 2. The plasmid according to embodiment 1, which said antigen is an insulin antigen.
 3. A plasmid which co-expresses/encodes (preferably from a single operon): (i) an antigen, such as e.g. an insulin antigen; (ii) TGF-β/TGF-β1 (such as in a constitutively active form); and (iii) IL-10.
 4. The plasmid according to any of the preceding embodiments, wherein said insulin antigen is selected from the group consisting of: proinsulin, secretion-incapable preproinsulin, or a functional or immuno-dominant peptide fragment thereof.
 5. The plasmid according to any of the preceding embodiments, wherein said insulin antigen is selected from the group consisting of: proinsulin, pre-proinsulin, and a functional or immuno-dominant peptide fragment thereof.

6. The plasmid according to any of the preceding embodiments, wherein said insulin antigen is endosomally targeted insulin.

7. The plasmid according to any of the preceding embodiments, wherein said plasmid expresses the insulin antigen and TGF-β in a ratio of about 1:1.

8. The plasmid according to any of the preceding embodiments, wherein said plasmid expresses insulin antigen and TGF-β in an amount of at least 200 fold lower than IL-10.

9. The plasmid according to any of the preceding embodiments, wherein said plasmid expresses insulin antigen and TGF-β in an amount of at least 2 fold lower than IL-10.

10. The plasmid according to any of the preceding embodiments, wherein said plasmid furthermore co-expresses Interleukin-2 (IL-2).

11. The plasmid according to any of the preceding embodiments, wherein said plasmid expresses an excess of IL-10 and IL-2 over the antigen (e.g. insulin) and TGF-β.

12. The plasmid according to any of the preceding embodiments, wherein said plasmid expresses IL-10 and IL-2 at least about one fold, two fold, five fold or at least about one hundred fold over TGF-β and insulin antigen (ratio of IL-10+IL-2 to insulin+TGF-β may be at least 1:1, or 2:1, or 5:1 or 100:1).

13. The plasmid according to any of the preceding embodiments, wherein said plasmid expresses IL-10 and IL-2 at least about one hundred fold, two hundred fold, five hundred fold or at least about one thousand fold over TGF-β and insulin antigen (ratio of IL-10+IL-2 to insulin+TGF-β may be at least 100:1, or 200:1, or 500:1 or 1000:1).

14. The plasmid according to any of the preceding embodiments, wherein said plasmid expresses IL-10 and IL-2 in a ratio of about 1:1-100:1, such as e.g. 1:1-50:1, such as e.g. 1:1-25:1, such as e.g. 1:1-10:1, alternatively 1:1-5:1, alternatively 1:1-3:1, alternatively 1:1-2:1. Alternatively, the ratio between expressed IL-10 and expressed IL-2 may be about 1:1, 1:0.9, 1:0.8, 1:0.7, 1:0.6, 1:0.5, 1:0.4; 1:0.3, 1:0.2, or 1:0.1.

15. The plasmid according to any of the preceding embodiments, wherein said plasmid comprises: (i) an FMDV 2A element separating the insulin antigen encoding sequence and the TGF-β encoding sequence, (ii) an EMCV IRES element separating the TGF-β encoding sequence and the IL-10 encoding sequence, and (iii) a 2A element separating the IL-10 encoding sequence and the IL-2 encoding sequence.

16. The plasmid according to any of the preceding embodiments, wherein said plasmid comprises:

(i) a 2A element (such as an FMDV 2A or a P 2A element) separating the insulin antigen encoding sequence and the TGF-β encoding sequence, (ii) an EMCV IRES element (alternatively a bi-directional promoter) separating the TGF-β encoding sequence and the IL-10 encoding sequence (preferably, three alanine amino acids are encoded immediately N-terminal to the IL-10 gene), and (iii) a 2A element (such as a P 2A element) separating the IL-10 encoding sequence and the IL-2 encoding sequence.

17. The plasmid according to any of the preceding embodiments, wherein the TGF-β encoding sequence encodes constitutively active TGF-β, preferably constitutively active human TGF-β1.

18. The plasmid according to any of the preceding embodiments, wherein said plasmid comprises: (i) an endosomally targeted pre-pro-insulin encoding sequence, (ii) an FMDV 2A element, (iii) a TGF-β encoding sequence, (iv) an EMCV IRES element, (v) an IL-10 encoding sequence, (vi) a P 2A element, (vii) an IL-2 encoding sequence, (viii) a polyadenylation/termination element, (ix) a selection gene, (x) an origin of replication, (xi) a eukaryotic promoter element, (xii) a eukaryotic translational start sequence, (xiii) an endosomal sorting sequence, and (xiv) optionally an intron. 19. The plasmid according to any of the preceding embodiments, wherein said plasmid comprises the following elements:

(i) a promoter (such as a CMV IE promoter), (ii) an intron (located within the noncoding leader sequence), and (iii) a eukaryotic translational start sequence (such as a Kozak element), (iv) an endosomally targeted antigen encoding sequence (such as an endosomally targeted human secretion-defective pre-pro-insulin encoding sequence), (v) an FMDV 2A element preferably separating the antigen encoding sequence and the TGF-β encoding sequence, (vi) a TGF-β encoding sequence (such as a constitutively active human TGF-β encoding sequence, preferably a constitutively active human TGF-β1 encoding sequence), (vii) an EMCV IRES element (or alternatively a bi-directional eukaryotic promoter), wherein said EMCV IRES element separates the TGF-β encoding sequence and the IL-10 encoding sequences, (viii) an IL-10 encoding sequence (such as a human IL-10 encoding sequence with a three alanine amino acid N-terminal addition), (ix) a 2A element, such as a P 2A element, wherein said 2A element separates the IL-10 encoding sequence and the IL-2 encoding sequence, (x) an IL-2 encoding sequence (such as a human IL-2 encoding sequence), (xi) a termination element (such as a bGH_PA termination element), (xii) a selection gene (such as a kanamycin encoding sequence or a wt infA encoding sequence), (xiii) an origin of replication (such as a prokaryotic origin of replication, such as e.g. pUC ori).

20. The plasmid according to embodiment 18, wherein the elements (i)-(xiii) are arranged by order of expression.

21. The plasmid according to any of the preceding embodiments, wherein the DNA sequence of the plasmid is as set forth SEQ ID NO: 24, or essentially as set forth in SEQ ID NO: 24.

22. The plasmid according to embodiment 21, wherein a few minor modifications, resulting in e.g. one, two, three, or four amino acid substitution in one or more of the antigen and/or the cytokines are made to SEQ ID NO: 24 herein.

23. The plasmid according to any of embodiments 1-20, wherein the DNA sequence of the plasmid is as set forth in SEQ ID NO: 26 or a modification of SEQ ID NO: 26 resulting in e.g. one, two, three or four amino acid substitutions in one or more of the antigen and/or cytokines, or a modification of SEQ ID NO: 26 which results in expression of the same polypeptide sequences as from SEQ ID NO: 26.

24. The plasmid according to any of embodiments 1-20, wherein the DNA sequence of the plasmid is as set forth in SEQ ID NO: 26 or a modification of SEQ ID NO:26 having less than 100 bases which are different than SEQ ID NO: 26.

25. The plasmid according to any of embodiments 1-20, wherein the DNA sequence of the plasmid is as set forth in SEQ ID NO: 28 or a modification of SEQ ID NO: 28 resulting in e.g. one, two, three or four amino acid substitutions in one or more of the antigen and/or cytokines, or a modification of SEQ ID NO: 28 which results in expression of the same polypeptide sequences as from SEQ ID NO: 28.

26. The plasmid according to any of embodiments 1-20, wherein the DNA sequence of the plasmid is as set forth in SEQ ID NO:28 or a modification of SEQ ID NO:28 having less than 100 bases which are different than SEQ ID NO: 28.

27. The plasmid according to any of embodiments 1-20, wherein the DNA sequence of the plasmid is as set forth in SEQ ID NO: 29 or a modification of SEQ ID NO: 29 resulting in e.g. one, two, three or four amino acid substitutions in one or more of the antigen and/or cytokines, or a modification of SEQ ID NO: 29 which results in expression of the same polypeptide sequences as from SEQ ID NO: 29.

28. The plasmid according to any of embodiments 1-20, wherein the DNA sequence of the plasmid is as set forth in SEQ ID NO: 29 or a modification of SEQ ID NO: 29 having less than 100 bases which are different than SEQ ID NO: 29.

29. The plasmid according to any of embodiments 1-20, wherein said plasmid comprises a TGF-β gene comprising SEQ ID NO: 25 or SEQ ID NO: 25 having less than 10 base substitutions.

30. The plasmid according to any of the preceding embodiments for use in delaying or preventing type I diabetes.

31. The plasmid according to any of the preceding embodiments for intra-muscular, intradermal, intranasal, or subcutaneous administration.

32. The plasmid according to embodiment 31 for subcutaneous administration.

33. The plasmid according to embodiment 31 for intra-muscular injection.

34. The plasmid according to any of the preceding embodiments for use in treating a medical condition in a subject, such as e.g. type I diabetes, early-onset type I diabetes, or increased risk of developing type I diabetes (including type 1, 5 diabetes type of conditions).

35. A DNA immuno-therapy vaccine comprising a plasmid according to any of the preceding embodiments.

36. The DNA immuno-therapy vaccine according to embodiment 35 for use in delaying or preventing type I diabetes.

37. The DNA immuno-therapy vaccine according to any of embodiments 35-36 for intra-muscular, intradermal, intranasal, or subcutaneous administration.

38. The DNA immuno-therapy vaccine according to embodiment 37 for subcutaneous administration.

39. The DNA immuno-therapy vaccine according to embodiment 37 for intra-muscular administration.

40. The DNA immuno-therapy vaccine according to any of embodiments 35-39 used in association with, or in parallel with other types of medical treatments such as e.g. beta cell/beta stem cell therapy, beta cell/beta stem cell grafting, etc. to prolong the survival and efficacy of engrafted cells.

41. A pharmaceutical composition comprising the DNA immuno-therapy vaccine according to any of embodiments 34-39, or a plasmid according to any of embodiments 1-34, wherein said pharmaceutical composition comprises a saline solution and/or a buffer and/or a chelator.

42. A pharmaceutical composition comprising the DNA immuno-therapy vaccine according to any of embodiments 35-40, or a plasmid according to any of embodiments 1-34, wherein said pharmaceutical composition comprises a saline solution and/or a buffer and/or a chelator and/or ethanol.

43. The pharmaceutical composition according to any of embodiments 41-42, wherein the volume/volume percentage of ethanol is less than 5%, less than 4%, less than 3%, less than 2%, or less than 1%.

44. The pharmaceutical composition according to any of embodiments 41-43, wherein said composition does not comprise any virus, lipid co-packing agent, or condensation agent.

45. The pharmaceutical composition according to any of embodiments 41-44, wherein said composition further comprises a GLP-1R agonist.

46. The pharmaceutical composition according to any of embodiments 41-44, wherein said composition furthermore comprises a GLP-1 analogue/GLP-1R agonist.

47. The pharmaceutical composition according to any of embodiments 45-46 wherein said GLP-1 analogue or said GLP-1R agonist is selected from liraglutide, semaglutide or a mixture thereof.

48. A kit comprising a pharmaceutical composition according to any of embodiments 41-47 and a pharmaceutical composition comprising a GLP-1 analogue/GLP-1R agonist (e.g. liraglutide and/or semaglutide).

49. A method of producing a plasmid according to any of embodiments 1-34, wherein said method comprises (i) incubating a host cell, such as a host cell of bacterial origin such as e.g. *E. coli*) transfected with said plasmid under suitable conditions and (ii) recovering/purifying said plasmid.

50. The method according to embodiment 49, wherein said host cell is a *E. coli* infA thermosensitive strain.

51. A method of delaying the onset of Type-1 diabetes (T1D) or symptoms thereof in a patient at risk of developing T1D, or recently diagnosed with T1D, said method comprising administering a DNA immuno-therapy vaccine comprising the plasmid according to any of embodiments 1-31, optionally in combination with a GLP-1 analogue/GLP-1R agonist.

52. A method of preserving beta cell function and/or endogenous insulin production in an individual, said method comprising administering a DNA immuno-therapy vaccine comprising the plasmid according to any of embodiments 1-34, optionally in combination with a GLP-1 analogue/GLP-1R agonist.

53. A method of treating a diabetic individual comprising administering a vaccine comprising the plasmid according to any of embodiments 1-34, optionally in combination with a GLP-1 analogue/GLP-1R agonist (e.g. liraglutide and/or semaglutide).

54. A vaccine for preventing or delaying the onset of Type-1 diabetes (T1D) symptoms in a patient at risk of developing, or recently diagnosed with, T1D said vaccine comprising the plasmid according to any of embodiments 1-34.

55. A method of reducing the dosage of insulin in an individual having Type-1 diabetes (T1D), or a person at risk of developing T1D, said method comprising administering a DNA immuno-therapy vaccine comprising a plasmid according to any of embodiments 1-33, optionally in combination with a GLP-1 analogue/GLP-1R agonist (e.g. liraglutide and/or semaglutide).

EXAMPLES

Non Obese Diabetic mice (NOD mouse model of type 1 diabetes): Immune function in autoimmunity relies on a complex network of cellular interactions that cannot be adequately evaluated in vitro.

Disease suppression and/or treatment evaluations herein were carried out in the NOD mouse model, this model is a polygenic spontaneous onset model where most mice develop elevated blood glucose concentrations (BGV, blood glucose value, determined from tail-vein needlestick and handheld meter) between 12 and 30 weeks of age. Incidence and progression of disease is unpredictable, with total incidence ranging from 60% to 95% at 30 weeks of age (WoA) and progression from diagnosis (two sequential BGV readings of >250) to terminal (two sequential BGV readings of 600 or higher) ranging from 2 days to 4 weeks. Replication of elevated BGVs on sequential readings are necessary as mice are allowed food and water ad libitum which results in moderate BGV variability beyond that caused by immunopathology.

An example of a plasmid nucleotide sequence herein:

```
SEQ ID NO: 24: full (non-annotated) plasmid
sequence (6,401 base pairs)
GACTCTTCGCGATGTACGGGCCAGATATACGCGTTGACATTGATTATTGA

CTAGTTATTAATAGTAATCAATTACGGGGTCATTAGTTCATAGCCCATAT

ATGGAGTTCCGCGTTACATAACTTACGGTAAATGGCCCGCCTGGCTGACC

GCCCAACGACCCCCGCCCATTGACGTCAATAATGACGTATGTTCCCATAG

TAACGCCAATAGGGACTTTCCATTGACGTCAATGGGTGGACTATTTACGG

TAAACTGCCCACTTGGCAGTACATCAAGTGTATCATATGCCAAGTACGCC

CCCTATTGACGTCAATGACGGTAAATGGCCCGCCTGGCATTATGCCCAGT

ACATGACCTTATGGGACTTTCCTACTTGGCAGTACATCTACGTATTAGTC

ATCGCTATTACCATGGTGATGCGGTTTTGGCAGTACATCAATGGGCGTGG

ATAGCGGTTTGACTCACGGGGATTTCCAAGTCTCCACCCCATTGACGTCA

ATGGGAGTTTGTTTTGGCACCAAAATCAACGGGACTTTCCAAAATGTCGT

AACAACTCCGCCCCATTGACGCAAATGGGCGGTAGGCGTGTACGGTGGGA

GGTCTATATAAGCAGAGCTCTCTGGCTAACTAGAGAACCCACTGCTTACT

GGCTTATCGAAATTAATACGACTCACTATAGGGAGACCCAAGCTGGCTAG

CGTTTAAACTTAAGCTTGGTACCGAGCTCGGATCCACTAGTCCAGTGTGG

TGGAATTCTGCACTGCAGCTCGCATCTCTCCTTCACGCGCCCGCCGCCCT

ACCTGAGGCCGCCATCCACGCCGGTTGAGTCGCGTTCTGCCGCCTCCCGC

CTGTGGTGCCTCCTGAACTGCGTCCGCCGTCTAGGTAAGTTTAAAGCTCA

GGTCGAGACCGGGCCTTTGTCCGGCGCTCCCTTGGAGCCTACCTAGACTC

AGCCGGCTCTCCACGCTTTGCCTGACCCTGCTTGCTCAACTCTAGGTAAG

TTAATGAGACAGATAGAAACTGGTCTTGTAGAAACAGAGTAGTCGCCTGC

TTTTCTGCCAGGTGCTGACTTCTCTCCCCTGGGCTTTTTCTTTTTCTCA

GGTTGAAAAGAAGAAGACGAAGAAGACGAAGAAGACAAACCGTCGTCGAC

TGCCATGCGCCGCTGATTAACGCCGCCACCATGGCCCACCGACGCAGATC

CAGAAGCTGCCGTGAGGACCAGAAGCCCGTGATGGATGATCAGAGGGACC

TTATCTCTAACAATGAACAACTGCCAATGCTCGGCAGACGGCCTGGGGCC

CCGGAGAGCAAGTGCAGCAGAGGAGCCTTGTACACGGGGTTCTCCATTTT

AGTGACTCTCCTTCTCGCCGGCCAAGCTACCACCGCCTACTTTCTGTACC

AACAGCAAGGCAGACTAGACAAACTGACAATCACAAGCCAGAACCTTCAG

CTGGAGTCTCTGCGGATGAAGCTGCCCGCTTTGTGGATGAGATTGCTTCC

TCTACTTGCTCTCCTGGCGCTCTGGGGACCTGACCCCGAGCAAGAGTTTG

TTAATCAGCACCTGTGTGGGAGTCATCTGGTGGAGGCACTCTATTTAGTG

TGCGGAGAGAGGGGCTTCTTCTACACTCCAAAGACCAGACGGGAGGCCGA

AGACCTTCAAGTGGGGCAAGTAGAACTGGGTGGCGGACCCGGTGCCGGGA

GCCTTCAGCCGCTCGCCCTGGAGGGCTCTCTTCAGAAACGCGGCATCGTG

GAGCAGTGTTGCACATCCATTTGCTCACTCTACCAGCTGGAGAACTACTG

CAACGGAAGCGGAGTGAAGCAGACGTTGAATTTTGATTTGTTGAAGTTGG

CGGGGGATGTGGAGAGCAATCCGGGGCCGATGCCCCTAGTGGCCTCAGA

CTTTTGTTATTGTTATTACCGCTTTTATGGCTCTTGGTGCTGACACCGGG

CCGTCCGGCTGCTGGCTTGTCGACTTGTAAGACAATTGATATGGAATTGG

TGAAACGAAAACGGATTGAGGCCATCCGAGGACAGATTTTGAGCAAGCTG

CGGCTTGCCTCGCCACCCTCGCAAGGGGAAGTCCCACCCGGACCTCTACC

AGAAGCAGTCCTAGCGCTGTACAACAGTACAAGAGATAGAGTGGCCGGGG

AATCCGCAGAACCAGAGCCTGAGCCTGAAGCCGATTATTATGCAAAGGAA

GTGACTAGGGTCCTGATGGTCGAGACCCATAACGAAATCTACGACAAATT

CAAACAAAGTACCCACTCTATCTACATGTTCTTCAACACCAGTGAGCTAA

GAGAAGCCGTGCCCGAACCTGTGCTTCTTTCCCGCGCAGAACTCCGCCTC

TTGAGACTCAAATTGAAAGTTGAACAACACGTAGAGCTTTACCAGAAATA

CTCTAATAATTCATGGCGATATCTTTCTAATCGTCTCCTCGCCCCATCTG

ACAGCCCTGAATGGCTCTCCTTCGACGTTACGGGAGTTGTGCGCCAGTGG

CTCAGCAGAGGCGGAGAGATAGAGGGCTTTCGGCTGAGCGCACATGTATC

TGTGGACTCAAGGGACAACACATTGCAAGTGGATATTAACGGTTTTACAA

CTGGACGGAGAGGGACCTGGCGACCATCCACGGCATGAATAGACCTTTC

CTGCTGCTGATGGCTACTCCCCTGGAGAGGGCACAGCACTTACAGTCTTC

CAGACACCGGCGCGCCCTGGATACAAACTACTGCTTCAGCTCCACCGAAA

AGAACTGTTGCGTGCGGCAGCTGTACATTGACTTCAGAAAGGATCTGGGC

TGGAAGTGGATTCATGAGCCCAAGGGGTATCATGCCAACTTCTGTCTTGG

GCCATGCCCATACATCTGGTCACTGGATACCCAGTACTCCAAAGTTCTGG

CCTTGTACAATCAACACAACCCTGGAGCTTCCGCCGCTCCTTGCTGTGTG

CCCCAAGCCCTAGAGCCCCTGCCCATCGTTTATTATGTCGGACGCAAGCC

CAAAGTAGAACAGCTATCAAATATGATCGTGAGAAGCTGCAAGTGTAGCT

GATAAACGCGTCGAGCATGCATCTAGGGCGGCCAATTCCGCCCCTCTCCC

CCCCACCCCTCTCCCTCCCCCCCCCCTAACGTTACTGGCCGAAGCCGCTT

GGAATAAGGCCGGTGTGCGTTTGTCTATATGTTATTTTCCACCATATTGC

CGTCTTTTGGCAATGTGAGGGCCCGGAAACCTGGCCCTGTCTTCTTGACG

AGCATTCCTAGGGGTCTTTCCCCTCTCGCCAAAGGAATGCAAGGTCTGTT

GAATGTCGTGAAGGAAGCAGTTCCTCTGGAAGCTTCTTGAAGACAAACAA

CGTCTGTAGCGACCCTTTGTAGACAGCGGAACCCCCACCTGGCGATAGA

TGCCTCTGCGGCCAAAAGCCACGTGTATAAGATACACCTGCAAAGGCGGC

ACAACCCCAGTGCCACGTTGTGAGTTGGATAGTTGTGGAAAGAGTCAAAT
```

-continued

```
GGCTCTCCTCAAGCGTATTCAACAAGGGGCTGAAGGATGCCCAGAAGGTA
CCCCATTGTATGGGATCTGATCTGGGGCCTCGGTGCACATGCTTTACATG
TGTTTAGTCGAGGTTAAAAAACGTCTAGGCCCCCCGAACCACGGGGACGT
GGTTTTCCTTTGAAAAACACGATGATAATATGGCTGCCGCTCATTCTAGT
GCCCTTCTTTGCTGCCTGGTCCTGCTCACCGGGGTGCGAGCTAGCCCTGG
ACAAGGGACACAATCCGAAAACTCGTGCACCCACTTCCCGGGCAACCTCC
CTAACATGCTGAGGGACCTCCGTGATGCCTTCAGTAGAGTGAAGACGTTC
TTCCAAATGAAAGATCAGTTAGATAACCTGCTCCTGAAGGAGTCACTCTT
AGAAGACTTCAAAGGATACCTCGGCTGCCAAGCACTTAGCGAGATGATTC
AATTCTACTTAGAAGAAGTCATGCCTCAAGCTGAGAATCAAGACCCCGAC
ATCAAAGCTCATGTGAATTCTTTGGGAGAAAATTTGAAGACTTTGCGGCT
GCGGCTGCGGAGATGTCACCGCTTTCTGCCCTGTGAGAACAAATCAAAAG
CGGTCGAGCAAGTTAAGAATGCCTTCAATAAGCTACAAGAGAAGGGCATC
TACAAAGCAATGAGCGAGTTTGATATCTTTATCAATTACATTGAAGCCTA
CATGACAATGAAGATTAGGAATGCCGCGGGGAGCGGCGCTACTAACTTCA
GCCTGCTGAAGCAGGCTGGAGACGTGGAGGAGAACCCTGGACCTATGTAC
AGAATGCAGCTGCTGAGCTGCATCGCCCTGAGCCTGGCCCTGGTGACCAA
CAGCGCACCCACGTCCTCTAGCACCAAGAAGACCCAGTTACAGTTGGAGC
ATCTACTTTTAGACCTGCAAATGATTTTGAACGGCATCAACAACTACAAG
AATCCTAAACTTACTCGCATGCTTACCTTCAAATTTTACATGCCCAAGAA
GGCCACCGAACTGAAGCACTTGCAATGTCTGGAGGAAGAACTCAAGCCGC
TGGAGGAAGTTCTCAACCTCGCGCAGTCCAAGAATTTCCACCTCCGGCCA
AGAGACCTGATCAGTAACATTAATGTGATAGTGCTGGAGCTGAAGGGAAG
CGAGACTACATTTATGTGCGAGTACGCCGATGAAACCGCTACAATCGTCG
AGTTCCTGAATAGATGGATCACATTTTGCCAGTCAATTATCTCTACTCTG
ACATGATAACTCGAGGTCTAGAGGGCCCGTTTAAACCCGCTGATCAGCCT
CGACTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGG
GTGGGGTGGGGCAGGACAGCAAGGGGGAGGATTGGGAAGACAATAGCAGG
CATGCTGGGGATGCGGTGGGCTCTATGGCTTCTACTGGGCGGTTTTATGG
ACAGCAAGCGAACCGGAATTGCCAGCTGGGGCGCCCTCTGGTAAGGTTGG
GAAGCCCTGCAAAGTAAACTGGATGGCTTTCTCGCCGCCAAGGATCGAT
GGCGCAGGGGATCAAGCTCTGATCAAGAGACAGGATGAGGATCGTTTCGC
ATGGCCAAAGAAGACAATATTGAAATGCAAGGTACCGTTCTTGAAACGTT
GCCTAATACCATGTTCCGCGTAGAGTTAGAAAACGGTCACGTGGTTACTG
CACACATCTCCGGTAAAATGCGCAAAAACTACATCCGCATCCTGACGGGC
GACAAAGTGACTGTTGAACTGACCCCGTACGACCTGAGCAAAGGCCGCAT
TGTCTTCCGTAGTCGCTGATAAATTATTAACGCTTACAATTTCCTGATGC
GGTATTTTCTCCTTACGCATCTGTGCGGTATTTCACACCGCATACAGGTG
GCACTTTTCGGGGAAATGTGCGCGGAACCCCTATTTGTTTATTTTTCTAA
ATACATTCAAATATGTATCCGCTCATGAGACAATAACCCTGATAAATGCT
TCAATAATAGCACGTGCTAAAACTTCATTTTTAATTTAAAAGGATCTAGG
TGAAGATCCTTTTTGATAATCTCATGACCAAAATCCCTTAACGTGAGTTT
TCGTTCCACTGAGCGTCAGACCCCGTAGAAAAGATCAAAGGATCTTCTTG
AGATCCTTTTTTTCTGCGCGTAATCTGCTGCTTGCAAACAAAAAAACCAC
CGCTACCAGCGGTGGTTTGTTTGCCGGATCAAGAGCTACCAACTCTTTTT
CCGAAGGTAACTGGCTTCAGCAGAGCGCAGATACCAAATACTGTTCTTCT
AGTGTAGCCGTAGTTAGGCCACCACTTCAAGAACTCTGTAGCACCGCCTA
CATACCTCGCTCTGCTAATCCTGTTACCAGTGGCTGCTGCCAGTGGCGAT
AAGTCGTGTCTTACCGGGTTGGACTCAAGACGATAGTTACCGGATAAGGC
GCAGCGGTCGGGCTGAACGGGGGGTTCGTGCACACAGCCCAGCTTGGAGC
GAACGACCTACACCGAACTGAGATACCTACAGCGTGAGCTATGAGAAAGC
GCCACGCTTCCCGAAGGGAGAAAGGCGGACAGGTATCCGGTAAGCGGCAG
GGTCGGAACAGGAGAGCGCACGAGGGGAGCTTCCAGGGGGAAACGCCTGGT
ATCTTTATAGTCCTGTCGGGTTTCGCCACCTCTGACTTGAGCGTCGATTT
TTGTGATGCTCGTCAGGGGGCGGAGCCTATGGAAAAACGCCAGCAACGC
GGCCTTTTTACGGTTCCTGGGCTTTTGCTGGCCTTTTGCTCACATGTTCT
T
```

Example 1

Antigen Encoding Plasmids Compared to Antigen+IL-10 Encoding Plasmids

It has been suggested in the prior art that depletion of immuno-stimulatory CpG sequences in the plasmid backbone would be required for effective DNA immuno-therapy treatment of T1D. This experiment was thus modelled after previously published experiments (2008 J Immunol. 181 (12):8298-307).

NOD mice were given eight once weekly doses of plasmid beginning at week 9 (age): either empty vector (pVAX1, 50 ug) was given, or pVAX1-proinsulin Ag (not endosomally targeted, not preproinsulin), or CpG depleted pVAX1-proinsulin Ag, or a bicistronic construct pVAX1-1L10-IRES-proinsulin Ag in equimolar ratios.

All administrations were intramuscular in the left quadriceps under isoflurane anaesthesia and contained only plasmid in PBS+EDTA. BGVs were assessed in all mice on a weekly basis and incidence of type 1 diabetes was scored based on two BGV readings over 250 mg/dl. Mice were evaluated until 30 weeks of age or a BGV of 600 were reached, followed by sacrifice.

The results from this experiment (table 1) demonstrate that A) CpG depletion is neither necessary nor beneficial for efficacy, B) the inclusion of immuno-modulatory cytokines significantly increases efficacy, and C) the plasmid backbone (empty vector) is equivalent to untreated groups.

TABLE 1

T1D incidence in NOD mice at 30 weeks of age.

| Plasmid | T1DDisease incidence at 30 weeks of age |
|---|---|
| Historical untreated colony incidence | 77.8% |
| pVAX1 (empty vector negative control) | 23/29 = 79.3% |
| CpG depleted pVAX1-proinsulin Ag (antigen + modified vector) | 24/29 = 82.7% |
| pVAX1-proinsulin Ag (antigen) | 18/30 = 60% |
| pVAX1-IL10-IRES-proinsulin Ag (antigen + IL-10) | 10/26 = 38.5% |

Example 2

Expressed Protein Products Resulting from Plasmids Encoding Antigen, IL-10, IL-2 and TGF-β

Multi-cistronic plasmids were created to co-express TGF-β, IL-10, and optionally IL-2. Freestyle293 cells were transiently transfected and cultured in serum-free media. Supernatants were collected and subjected to ELISA quantification after 72 hours.

The results in table 2 below shows that: A) expression of multiple independent cytokines is achieved from a single vector, B) significant amounts of each cytokine are produced and in the expected ratios, C) minor sequence changes significantly improve IL-10 expression from the first generation IL10/proinsulin plasmid, and D) neither the plasmid backbone (empty vector) or endosomal targeting of antigen (IIAg) induces cytokine production or dysregulation.

TABLE 2

ELISA quantification of expressed protein products.

| Plasmid | Active TGF-b1 (ng/ml) | Interleukin-10 (ng/ml) | Interleukin-2 (ng/ml) |
|---|---|---|---|
| pVAX1 (empty vector) | <0.0035 | <0.0027 | <0.0009 |
| pVAX1-IL10/Proinsulin (antigen + IL-10) | <0.0035 | 85.3 | <0.0009 |
| pVAX1-IIAg/TGFβ/IL10/ (antigen + TGFβ + IL-10) | 7.35 | 1,238.8 | <0.0009 |
| pVAX1-IIAg/TGFβ/IL10/IL2 (antigen + TGFβ + IL-10 + IL-2) | 2.39 | 1,259.5 | 777.0 |

Example 3

Impact of TGF-β and IL-2 on Disease Suppression

Multi-cistronic plasmids were evaluated for disease prevention in NOD mice as in Example 1, with the exception that dosing was continued once weekly until sacrifice (onset of diabetes) or week 30. One mouse from each group (initial n=24) was sent out for full necropsy after 10 weeks of dosing—including pathology on 10 standard highly perfused tissues, complete blood count, and clinical chemistry. Other than minor muscle disruption and regrowth due to mechanical trauma at the injection site, there were no deviations from un-dosed animals.

The results in table 3 below shows that: A) addition of TGF significantly increases efficacy, B) the inclusion of Interleukin-2 may increase efficacy and does not induce pathology, C) chronic dosing with plasmids expressing IL-10 and antigen increases efficacy in disease prevention, and D) chronic dosing with plasmids expressing TGFβ, IL-10 and IL-2 increases efficacy without resulting in any safety signals.

TABLE 3

T1D incidence in NOD mice.

| Plasmid | Disease incidence at 30 weeks of age |
|---|---|
| Historical untreated colony incidence | 77.8% |
| Untreated (negative control) | 18/21 = 85.7% |
| pVAX1-Ag/IL10 (antigen + IL-10) | 5/23 = 21.7% |
| pVAX1-IIAg/TGFβ/IL10 (antigen + TGFβ + IL-10) | 2/23 = 8.7% |
| pVAX1-IIAg/TGFβ/IL10/IL2 (antigen + TGFβ + IL-10 + IL-2) | 1/23 = 4.3% |

Example 4

Evaluation of IRES Elements, Introns as Well as Subcutaneous Administration

Multi-cistronic plasmids were evaluated for disease prevention in NOD mice as in Example 3, except that dosing began earlier (at week 5) in order to better mimic chronic pediatric administration. In addition to validating the pVAX1-IIAg/TGFβ/IL10 and pVAX1-IIAg/TGFβ/IL10/IL2 plasmids containing introns, other control groups were examined. Specifically, a different IRES segment (CrPV [from Cricket Paralysis Virus] as opposed to the EMCV [from EncephaloMyoCarditis Virus]) was evaluated for expected increases in efficacy, as was a deletion of the intron segment to assess its necessity. Due to obvious lack of efficacy compared to the parental plasmid (pVAX1-IIAg/TGFβ/IL10/IL2) the CrPV and intron-free (n.i.=no intron) groups were terminated early. In addition, the cohort of mice utilized in this experiment experienced more rapid progression of disease than previous cohorts, with time from diagnosis to sacrifice averaging 1.25 weeks rather than 2.75 from previous experiments. Finally, a subcutaneous administration group was added. This group was dosed with the triple cytokine plasmid (pVAX1-IIAg/TGFβ/IL10/IL2) with once weekly injection in the s.c. space in the scruff of the neck without anaesthesia.

The results in table 4 show that: A) EMCV IRES elements provide significantly better efficacy than the CrPV IRES, B) the inclusion of an intron (in this plasmid located within the CD74 endosomal targeting region) significantly increases efficacy, C) while the inclusion of IL-2 provides minimal benefit in mild disease settings its presence significantly increases the efficacy and robustness of treatment in aggressive disease settings, and D) subcutaneous dosing, which is ineffective in most DNA vaccine applications, here shows modest efficacy and a significant delay of disease even without optimization.

TABLE 4

T1D incidence in NOD mice.

| Treatment type | Diabetic/total | % diabetic |
|---|---|---|
| Historical control | | 80% @ 30 Weeks |
| Untreated | 15/21 | 71.4% @ 30 Weeks |
| Empty vector control i.m. | 13/21 | 61.9% @ 30 Weeks |
| pVAX1-IIAg/TGFβ/IL10/IL2 (no Intron) i.m. | 10/24 | 41.6% @ 22 Weeks |
| pVAX1-IIAg/TGFβ/IL10/IL2 (CrPv IRES instead of EMCV IRES). i.m | 7/22 | 31.8% @ 22 Weeks |
| pVAX1-IIAg/TGFβ/IL10 i.m. (no IL-2) | 12/42 | 28.6% @ 30 Weeks |
| pVAX1-IIAg/TGFβ/IL10/IL2 i.m. | 1/42 | 2.4% @ 30 Weeks |
| pVAX1-IIAg/TGFβ/IL10/IL2 s.c. | 12/42 | 28.6% @ 30 Weeks |

Example 5

Comparison of Commercial Antibiotic Free Selection with Antibiotic Selection Systems An alternate plasmid backbone was evaluated with the object of removing kanamycin resistance to comply with European Medicines Agency guidance. The same insert (IIAg/TGFβ/IL10/IL2, including intron) was cloned into the Nature Technology NTC9385R "nanoplasmid" backbone. The resultant plasmid was evaluated in NOD mice as in Example 3, except that treatment began on week 11 (late start) and terminated early due to failure of the NTC9385R-based plasmid.

The results in table 5 below show that: A) changes to selection system of the plasmid backbone surprisingly induce significant changes to effectiveness of the plasmids, and B) a late start to treatment results in early conversions. Data from other, related experiments indicates that dosing with these tolerogenic DNA vaccine plasmids requires two to four weeks to have efficacy, such that a late start to treatment results in several early cases of diabetes before the treatment becomes efficacious.

TABLE 5

T1D disease incidence in NOD mice.

| Plasmid | Disease incidence at 30 weeks of age |
|---|---|
| Historical untreated colony incidence | 77.8% |
| Untreated (negative control) | 16/21 = 76.2% |
| pVAX1-IIAg/TGFβ/IL10/IL2 with intron (kanamycin resistant) | 5/21 = 23.8% |
| pNTC9385R-IIAg/TGFβ/IL10/IL2 with intron (commercial antibiotic free selection system) | 13/21 = 61.9% |

Example 6

Disease Suppression Efficacy with Plasmids with and without Antigen

To determine the role of the encoded antigen in the function of the plasmid two experiments were performed (Examples 6 and 7). An alternate plasmid was evaluated with the object of removing the antigen (pre-proinsulin) encoding region while retaining the CD74 targeting domain and all three secreted cytokines. The resultant plasmid was evaluated in NOD mice as in Example 3, except that treatment began on week 11 (late start).

This experiment demonstrates that the antigen portion is required for full efficacy and that it is not merely cytokine production driving the function of the plasmid. This is one of two criteria needed to demonstrate antigen-specificity of the treatment.

TABLE 6

T1D incidence in NOD mice.

| Plasmid | Disease incidence at 30 weeks of age |
|---|---|
| Historical untreated colony incidence | 77.8% |
| pVAX1-IIAg/TGFβ/IL10/IL2 (antigen + cytokines) | 2/22 = 9.1% |
| pVAX1-II/TGFβ/IL10/IL2 (no antigen + cytokines) | 15/28 = 53.5% |

Example 7

Impact of the Antigen Immuno-Therapy Herein on Efficiency of Unrelated Antigen Vaccines To determine the role of the encoded antigen in the function of the plasmid two experiments were performed (Examples 6 and 7). NOD mice were either sham treated with PBS injection or treated with pVAX1-IIAg/TGFβ/IL10/IL2 plasmid as in Example 3. Following four doses (i.e. at 13 weeks of age) each mouse was immunized i.p. with 50 μg of an irrelevant antigen (Chicken Ovalbumin, OVA) in 100 μl of a 1:1 alum suspension. Sham or plasmid treatments were continued once weekly until sacrifice three weeks (21 days) post-immunization at which time serum was collected. Class-switched (total IgG and IgG2a) antibodies against the ovalbumin antigen were determined via commercial ELISA kits. No significant differences were observed between plasmid and sham treated groups in their total anti-OVA IgG levels, nor did either group produce anti-OVA IgG2a.

The results in table 7 below show that while the plasmid suppresses immune responses related to the targeted disease, it does not suppress immune reactivity toward unrelated antigens (i.e. any antigens not encoded by the plasmid). This is the second of two criteria needed to demonstrate antigen-specificity of the treatment. As treatment of pediatric patients will involve concomitant administration of standard childhood vaccinations this is a significant advantage over systemic/generic immunosuppression via agents such as methotrexate or cyclosporine A.

TABLE 7

Response to irrelevant antigen in NOD mice that have received DNA immuno-therapy vaccination against T1D.

| Treatment | # samples | Mean ug anti-OVA IgG/mL serum | Error |
|---|---|---|---|
| Plasmid treated | 8 | 7.517 | +/−0.967 |
| PBS (Sham) treated | 5 | 8.954 | +/−1.227 |

These values result in a non-significant p value of 0.377 and a confidence interval of −1.99 to 4.87. These results indicate that treatment with the immunomodulatory plasmid does not impact immune response to other antigens not encoded by the plasmid, and therefore does not result in broad or systemic immuno suppression.

Example 8

Individual Protein Products Expressed from the Plasmid

The TaV 2A element resulted in unexpected IL-10+IL-2 fusion products herein (data not shown) and other separation strategies were therefore evaluated. Initial separation technologies included upstream extensions of the TaV 2A sequence (leading to rapid degradation and lack of secreted IL-10) and also a carboxypeptidase cleavage site (which induced death of transfected cell lines). Further separation strategies evaluated were GSG-TaV 2A, a furin cleavage site, a furin site followed by TaV 2A, P 2A, and E 2A (equine rhinitis virus A).

Freestyle293 cells were transiently transfected and cultured in serum-free media. Both cell pellets and supernatants were collected and subjected to semi-quantitative multicolor Western blotting after 72 hours.

The results in table 8 below show that: A) unexpectedly, proteolytic cleavage sites fail to function between IL-10 and IL-2 genes, B) GSG tags (decoupler sequences) between IL-10 IL-2 are preferable to extended insulator sequences, C) P 2A is preferable to either TaV 2A or E 2A, and D) 2A sequences may have significant and unexpected effects on the degradation and secretion of expressed upstream proteins such as IL-10.

TABLE 8

Separation of expressed IL-10 and IL-2 protein products.

| Plasmid | Cellular Interleukin-10 | Secreted Interleukin-10 | Cellular Interleukin-2 | Secreted Interleukin-2 | Cellular Fused product | Secreted Fused product |
|---|---|---|---|---|---|---|
| GSG-TaV 2A | ++++ | ++ | − | +++ | ++ | − |
| Furin cleavage site | + | − | − | − | ++++ | ++ |
| Furin/TaV 2A | +++ | ++ | − | ++ | ++ | + |
| P 2A | ++ | ++++ | − | +++ | + | − |
| E 2A | +++ | ++ | − | ++ | ++ | − |

Example 9

Comparison of Commercial Selection System with a Heat Sensitive Selection System Provided Herein as Well as Comparison Between Plasmids Encoding IL-2 and Plasmids not Encoding IL-2 (Subcutaneous Administration)

Plasmid backbones were created and evaluated with the object of removing kanamycin resistance to comply with European Medicines Agency guidance. The corrected insert (IIAg/GSG-FMDV 2A/TGFβ/EMCV IRES/IL10/GSG-P 2A/IL2, including an intron in the upstream noncoding region) was cloned into either a retrofitted/minimally modified pVAX1 vector containing the Nature Technology "RNA-OUT" selection marker or an equivalent minimally modified pVAX1 vector encoding wt infA ("pNN") as backbones. Additionally, plasmids either containing an additional SV40 enhancer element or deficient in IL-2 were produced. The resultant plasmids were evaluated in NOD mice as in Example 3, except that administration was s.c. either once weekly or three times weekly (preferred).

The results shown in table 9+10 below show that: A) the commercially available exchange of RNA-OUT for the Kanamycin antibiotic resistance in the pVAX1 backbone still unexpectedly underperforms, B) the infA complementation antibiotic-free selection system performs equivalently to the parental pVAX1 vector, C) Interleukin-2 is required for optimal efficacy, D) addition of the SV40 enhancer element does not improve efficacy, and E) the corrected triple cytokine insert retains full functionality.

TABLE 9

T1D incidence in NOD mice.

| Plasmid, administered 3x weekly (optimal) | Disease incidence at 30 weeks of age |
|---|---|
| Historical untreated colony incidence | 78.9% |
| Untreated (negative control) | 12/15 = 80% |
| pNN empty vector (negative control with heat sensitive selection but no protein encoding sequences) | 12/16 = 75% |
| pVAX1-IIAg/FMDV/TGFβ/IL10/TaV2A/IL2 (kanamycin selection and protein encoding sequences) | 1/16 = 6.3% |
| pNN-IIAg/FMDV/TGFβ/IL10/P2A/IL2 (temperature selective system and protein encoding sequences) | 1/23 = 4.3% |
| pVAX1-RNA-OUT-IIAg/FMDV/TGFβ/IL10/P2A/IL2 (commercial selective system and protein encoding sequences) | 9/23 = 39.1% |

TABLE 10

T1D incidence in NOD mice.

| Plasmid, administered 1x weekly (sub-optimal) | Disease incidence at 27 weeks of age |
|---|---|
| Historical untreated colony incidence | 78.9% |
| Untreated (negative control) | 12/15 = 80% |
| pNN-IIAg/FMDV/TGFβ/IL10/P2A/IL2 (temperature selective system and protein encoding sequences) | 16/37 = 43.2% |
| pNN-SV40e-IIAg/FMDV/TGFβ/IL10/P2A/IL2 (temperature selective system and protein encoding sequences as well as an enhancer) | 20/37 = 54% |
| pNN-IIAg/FMDV/TGFβ/IL10 (IL-2 deficient) (temperature selective system and protein encoding sequences - except IL-2) | 25/40 = 62.5% |
| pVAX1-RNA-OUT-IIAg/FMDV/TGFβ/IL10/P2A/IL2 (commercial selective system and protein encoding sequences) | 27/38 = 71% |

Example 10

Examination of Durability of Tolerance Effect Following Plasmid Withdrawal

In the previous experiment (represented in Table 9), the pNN-IIAg/FMDV/TGFβ/IL10/P2A/IL2 group was not sacrificed at 30 weeks of age but ceased dosing with plasmid. Blood glucose values were followed for an additional ten (10) weeks, to a total of 40 weeks of age, to assess whether the plasmid had induced a durable state of tolerance or whether continued dosing was necessary for efficacy.

The results shown in table 11 below indicate that continued dosing is required for durability of tolerance, as a stable disease-free state to 30 weeks of age rapidly deteriorated following discontinuation of dosing. This indicates a beneficial safety profile, as any adverse events that might be encountered with plasmid dosing would also be expected to cease with dosing.

TABLE 11

T1D incidence in NOD mice following cessation of plasmid dosing.

| Disease incidence to 30 weeks of age | Disease incidence to 40 weeks of age |
|---|---|
| 1/23 = 4.3% | 9/23 = 39.1% |

Example 11

Examination of Plasmid Stability and Durability on Injection

A key issue with plasmid administration is degradation on administration. In the case of injection, shear forces encountered by large and viscous plasmid molecules passing through a thin needle under pressure lead to breakage of the covalently closed circular structure of the plasmid—rendering it linear and both subject to reduced transfection ability and rapid destruction. Most plasmids have 5 to 15% degradation to linear forms on injection through needles of sizes acceptable for clinical use, which leads to either reduced efficacy or a need for larger initial doses to compensate for the loss. Several types of sequence structures which may lead to plasmid unwinding and susceptibility to shear degradation were intentionally minimized in the plasmids disclosed, with the intention of increasing robustness and reliability with injection protocols. In order to assess shear degradation of plasmid, which can vary with viscosity and therefore concentration, the human lead plasmid was resuspended in Tris EDTA buffer to concentrations of 5, 7, and 9 mg/ml and passed three times though a G30 needle (expelled, re-drawn into syringe, then re-expelled) and one (1) microgram samples were run on an agarose gel against reference samples which were not passaged through the injection process.

The results shown in FIG. 3 indicate, surprisingly, that the plasmid is not noticeably degraded by three injection passages at any tested concentration or viscosity. Plasmid degradation would be visualized as both a smearing of smaller bands (in between the main supercoiled band at 6 Kb and the small process impurity band at the bottom of the gel or roughly 600 bp). Such linearization/degradation smears are not seen for any sample passaged through the injection process. This robust physical stability on dosing is highly desirable and both greater than anticipated or previously reported in literature.

Example 12

Verification of Plasmid Retention with infA Complementation System

In order to verify that the infA-based plasmid retention selection system functioned as desired, the plasmid transformed bacteria were grown through 100 passages (roughly 36 doublings/generations per passage, for a total of 3,600 generations of potential drift or plasmid loss examined). Passages 1-100 were generated at 11 per week, 2 passages per weekday at 37° C. and one each weekend at 30° C. All were performed in liquid animal-free LB media (Teknova soy-tone) supplemented with 15 micrograms/ml naladixic acid (selecting for DH5α base strain, not for plasmid presence). Glycerol stocks were generated from each passage and retained until all 100 passages were obtained for concurrent processing.

Scrapes of the glycerol stocks were used to inoculate 5 ml overnight cultures which were processed via supplier instructions on Qiagen miniprep kits using a vacuum manifold (either 16 or 32 cultures per run, due to gel size constraints). No attempt was made to collect OD600 readings for cell input normalization and all preps were done based on standard volumes. One microliter of each miniprep was subjected to PstI/XhoI digestion to resolve backbone (approximately 2.4 Kbp) from insert (approximately 4 Kbp), without correction for plasmid concentration resulting from each miniprep. Each gel was run with flanking Tridye 2-Log ladders (NEB www.neb.com/products/n3200-2-log-dna-ladder-01-100-kb), a first sample lane of undigested plasmid, and visualized with SybrSafe dye. In the images of the gels, despite lack of control for nucleic acid quantity, all digest lanes show both the presence and expected digestion pattern for plasmid (seen on the images for passages 1-16, 17-48, 49-80, and 81-100).

As an additional confirmation, glycerol stocks for passages 1-100 were also streaked onto 50 sector antibiotic-free and animal-free LB agar plates and incubated overnight at 30° C. No attempt to control for streak inoculum was made. As shown in FIG. 4, all glycerol stock representative streaks resulted in noticeable growth and thus plasmid retention.

Example 13

Suitability for Scale Up with infA Complementation System

In order to verify that the infA-based plasmid retention selection system functioned as desired at production scale, the plasmid transformed bacteria were used in a 50 L pilot fed-batch fermentor run with a specific yield enhancing temperature shift step. Minimal medium with the addition of yeast extract was utilized, reducing the doubling rate to 0.88/hour. The fed-batch was initiated at 17 h 00 post inoculation and the regulation of dissolved oxygen at 30% was realized by successive increase of the pO2 cascade parameters (stirring at 32 h 15, pressure at 40 h 30, then air flow at 45 h 40). The biomass increase rate lessened immediately following the shift to 42° C., as anticipated. The amount of plasmid DNA produced was estimated at 1.03±0.17 g/L using a small scale plasmid extraction procedure mimicking immediate post-lysis yield.

The invention claimed is:

1. A plasmid comprising a nucleic acid sequence consisting of SEQ ID NO: 28.

2. A pharmaceutical composition comprising the plasmid according to claim 1, further comprising a saline solution and/or a buffer and/or a chelator.

3. The pharmaceutical composition according to claim 2, wherein said buffer does not comprise any virus, lipid co-packing agent, or condensation agent.

4. The pharmaceutical composition according to claim 2, wherein said composition furthermore comprises a GLP-1R (Glucagon-like peptide-1 receptor) agonist.

5. A DNA immuno-therapy vaccine comprising the plasmid according to claim 1.

6. A method of delaying onset of type I diabetes, comprising administering the vaccine of claim 5 to a subject in need thereof.

7. The method of claim 6, wherein the vaccine is administered subcutaneously.

8. The method of claim 6, wherein the vaccine is administered intra-muscularly.

9. A plasmid consisting of a nucleic acid sequence of SEQ ID NO: 28.

10. A pharmaceutical composition comprising the plasmid according to claim 9, further comprising a saline solution and/or a buffer and/or a chelator.

11. The pharmaceutical composition according to claim 10, wherein said buffer does not comprise any virus, lipid co-packing agent, or condensation agent.

12. The pharmaceutical composition according to claim 10, wherein said composition furthermore comprises a GLP-1R agonist.

13. A DNA immuno-therapy vaccine comprising the plasmid according to claim 9.

14. A method of delaying onset of type I diabetes, comprising administering the vaccine of claim 13 to a subject in need thereof.

15. The method of claim 14, wherein the vaccine is administered subcutaneously.

16. The method of claim 14, wherein the vaccine is administered intra-muscularly.

* * * * *

SEQUENCE LISTING

<160> NUMBER OF SEQ ID NOS: 36

<210> SEQ ID NO 1
<211> LENGTH: 86
<212> TYPE: PRT
<213> ORGANISM: mus musculus

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 86
<212> TYPE: PRT
<213> ORGANISM: homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 3
<211> LENGTH: 110
<212> TYPE: PRT
<213> ORGANISM: Artificial Sequence
<220> FEATURE:
<223> OTHER INFORMATION: Synthetic

<400> SEQUENCE: 3

Met Ala Leu Trp Met Arg Leu Leu Pro Leu Leu Ala Leu Leu Ala Leu
1               5                   10                  15

Trp Gly Pro Asp Pro Glu Gln Glu Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

```
Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 4
<211> LENGTH: 110
<212> TYPE: PRT
<213> ORGANISM: Artificial Sequence
<220> FEATURE:
<223> OTHER INFORMATION: Synthetic

<400> SEQUENCE: 4

Met Ala Leu Trp Met Arg Leu Leu Pro Leu Leu Ala Leu Leu Ala Leu
1               5                   10                  15

Trp Gly Pro Asp Pro Glu Gln Glu Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 5
<211> LENGTH: 109
<212> TYPE: PRT
<213> ORGANISM: mus musculus

<400> SEQUENCE: 5

Ala Leu Trp Met Arg Leu Leu Pro Leu Leu Ala Leu Leu Ala Leu Trp
1               5                   10                  15

Gly Pro Asp Pro Ala Gln Ala Phe Val Asn Gln His Leu Cys Gly Ser
                20                  25                  30

His Leu Val Glu Ala Leu Tyr Leu Val Cys Gly Glu Arg Gly Phe Phe
            35                  40                  45

Tyr Thr Pro Lys Thr Arg Arg Glu Ala Glu Asp Leu Gln Val Gly Gln
        50                  55                  60

Val Glu Leu Gly Gly Gly Pro Gly Ala Gly Ser Leu Gln Pro Leu Ala
65                  70                  75                  80

Leu Glu Gly Ser Leu Gln Lys Arg Gly Ile Val Glu Gln Cys Cys Thr
                85                  90                  95

Ser Ile Cys Ser Leu Tyr Gln Leu Glu Asn Tyr Cys Asn
            100                 105

<210> SEQ ID NO 6
<211> LENGTH: 110
<212> TYPE: PRT
<213> ORGANISM: homo sapiens

<400> SEQUENCE: 6

Met Ala Leu Trp Met Arg Leu Leu Pro Leu Leu Ala Leu Leu Ala Leu
1               5                   10                  15

Trp Gly Pro Asp Pro Ala Gln Ala Phe Val Asn Gln His Leu Cys Gly
                20                  25                  30
```

```
Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
 50                  55                  60

Gln Val Glu Leu Gly Gly Gly Pro Gly Ala Gly Ser Leu Gln Pro Leu
 65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
                100                 105                 110

<210> SEQ ID NO 7
<211> LENGTH: 15
<212> TYPE: PRT
<213> ORGANISM: homo sapiens

<400> SEQUENCE: 7

Ser His Leu Val Glu Ala Leu Tyr Leu Val Cys Gly Glu Arg Gly
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ser His Leu Val Glu Ala Leu Tyr Leu Val Cys Gly Glu Glu Gly
 1               5                  10                  15

<210> SEQ ID NO 9
<211> LENGTH: 81
<212> TYPE: PRT
<213> ORGANISM: mus musculus

<400> SEQUENCE: 9

Met Asp Asp Gln Arg Asp Leu Ile Ser Asn His Glu Gln Leu Pro Ile
 1               5                  10                  15

Leu Gly Asn Arg Pro Arg Glu Pro Glu Arg Cys Ser Arg Gly Ala Leu
                20                  25                  30

Tyr Thr Gly Val Ser Val Leu Val Ala Leu Leu Leu Ala Gly Gln Ala
            35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
 65                  70                  75                  80

Pro

<210> SEQ ID NO 10
<211> LENGTH: 98
<212> TYPE: PRT
<213> ORGANISM: homo sapiens

<400> SEQUENCE: 10

Met His Arg Arg Arg Ser Arg Ser Cys Arg Glu Asp Gln Lys Pro Val
 1               5                  10                  15

Met Asp Asp Gln Arg Asp Leu Ile Ser Asn Asn Glu Gln Leu Pro Met
                20                  25                  30
```

Leu Gly Arg Arg Pro Gly Ala Pro Glu Ser Lys Cys Ser Arg Gly Ala
            35                  40                  45

Leu Tyr Thr Gly Phe Ser Ile Leu Val Thr Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Ile Thr Ser Gln Asn Leu Gln Leu Glu Ser Leu Arg Met Lys
                85                  90                  95

Leu Pro

<210> SEQ ID NO 11
<211> LENGTH: 219
<212> TYPE: DNA
<213> ORGANISM: E. coli

<400> SEQUENCE: 11
atggccaaag aagacaatat tgaaatgcaa ggtaccgttc ttgaaacgtt gcctaatacc     60
atgttccgcg tagagttaga aaacggtcac gtggttactg cacacatctc cggtaaaatg    120
cgcaaaaact acatccgcat cctgacgggc gacaaagtga ctgttgaact gaccccgtac    180
gacctgagca aggccgcat tgtcttccgt agtcgctga                            219

<210> SEQ ID NO 12
<211> LENGTH: 72
<212> TYPE: PRT
<213> ORGANISM: E. coli

<400> SEQUENCE: 12

Met Ala Lys Glu Asp Asn Ile Glu Met Gln Gly Thr Val Leu Glu Thr
1               5                   10                  15

Leu Pro Asn Thr Met Phe Arg Val Glu Leu Glu Asn Gly His Val Val
                20                  25                  30

Thr Ala His Ile Ser Gly Lys Met Arg Lys Asn Tyr Ile Arg Ile Leu
            35                  40                  45

Thr Gly Asp Lys Val Thr Val Glu Leu Thr Pro Tyr Asp Leu Ser Lys
    50                  55                  60

Gly Arg Ile Val Phe Arg Ser Arg
65                  70

<210> SEQ ID NO 13
<211> LENGTH: 127
<212> TYPE: DNA
<213> ORGANISM: L. monocytogenes

<400> SEQUENCE: 13
tgtaaaaaac atcatttagc gtgactttct ttcaacagct aacaattgtt gttactgcct     60
aatgttttta gggtatttta aaaagggcg ataaaaaacg attggggat gagaaatgaa      120 cgctcaa                                                              127

<210> SEQ ID NO 14
<211> LENGTH: 10
<212> TYPE: DNA
<213> ORGANISM: Artificial Sequence
<220> FEATURE:
<223> OTHER INFORMATION: Synthetic

<400> SEQUENCE: 14 gccrccatgg                                                            10

```
<210> SEQ ID NO 15
<211> LENGTH: 24
<212> TYPE: PRT
<213> ORGANISM: Artificial Sequence
<220> FEATURE:
<223> OTHER INFORMATION: Synthetic

<400> SEQUENCE: 15

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 16
<211> LENGTH: 20
<212> TYPE: PRT
<213> ORGANISM: Thosea asigna

<400> SEQUENCE: 16

Arg Ala Glu Gly Arg Gly Ser Leu Leu Thr Cys Gly Asp Val Glu Glu
1               5                   10                  15

Asn Pro Gly Pro
            20

<210> SEQ ID NO 17
<211> LENGTH: 19
<212> TYPE: PRT
<213> ORGANISM: Artificial Sequence
<220> FEATURE:
<223> OTHER INFORMATION: Synthetic

<400> SEQUENCE: 17

Ala Thr Asn Phe Ser Leu Leu Lys Gln Ala Gly Asp Val Glu Glu Asn
1               5                   10                  15

Pro Gly Pro

<210> SEQ ID NO 18
<211> LENGTH: 390
<212> TYPE: PRT
<213> ORGANISM: homo sapiens

<400> SEQUENCE: 18

Met Pro Pro Ser Gly Leu Arg Leu Leu Leu Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140
```

```
Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
            165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
            195                 200                 205

Ser Arg Gly Gly Glu Ile Glu Gly Phe Arg Leu Ser Ala His Cys Ser
            210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
            290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
            370                 375                 380

Arg Ser Cys Lys Cys Ser
385                 390

<210> SEQ ID NO 19
<211> LENGTH: 390
<212> TYPE: PRT
<213> ORGANISM: Artificial Sequence
<220> FEATURE:
<223> OTHER INFORMATION: Synthetic

<400> SEQUENCE: 19

Met Pro Pro Ser Gly Leu Arg Leu Leu Leu Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
            85                  90                  95

Pro Glu Pro Glu Ala Asp Tyr Tyr Ala Lys Glu Val Thr Arg Val Leu
            100                 105                 110
```

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
        130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Val Ser
210                 215                 220

Val Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 20
<211> LENGTH: 228
<212> TYPE: DNA
<213> ORGANISM: Artificial Sequence
<220> FEATURE:
<223> OTHER INFORMATION: Synthetic

<400> SEQUENCE: 20
cgactgtgcc ttctagttgc cagccatctg ttgtttgccc ctccccgtg ccttccttga      60 ccctggaagg tgccactccc actgtccttt cctaataaaa tgaggaaatt gcatcgcatt    120
gtctgagtag gtgtcattct attctggggg gtggggtggg gcaggacagc aaggggagg     180 attgggaaga caatagcagg catgctgggg atgcggtggg ctctatgg                 228

<210> SEQ ID NO 21
<211> LENGTH: 31
<212> TYPE: PRT
<213> ORGANISM: homo sapiens

<400> SEQUENCE: 21

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Synthetic

<400> SEQUENCE: 22

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: aminoisobutyric acid

<400> SEQUENCE: 23

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 24
<211> LENGTH: 6401
<212> TYPE: DNA
<213> ORGANISM: Artificial Sequence
<220> FEATURE:
<223> OTHER INFORMATION: Synthetic

<400> SEQUENCE: 24

| | | | | |
|---|---|---|---|---|
| gactcttcgc | gatgtacggg | ccagatatac | gcgttgacat | tgattattga ctagttatta | 60 |
| atagtaatca | attacggggt | cattagttca | tagcccatat | atggagttcc gcgttacata | 120 |
| acttacggta | aatggcccgc | ctggctgacc | gcccaacgac | ccccgcccat tgacgtcaat | 180 |
| aatgacgtat | gttcccatag | taacgccaat | agggactttc | cattgacgtc aatgggtgga | 240 |
| ctatttacgg | taaactgccc | acttggcagt | acatcaagtg | tatcatatgc caagtacgcc | 300 |
| ccctattgac | gtcaatgacg | gtaaatggcc | cgcctggcat | tatgcccagt acatgacctt | 360 |
| atgggacttt | cctacttggc | agtacatcta | cgtattagtc | atcgctatta ccatggtgat | 420 |
| gcggttttgg | cagtacatca | atgggcgtgg | atagcggttt | gactcacggg gatttccaag | 480 |
| tctccacccc | attgacgtca | atgggagttt | gttttggcac | caaaatcaac gggactttcc | 540 |
| aaaatgtcgt | aacaactccg | ccccattgac | gcaaatgggc | ggtaggcgtg tacggtggga | 600 |
| ggtctatata | agcagagctc | tctggctaac | tagagaaccc | actgcttact ggcttatcga | 660 |
| aattaatacg | actcactata | gggagaccca | agctggctag | cgtttaaact taagcttggt | 720 |
| accgagctcg | gatccactag | tccagtgtgg | tggaattctg | cactgcagct cgcatctctc | 780 |

-continued

```
cttcacgcgc cgccgccct acctgaggcc gccatccacg ccggttgagt cgcgttctgc    840
cgcctcccgc ctgtggtgcc tcctgaactg cgtccgccgt ctaggtaagt ttaaagctca    900
ggtcgagacc gggcctttgt ccggcgctcc cttggagcct acctagactc agccggctct    960
ccacgctttg cctgaccctg cttgctcaac tctaggtaag ttaatgagac agatagaaac   1020
tggtcttgta gaaacagagt agtcgcctgc ttttctgcca ggtgctgact tctctcccct   1080
gggctttttt cttttctca ggttgaaaag aagaagacga agaagacgaa gaagacaaac    1140
cgtcgtcgac tgccatgcgc cgctgattaa cgccgccacc atggcccacc gacgcagatc   1200
cagaagctgc cgtgaggacc agaagcccgt gatggatgat cagagggacc ttatctctaa   1260
caatgaacaa ctgccaatgc tcggcagacg gcctggggcc ccggagagca agtgcagcag   1320
aggagccttg tacacggggt tctccatttt agtgactctc cttctcgccg gccaagctac   1380
caccgcctac tttctgtacc aacagcaagg cagactagac aaactgacaa tcacaagcca   1440
gaaccttcag ctggagtctc tgcgatgaa gctgcccgct ttgtggatga gattgcttcc    1500
tctacttgct ctcctggcgc tctggggacc tgaccccgag caagagtttg ttaatcagca   1560
cctgtgtggg agtcatctgg tggaggcact ctatttagtg tgcggagaga ggggcttctt   1620
ctacactcca aagaccagac gggaggccga agaccttcaa gtggggcaag tagaactggg   1680
tggcggaccc ggtgccggga gccttcagcc gctcgccctg gagggctctc ttcagaaacg   1740
cggcatcgtg gagcagtgtt gcacatccat ttgctcactc taccagctgg agaactactg   1800
caacggaagc ggagtgaagc agacgttgaa ttttgatttg ttgaagttgg cggggatgt    1860 ggagagcaat ccggggccga tgcccctag tggcctcaga cttttgttat tgttattacc    1920
gcttttatgg ctcttggtgc tgacaccggg ccgtccggct gctggcttgt cgacttgtaa   1980
gacaattgat atggaattgg tgaaacgaaa acggattgag ccatccgag acagatttt    2040 gagcaagctg cggcttgcct cgccacccctc gcaggggaa gtcccacccg gacctctacc   2100
agaagcagtc ctagcgctgt acaacagtac aagagataga gtggccgggg aatccgcaga   2160
accagagcct gagcctgaag ccgattatta tgcaaaggaa gtgactaggg tcctgatggt   2220
cgagacccat aacgaaatct acgacaaatt caaacaaagt acccactcta tctacatgtt   2280
cttcaacacc agtgagctaa gagaagccgt gcccgaacct gtgcttcttt cccgcgcaga   2340
actccgcctc ttgagactca aattgaaagt tgaacaacac gtagagcttt accagaaata   2400
ctctaataat tcatggcgat atctttctaa tcgtctcctc gccccatctg acagccctga   2460
atggctctcc ttcgacgtta cgggagttgt gcgccagtgg ctcagcagag cggagagat    2520 agagggcttt cggctgagcg cacatgtatc tgtggactca agggacaaca cattgcaagt   2580
ggatattaac ggttttacaa ctggacggag aggggacctg cgaccatcc acggcatgaa    2640 tagcctttc ctgctgctga tggctactcc cctggagagg gcacagcact acagtcttc    2700 cagacaccgg cgcgccctgg atacaaacta ctgcttcagc tccaccgaaa agaactgttg   2760
cgtgcggcag ctgtacattg acttcagaaa ggatctgggc tggaagtgga ttcatgagcc   2820 caagggtat catgccaact tctgtcttgg gccatgccca tacatctggt cactggatac    2880
ccagtactcc aaagttctgg ccttgtacaa tcaacacaac cctggagctt ccgccgctcc   2940
ttgctgtgtg ccccaagccc tagagcccct gccatcgtt tattatgtcg gacgcaagcc    3000
caaagtagaa cagctatcaa atatgatcgt gagaagctgc aagtgtagct gataaacgcg   3060
tcgagcatgc atctagggcg gccaattccg cccctctccc cccaccccct ctccctcccc   3120
```

```
cccccctaac gttactggcc gaagccgctt ggaataaggc cggtgtgcgt ttgtctatat    3180
gttattttcc accatattgc cgtcttttgg caatgtgagg gcccggaaac ctggccctgt    3240
cttcttgacg agcattccta ggggtctttc ccctctcgcc aaaggaatgc aaggtctgtt    3300
gaatgtcgtg aaggaagcag ttcctctgga agcttcttga agacaaacaa cgtctgtagc    3360 gacccttttgt agacagcgga accccccacc tggcgataga tgcctctgcg gccaaaagcc    3420
acgtgtataa gatacacctg caaaggcggc acaaccccag tgccacgttg tgagttggat    3480
agttgtggaa agagtcaaat ggctctcctc aagcgtattc aacaaggggc tgaaggatgc    3540
ccagaaggta ccccattgta tgggatctga tctggggcct cggtgcacat gctttacatg    3600
tgtttagtcg aggttaaaaa acgtctaggc ccccgaacc acggggacgt ggttttcctt    3660
tgaaaaacac gatgataata tggctgccgc tcattctagt gcccttcttt gctgcctggt    3720
cctgctcacc ggggtgcgag ctagccctgg acaagggaca caatccgaaa actcgtgcac    3780
ccacttcccg ggcaacctcc ctaacatgct gagggacctc cgtgatgcct tcagtagagt    3840
gaagacgttc ttccaaatga agatcagtt agataacctg ctcctgaagg agtcactctt    3900
agaagacttc aaaggatacc tcggctgcca agcacttagc gagatgattc aattctactt    3960
agaagaagtc atgcctcaag ctgagaatca agaccccgac atcaaagctc atgtgaattc    4020
tttgggagaa aatttgaaga cttttgcggct gcggctgcgg agatgtcacc gctttctgcc    4080
ctgtgagaac aaatcaaaag cggtcgagca agttaagaat gccttcaata agctacaaga    4140
gaagggcatc tacaaagcaa tgagcgagtt tgatatcttt atcaattaca ttgaagccta    4200
catgacaatg aagattagga atgccgcggg gagcggcgct actaacttca gcctgctgaa    4260
gcaggctgga gacgtggagg agaaccctgg acctatgtac agaatgcagc tgctgagctg    4320
catcgccctg agcctggccc tggtgaccaa cagcgcaccc acgtcctcta gcaccaagaa    4380
gacccagtta cagttggagc atctactttt agacctgcaa atgattttga acggcatcaa    4440
caactacaag aatcctaaac ttactcgcat gcttaccttc aaattttaca tgcccaagaa    4500
ggccaccgaa ctgaagcact tgcaatgtct ggaggaagaa ctcaagccgc tggaggaagt    4560
tctcaacctc gcgcagtcca agaatttcca cctccggcca agagacctga tcagtaacat    4620
taatgtgata gtgctggagc tgaagggaag cgagactaca tttatgtgcg agtacgccga    4680
tgaaaccgct acaatcgtcg agttcctgaa tagatggatc acattttgcc agtcaattat    4740
ctctactctg acatgataac tcgaggtcta gagggcccgt ttaaacccgc tgatcagcct    4800
cgactgtgcc ttctagttgc cagccatctg ttgtttgccc ctcccccgtg ccttccttga    4860
ccctggaagg tgccactccc actgtccttt cctaataaaa tgaggaaatt gcatcgcatt    4920
gtctgagtag gtgtcattct attctggggg gtggggtggg gcaggacagc aagggggagg    4980
attgggaaga caatagcagg catgctgggg atgcggtggg ctctatggct tctactgggc    5040
ggttttatgg acagcaagcg aaccggaatt gccagctggg gcgccctctg gtaaggttgg    5100
gaagccctgc aaagtaaact ggatggcttt ctcgccgcca aggatctgat ggcgcagggg    5160
atcaagctct gatcaagaga caggatgagg atcgtttcgc atggccaaag aagacaatat    5220
tgaaatgcaa ggtaccgttc ttgaaacgtt gcctaatacc atgttccgcg tagagttaga    5280
aaacggtcac gtggttactg cacacatctc cggtaaaatg cgcaaaaact acatccgcat    5340
cctgacgggc gacaaagtga ctgttgaact gaccccgtac gacctgagca aaggccgcat    5400
tgtcttccgt agtcgctgat aaattattaa cgcttacaat ttcctgatgc ggtatttct    5460 ccttacgcat ctgtgcggta tttcacaccg catacaggtg gcacttttcg ggaaatgtg    5520
```

```
cgcggaaccc ctatttgttt attttttctaa atacattcaa atatgtatcc gctcatgaga    5580
caataaccct gataaatgct tcaataatag cacgtgctaa aacttcattt ttaatttaaa    5640
aggatctagg tgaagatcct ttttgataat ctcatgacca aaatccctta acgtgagttt    5700
tcgttccact gagcgtcaga ccccgtagaa aagatcaaag gatcttcttg agatcctttt    5760
tttctgcgcg taatctgctg cttgcaaaca aaaaaaccac cgctaccagc ggtggtttgt    5820
ttgccggatc aagagctacc aactcttttt ccgaaggtaa ctggcttcag cagagcgcag    5880
ataccaaata ctgttcttct agtgtagccg tagttaggcc accacttcaa gaactctgta    5940
gcaccgccta catacctcgc tctgctaatc ctgttaccag tggctgctgc cagtggcgat    6000
aagtcgtgtc ttaccgggtt ggactcaaga cgatagttac cggataaggc gcagcggtcg    6060
ggctgaacgg ggggttcgtg cacacagccc agcttggagc gaacgaccta caccgaactg    6120
agatacctac agcgtgagct atgagaaagc gccacgcttc ccgaagggag aaaggcggac    6180
aggtatccgg taagcggcag ggtcggaaca ggagagcgca cgagggagct tccaggggga    6240
aacgcctggt atctttatag tcctgtcggg tttcgccacc tctgacttga gcgtcgattt    6300
ttgtgatgct cgtcaggggg gcggagccta tggaaaaacg ccagcaacgc ggccttttta    6360
cggttcctgg cttttgctgg cctttttgct cacatgttct t                        6401
```

<210> SEQ ID NO 25
<211> LENGTH: 390
<212> TYPE: PRT
<213> ORGANISM: Artificial Sequence
<220> FEATURE:
<223> OTHER INFORMATION: Synthetic

<400> SEQUENCE: 25

```
Met Pro Pro Ser Gly Leu Arg Leu Leu Leu Leu Leu Pro Leu Leu
 1               5                  10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205
```

```
Ser Arg Gly Gly Glu Ile Glu Gly Phe Arg Leu Ser Ala His Ser Ser
    210                 215                 220
Ser Asp Ser Arg Asp Asn Thr Leu Gln Val Asp Ile Asn Gly Phe Thr
225                 230                 235                 240
Thr Gly Arg Arg Gly Asp Leu Ala Thr Ile His Gly Met Asn Arg Pro
                245                 250                 255
Phe Leu Leu Leu Met Ala Thr Pro Leu Glu Arg Ala Gln His Leu Gln
            260                 265                 270
Ser Ser Arg His Arg Arg Ala Leu Asp Thr Asn Tyr Cys Phe Ser Ser
        275                 280                 285
Thr Glu Lys Asn Cys Cys Val Arg Gln Leu Tyr Ile Asp Phe Arg Lys
    290                 295                 300
Asp Leu Gly Trp Lys Trp Ile His Glu Pro Lys Gly Tyr His Ala Asn
305                 310                 315                 320
Phe Cys Leu Gly Pro Cys Pro Tyr Ile Trp Ser Leu Asp Thr Gln Tyr
                325                 330                 335
Ser Lys Val Leu Ala Leu Tyr Asn Gln His Asn Pro Gly Ala Ser Ala
            340                 345                 350
Ala Pro Cys Cys Val Pro Gln Ala Leu Glu Pro Leu Pro Ile Val Tyr
        355                 360                 365
Tyr Val Gly Arg Lys Pro Lys Val Glu Gln Leu Ser Asn Met Ile Val
    370                 375                 380
Arg Ser Cys Lys Cys Ser
385                 390

<210> SEQ ID NO 26
<211> LENGTH: 6389
<212> TYPE: DNA
<213> ORGANISM: Artificial Sequence
<220> FEATURE:
<223> OTHER INFORMATION: Synthetic

<400> SEQUENCE: 26
gactcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
ctatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca gctggctag cgtttaaact taagcttggt     720
accgagctcg gatccactag tccagtgtgg tggaattctg cactgcagct cgcatctctc     780
cttcacgcgc ccgccgccct acctgaggcc gccatccacg ccggttgagt cgcgttctgc     840
cgcctcccgc ctgtggtgcc tcctgaactg cgtccgccgt ctaggtaagt ttaaagctca     900
ggtcgagacc gggcctttgt ccggcgctcc cttggagcct acctagactc agccggctct     960
```

```
ccacgctttg cctgaccctg cttgctcaac tctaggtaag ttaatgagac agatagaaac    1020
tggtcttgta gaaacagagt agtcgcctgc ttttctgcca ggtgctgact tctctccct     1080 gggctttttt cttttctca ggttgaaaag aagaagacga agaagacgaa gaagacaaac     1140
cgtcgtcgac tgccatgcgc cgctgattaa cgccgccacc atgggccacc gacgcagatc    1200
cagaagctgc cgtgaggacc agaagcccgt gatggatgat cagagggacc ttatctctaa    1260
caatgaacaa ctgccaatgc tcggcagacg gcctggggcc ccggagagca agtgcagcag    1320
aggagccttg tacacggggt tctccatttt agtgactctc cttctcgccg gccaagctac    1380
caccgcctac tttctgtacc aacagcaagg cagactagac aaactgacaa tcacaagcca    1440
gaaccttcag ctggagtctc tgcggatgaa gctgcccgct tgtggatga gattgcttcc      1500 tctacttgct ctcctggcgc tctgggacc tgaccccgag caagagtttg ttaatcagca      1560
cctgtgtggg agtcatctgg tggaggcact ctatttagtg tgcggagaga ggggcttctt    1620
ctacactcca aagaccagac gggaggccga agacttcaa gtggggcaag tagaactggg      1680
tggcggaccc ggtgccggga gccttcagcc gctcgccctg gagggctctc ttcagaaacg    1740
cggcatcgtg gagcagtgtt gcacatccat ttgctcactc taccagctgg agaactactg    1800
caacggaagc ggagtgaagc agacgttgaa ttttgatttg ttgaagttgg cggggatgt      1860 ggagagcaat ccggggccga tgcccctag tggcctcaga cttttgttat tgttattacc     1920
gcttttatgg ctcttggtgc tgacaccggg ccgtccggct gctggcttgt cgacttgtaa    1980
gacaattgat atggaattgg tgaaacgaaa acggattgag ccatccgag acagatttt       2040 gagcaagctg cggcttgcct cgccaccctc gcaaggggaa gtcccacccg gacctctacc    2100
agaagcagtc ctagcgctgt acaacagtac aagagataga gtggccgggg aatccgcaga    2160
accagagcct gagcctgaag ccgattatta tgcaaaggaa gtgactaggg tcctgatggt    2220
cgagacccat aacgaaatct acgacaaatt caaacaaagt acccactcta tctacatgtt    2280
cttcaacacc agtgagctaa gagaagccgt gcccgaacct gtgcttcttt cccgcgcaga    2340
actccgcctc ttgagactca aattgaaagt tgaacaacac gtagagcttt accagaaata    2400
ctctaataat tcatggcgat atcttttctaa tcgtctcctc gccccatctg acagccctga    2460
atggctctcc ttcgacgtta cgggagttgt gcgccagtgg ctcagcagag cggagagat     2520 agagggcttt cggctgagcg cacatagctc tagcgactca agggacaaca cattgcaagt    2580
ggatattaac ggttttacaa ctggacggag aggggacctg gcgaccatcc acggcatgaa    2640 tagcccttc ctgctgctga tggctactcc cctggagagg gcacagcact tacagtcttc     2700
cagacaccgg cgcgccctgg atacaaacta ctgcttcagc tccaccgaaa agaactgttg    2760
cgtgcggcag ctgtacattg acttcagaaa ggatctgggc tggaagtgga ttcatgagcc    2820 caagggtat catgccaact tctgtcttgg gccatgccca tacatctggt cactggatac      2880
ccagtactcc aaagttctgg ccttgtacaa tcaacacaac cctggagctt ccgccgctcc    2940
ttgctgtgtg ccccaagccc tagagcccct gcccatcgtt tattatgtcg gacgcaagcc    3000
caaagtagaa cagctatcaa atatgatcgt gagaagctgc aagtgtagct gataaacgcg    3060
tcgagcatgc atctagggcg gccaattccg cccctctccc cccacccct ctccctcccc      3120 cccccctaac gttactggcc gaagccgctt ggaataaggc cggtgtgcgt ttgtctatat     3180 gttatttcc accatattgc cgtcttttgg caatgtgagg gccggaaac ctggccctgt       3240 cttcttgacg agcattccta ggggtctttc ccctctcgcc aaaggaatgc aaggtctgtt    3300
gaatgtcgtg aaggaagcag ttcctctgga agcttcttga agacaaacaa cgtctgtagc    3360
```

```
gacccttttgt agacagcgga acccccacc  tggcgataga tgcctctgcg gccaaaagcc   3420
acgtgtataa gatacacctg caaaggcggc acaaccccag tgccacgttg tgagttggat   3480
agttgtggaa agagtcaaat ggctctcctc aagcgtattc aacaaggggc tgaaggatgc   3540
ccagaaggta ccccattgta tgggatctga tctggggcct cggtgcacat gctttacatg   3600
tgtttagtcg aggttaaaaa acgtctaggc ccccgaacc  acggggacgt ggttttcctt   3660
tgaaaaacac gatgataata tgatgcacag ctcagcactg ctctgttgcc tggtcctcct   3720
gactggggtg agggccagcc caggccaggg cacccagtct gagaacagct gcacccactt   3780
cccaggcaac ctgcctaaca tgcttcgaga tctccgagat gccttcagca gagtgaagac   3840
tttctttcaa atgaaggatc agctggacaa cttgttgtta aaggagtcct gctggagga   3900 cttttaagggt tacctgggtt gccaagcctt gtctgagatg atccagtttt acctggagga   3960
ggtgatgccc caagctgaga accaagaccc agacatcaag gcgcatgtga actccctggg   4020
ggagaacctg aagaccctca ggctgaggct acggcgctgt catcgatttc ttccctgtga   4080
aaacaagagc aaggccgtgg agcaggtgaa gaatgccttt aataagctcc aagagaaagg   4140
catctacaaa gccatgagtg agtttgacat cttcatcaac tacatagaag cctacatgac   4200
aatgaagata cgaaacggga gcggcgctac taacttcagc ctgctgaagc aggctggaga   4260
cgtggaggag aaccctggac ctatgtacag aatgcagctg ctgagctgca tcgccctgag   4320
cctggccctg gtgaccaaca gcgcacccac gtcctctagc accaagaaga cccagttaca   4380
gttggagcat ctacttttag acctgcaaat gattttgaac ggcatcaaca actacaagaa   4440
tcctaaactt actcgcatgc ttaccttcaa atttttacatg cccaagaagg ccaccgaact   4500
gaagcacttg caatgtctgg aggaagaact caagccgctg gaggaagttc tcaacctcgc   4560
gcagtccaag aatttccacc tccggccaag agacctgatc agtaacatta atgtgatagt   4620
gctggagctg aagggaagcg agactacatt tatgtgcgag tacgccgatg aaaccgctac   4680
aatcgtcgag ttcctgaata gatggatcac attttgccag tcaattatct ctactctgac   4740
atgataactc gaggtctaga gggcccgttt aaacccgctg atcagcctcg actgtgcctt   4800
ctagttgcca gccatctgtt gtttgcccct ccccgtgcc  ttccttgacc ctggaaggtg   4860
ccactcccac tgtcctttcc taataaaatg aggaaattgc atcgcattgt ctgagtaggt   4920
gtcattctat tctggggggt ggggtggggc aggacagcaa gggggaggat tgggaagaca   4980
atagcaggca tgctggggat gcggtgggct ctatggcttc tactgggcgg ttttatggac   5040
agcaagcgaa ccggaattgc cagctggggc gccctctggt aaggttggga agccctgcaa   5100
agtaaactgg atggctttct cgccgccaag gatctgatgg cgcaggggat caagctctga   5160
tcaagagaca ggatgaggat cgtttcgcat ggccaaagaa gacaatattg aaatgcaagg   5220
taccgttctt gaaacgttgc ctaataccat gttccgcgta gagttagaaa acggtcacgt   5280
ggttactgca cacatctccg gtaaaatgcg caaaaactac atccgcatcc tgacgggcga   5340
caaagtgact gttgaactga ccccgtacga cctgagcaaa ggccgcattg tcttccgtag   5400
tcgctgataa attattaacg cttacaattt cctgatgcgg tatttctcc  ttacgcatct   5460 gtgcggtatt tcacaccgca tacaggtggc acttttcggg gaaatgtgcg cggaaccct   5520 atttgtttat ttttctaaat acattcaaat atgtatccgc tcatgagaca ataaccctga   5580
taaatgcttc aataatagca cgtgctaaaa cttcattttt aatttaaaag gatctaggtg   5640
aagatccttt ttgataatct catgaccaaa atcccttaac gtgagttttc gttccactga   5700
```

| | | | | |
|---|---|---|---|---|
| gcgtcagacc | ccgtagaaaa | gatcaaagga | tcttcttgag | atcctttttt tctgcgcgta 5760 |
| atctgctgct | tgcaaacaaa | aaaccaccg | ctaccagcgg | tggtttgttt gccggatcaa 5820 |
| gagctaccaa | ctcttttcc | gaaggtaact | ggcttcagca | gagcgcagat accaaatact 5880 |
| gttcttctag | tgtagccgta | gttaggccac | cacttcaaga | actctgtagc accgcctaca 5940 |
| tacctcgctc | tgctaatcct | gttaccagtg | gctgctgcca | gtggcgataa gtcgtgtctt 6000 |
| accgggttgg | actcaagacg | atagttaccg | gataaggcgc | agcggtcggg ctgaacgggg 6060 |
| ggttcgtgca | cacagcccag | cttggagcga | acgacctaca | ccgaactgag atacctacag 6120 |
| cgtgagctat | gagaaagcgc | cacgcttccc | gaagggagaa | aggcggacag gtatccggta 6180 |
| agcggcaggg | tcggaacagg | agagcgcacg | agggagcttc | caggggggaaa cgcctggtat 6240 |
| ctttatagtc | ctgtcgggtt | tcgccacctc | tgacttgagc | gtcgattttt gtgatgctcg 6300 |
| tcagggggc | ggagcctatg | gaaaaacgcc | agcaacgcgg | ccttttacg gttcctgggc 6360 |
| ttttgctggc | cttttgctca | catgttctt | | 6389 |

<210> SEQ ID NO 27
<211> LENGTH: 15
<212> TYPE: PRT
<213> ORGANISM: Artificial Sequence
<220> FEATURE:
<223> OTHER INFORMATION: Synthetic

<400> SEQUENCE: 27

Ser His Leu Val Glu Ala Leu Tyr Leu Val Cys Gly Gly Glu Gly
1               5                   10                  15

<210> SEQ ID NO 28
<211> LENGTH: 6389
<212> TYPE: DNA
<213> ORGANISM: Artificial Sequence
<220> FEATURE:
<223> OTHER INFORMATION: Synthetic

<400> SEQUENCE: 28

| | | | | |
|---|---|---|---|---|
| gactcttcgc | gatgtacggg | ccagatatac | gcgttgacat | tgattattga ctagttatta 60 |
| atagtaatca | attacggggt | cattagttca | tagcccatat | atggagttcc gcgttacata 120 |
| acttacggta | aatggcccgc | ctggctgacc | gcccaacgac | ccccgcccat tgacgtcaat 180 |
| aatgacgtat | gttcccatag | taacgccaat | agggactttc | cattgacgtc aatgggtgga 240 |
| ctatttacgg | taaactgccc | acttggcagt | acatcaagtg | tatcatatgc caagtacgcc 300 |
| ccctattgac | gtcaatgacg | gtaaatggcc | cgcctggcat | tatgcccagt acatgacctt 360 |
| atgggacttt | cctacttggc | agtacatcta | cgtattagtc | atcgctatta ccatggtgat 420 |
| gcggttttgg | cagtacatca | atgggcgtgg | atagcggttt | gactcacggg gatttccaag 480 |
| tctccacccc | attgacgtca | atgggagttt | gttttggcac | caaaatcaac gggactttcc 540 |
| aaaatgtcgt | aacaactccg | ccccattgac | gcaaatgggc | ggtaggcgtg tacggtggga 600 |
| ggtctatata | agcagagctc | tctggctaac | tagagaaccc | actgcttact ggcttatcga 660 |
| aattaatacg | actcactata | gggagaccca | agctggctag | cgtttaaact taagcttggt 720 |
| accgagctcg | gatccactag | tccagtgtgg | tggaattctg | cactgcagct cgcatctctc 780 |
| cttcacgcgc | ccgccgccct | acctgaggcc | gccatccacg | ccggttgagt cgcgttctgc 840 |
| cgcctcccgc | ctgtggtgcc | tcctgaactg | cgtccgccgt | ctaggtaagt ttaaagctca 900 |
| ggtcgagacc | gggcctttgt | ccggcgctcc | cttggagcct | acctagactc agccggctct 960 |

-continued

```
ccacgctttg cctgaccctg cttgctcaac tctaggtaag ttaatgagac agatagaaac    1020
tggtcttgta gaaacagagt agtcgcctgc tttctgcca ggtgctgact tctctcccct    1080
gggctttttt cttttctca ggttgaaaag aagaagacga agaagacgaa gaagacaaac    1140
cgtcgtcgac tgccatgcgc cgctgattaa cgccgccacc atgcccacc gacgcagatc    1200
cagaagctgc cgtgaggacc agaagcccgt gatggatgat cagagggacc ttatctctaa    1260
caatgaacaa ctgccaatgc tcggcagacg gcctggggcc ccggagagca agtgcagcag    1320
aggagccttg tacacggggt tctccatttt agtgactctc cttctcgccg gccaagctac    1380
caccgcctac tttctgtacc aacagcaagg cagactagac aaactgacaa tcacaagcca    1440
gaaccttcag ctggagtctc tgcggatgaa gctgcccgct ttgtggatga gattgcttcc    1500
tctacttgct ctcctggcgc tctgggacc tgaccccgag caagagtttg ttaatcagca    1560
cctgtgtggg agtcatctgg tggaggcact ctatttagtg tgcggagaga ggggcttctt    1620
ctacactcca aagaccagac gggaggccga agaccttcaa gtggggcaag tagaactggg    1680
tggcggaccc ggtgccggga gccttcagcc gctcgccctg gagggctctc ttcagaaacg    1740
cggcatcgtg gagcagtgtt gcacatccat ttgctcactc taccagctgg agaactactg    1800
caacggaagc ggagtgaagc agacgttgaa ttttgatttg ttgaagttgg cggggggatgt    1860
ggagagcaat ccggggccga tgccccctag tggcctcaga cttttgttat tgttattacc    1920
gcttttatgg ctcttggtgc tgacaccggg ccgtccggct gctggcttgt cgacttgtaa    1980
gacaattgat atggaattgg tgaaacgaaa acggattgag gccatccgag acagattttt    2040
gagcaagctg cggcttgcct cgccaccctc gcaaggggaa gtcccacccg gacctctacc    2100
agaagcagtc ctagcgctgt acaacagtac aagagataga gtggccgggg aatccgcaga    2160
accagagcct gagcctgaag ccgattatta tgcaaaggaa gtgactaggg tcctgatggt    2220
cgagacccat aacgaaatct acgacaaatt caaacaaagt acccactcta tctacatgtt    2280
cttcaacacc agtgagctaa gagaagccgt gcccgaacct gtgcttcttt cccgcgcaga    2340
actccgcctc ttgagactca aattgaaagt tgaacaacac gtagagcttt accagaaata    2400
ctctaataat tcatggcgat atctttctaa tcgtctcctc gccccatctg acagccctga    2460
atggctctcc ttcgacgtta cgggagttgt gcgccagtgg ctcagcagag cggagagat    2520
agagggcttt cggctgagcg cacatagctc tagcgactca aggacaacaa cattgcaagt    2580
ggatattaac ggttttacaa ctggacggag aggggacctg gcgaccatcc acggcatgaa    2640
tagccctttc ctgctgctga tggctactcc cctggagagg gcacagcact acagtcttc    2700
cagacaccgg cgcgccctgg atacaaacta ctgcttcagc tccaccgaaa agaactgttg    2760
cgtgcggcag ctgtacattg acttcagaaa ggatctgggc tggaagtgga ttcatgagcc    2820
caagggtat catgccaact tctgtcttgg gccatgccca tacatctggt cactggatac    2880
ccagtactcc aaagttctgg ccttgtacaa tcaacacaac cctggagctt ccgccgctcc    2940
ttgctgtgtg ccccaagccc tagagcccct gccatcgtt tattatgtcg gacgcaagcc    3000
caaagtagaa cagctatcaa atatgatcgt gagaagctgc aagtgtagct gataaacgcg    3060
tcgagcatgc atctagggcg gccaattccg ccctctccc cccaccct ctccctcccc    3120
ccccctaac gttactggcc gaagccgctt ggaataaggc cggtgtgcgt ttgtctatat    3180
gttattttcc accatattgc cgtcttttgg caatgtgagg gccggaaac ctggccctgt    3240
cttcttgacg agcattccta ggggtctttc ccctctcgcc aaaggaatgc aaggtctgtt    3300
gaatgtcgtg aaggaagcag ttcctctgga agcttcttga agacaaacaa cgtctgtagc    3360
```

```
gacccttttgt agacagcgga acccccccacc tggcgataga tgcctctgcg gccaaaagcc   3420
acgtgtataa gatacacctg caaaggcggc acaaccccag tgccacgttg tgagttggat   3480
agttgtggaa agagtcaaat ggctctcctc aagcgtattc aacaaggggc tgaaggatgc   3540
ccagaaggta ccccattgta tgggatctga tctggggcct cggtgcacat gctttacatg   3600
tgtttagtcg aggttaaaaa acgtctaggc ccccgaacc acggggacgt ggttttcctt   3660
tgaaaaacac gatgataata tgatgcacag ctcagcactg ctctgttgcc tggtcctcct   3720
gactggggtg agggccagcc caggccaggg cacccagtct gagaacagct gcacccactt   3780
cccaggcaac ctgcctaaca tgcttcgaga tctccgagat gccttcagca gagtgaagac   3840
tttctttcaa atgaaggatc agctggacaa cttgttgtta aaggagtcct tgctggagga   3900 cttttaagggt tacctgggtt gccaagcctt gtctgagatg atccagtttt acctggagga   3960
ggtgatgccc caagctgaga accaagaccc agacatcaag gcgcatgtga actccctggg   4020
ggagaacctg aagaccctca ggctgaggct acggcgctgt catcgatttc ttccctgtga   4080
aaacaagagc aaggccgtgg agcaggtgaa gaatgccttt aataagctcc aagagaaagg   4140
catctacaaa gccatgagtg agtttgacat cttcatcaac tacatagaag cctacatgac   4200
aatgaagata cgaaacggga gcggcgctac taacttcagc ctgctgaagc aggctggaga   4260
cgtggaggag aaccctggac ctatgtacag aatgcagctg ctgagctgca tcgccctgag   4320
cctggccctg gtgaccaaca cgcacccac gtcctctagc accaagaaga cccagttaca   4380
gttggagcat ctacttttag acctgcaaat gattttgaac ggcatcaaca actacaagaa   4440
tcctaaactt actcgcatgc ttaccttcaa atttttcatg cccaagaagg ccaccgaact   4500
gaagcacttg caatgtctgg aggaagaact caagccgctg gaggaagttc tcaacctcgc   4560
gcagtccaag aatttccacc tccggccaag agacctgatc agtaacatta atgtgatagt   4620
gctggagctg aagggaagcg agactacatt tatgtgcgag tacgccgatg aaaccgctac   4680
aatcgtcgag ttcctgaata atggatcac attttgccag tcaattatct ctactctgac   4740
atgataactc gaggtctaga gggcccgttt aaacccgctg atcagcctcg actgtgcctt   4800
ctagttgcca gccatctgtt gtttgcccct cccccgtgcc ttccttgacc ctggaaggtg   4860
ccactcccac tgtcctttcc taataaaatg aggaaattgc atcgcattgt ctgagtaggt   4920
gtcattctat tctggggggt ggggtggggc aggacagcaa gggggaggat tgggaagaca   4980
atagcaggca tgctggggat gcggtgggct ctatggcttc tactgggcgg ttttatggac   5040
agcaagcgaa ccggaattgc cagctggggc gccctctggt aaggttggga agccctgcaa   5100
agtaaactgg atggctttct cgccgccaag gatctgatgg cgcaggggat caagctctga   5160
tcaagagaca ggatgaggat cgtttcgcat ggccaaagaa gacaatattg aaatgcaagg   5220
taccgttctt gaaacgttgc ctaataccat gttccgcgta gagttagaaa acggtcacgt   5280
ggttactgca cacatctccg gtaaaatgcg caaaaactac atccgcatcc tgacgggcga   5340
caaagtgact gttgaactga ccccgtacga cctgagcaaa ggccgcattg tcttccgtag   5400
tcgctgataa attattaacg cttacaattt cctgatgcgg tatttctcc ttacgcatct   5460 gtgcggtatt tcacaccgca tacaggtggc acttttcggg gaaatgtgcg cggaaccccct   5520 atttgtttat ttttctaaat acattcaaat atgtatccgc tcatgagaca ataaccctga   5580
taaatgcttc aataatagca cgtgctaaaa cttcattttt aatttaaaag gatctaggtg   5640
aagatccttt ttgataatct catgaccaaa atcccttaac gtgagttttc gttccactga   5700
```

| | |
|---|---|
| gcgtcagacc ccgtagaaaa gatcaaagga tcttcttgag atccttttt tctgcgcgta | 5760 |
| atctgctgct tgcaaacaaa aaaccaccg ctaccagcgg tggtttgttt gccggatcaa | 5820 |
| gagctaccaa ctcttttcc gaaggtaact ggcttcagca gagcgcagat accaaatact | 5880 |
| gttcttctag tgtagccgta gttaggccac cacttcaaga actctgtagc accgcctaca | 5940 |
| tacctcgctc tgctaatcct gttaccagtg gctgctgcca gtggcgataa gtcgtgtctt | 6000 |
| accgggttgg actcaagacg atagttaccg gataaggcgc agcggtcggg ctgaacgggg | 6060 |
| ggttcgtgca cacagcccag cttggagcga acgacctaca ccgaactgag atacctacag | 6120 |
| cgtgagctat gagaaagcgc cacgcttccc gaagggagaa aggcggacag gtatccggta | 6180 |
| agcggcaggg tcggaacagg agagcgcacg agggagcttc caggggaaa cgcctggtat | 6240 |
| ctttatagtc ctgtcgggtt tcgccacctc tgacttgagc gtcgattttt gtgatgctcg | 6300 |
| tcagggggc ggagcctatg gaaaaacgcc agcaacgcgg ccttttacg gttcctgggc | 6360 |
| ttttgctggc cttttgctca catgttctt | 6389 |

<210> SEQ ID NO 29
<211> LENGTH: 6383
<212> TYPE: DNA
<213> ORGANISM: Artificial Sequence
<220> FEATURE:
<223> OTHER INFORMATION: Synthetic

<400> SEQUENCE: 29

| | |
|---|---|
| gactcttcgc gatgtacggg ccagatatac gcgttgacat tgattattga ctagttatta | 60 |
| atagtaatca attacggggt cattagttca tagcccatat atggagttcc gcgttacata | 120 |
| acttacggta aatggcccgc ctggctgacc gcccaacgac ccccgcccat tgacgtcaat | 180 |
| aatgacgtat gttcccatag taacgccaat agggactttc cattgacgtc aatgggtgga | 240 |
| ctatttacgg taaactgccc acttggcagt acatcaagtg tatcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |
| aaaatgtcgt aacaactccg ccccattgac gcaaatgggc ggtaggcgtg tacggtggga | 600 |
| ggtctatata agcagagctc tctggctaac tagagaaccc actgcttact ggcttatcga | 660 |
| aattaatacg actcactata gggagaccca agctggctag cgtttaaact taagcttggt | 720 |
| accgagctcg gatccactag tccagtgtgg tggaattctg cagctcgcat ctctccttca | 780 |
| cgcgcccgcc gccctacctg aggccgccat ccacgccggt tgagtcgcgt tctgccgcct | 840 |
| cccgcctgtg gtgcctcctg aactgcgtcc gccgtctagg taagtttaaa gctcaggtcg | 900 |
| agaccgggcc tttgtccggc gctcccttgg agcctaccta gactcagccg gctctccacg | 960 |
| ctttgcctga cctgcttgc tcaactctag gtaagttaat gagacagata gaaactggtc | 1020 |
| ttgtagaaac agagtagtcg cctgcttttc tgccaggtgc tgacttctct cccctgggct | 1080 |
| ttttctttt tctcaggttg aaaagaagaa gacgaagaag acgaagaaga caaaccgtcg | 1140 |
| tcgactgcca tgcgccgctg attaacgccg ccaccatggc ccaccgacgc agatccagaa | 1200 |
| gctgccgtga ggaccagaag cccgtgatgg atgatcagag ggaccttatc tctaacaatg | 1260 |
| aacaactgcc aatgctcggc agacggcctg ggggcccgga gagcaagtgc agcagaggag | 1320 |
| ccttgtacac ggggttctcc attttagtga ctctccttct cgccggccaa gctaccaccg | 1380 |

```
cctactttct gtaccaacag caaggcagac tagacaaact gacaatcaca agccagaacc    1440
ttcagctgga gtctctgcgg atgaagctgc ccgctttgtg gatgagattg cttcctctac    1500
ttgctctcct ggcgctctgg ggacctgacc ccgagcaaga gtttgttaat cagcacctgt    1560
gtgggagtca tctggtggag gcactctatt tagtgtgcgg agagaggggc ttcttctaca    1620
ctccaaagac cagacgggag gccgaagacc ttcaagtggg gcaagtagaa ctgggtggcg    1680
gacccggtgc cgggagcctt cagccgctcg ccctggaggg ctctcttcag aaacgcggca    1740
tcgtggagca gtgttgcaca tccatttgct cactctacca gctggagaac tactgcaacg    1800
gaagcggagt gaagcagacg ttgaattttg atttgttgaa gttggcgggg gatgtggaga    1860
gcaatccggg gccgatgccc cctagtggcc tcagactttt gttattgtta ttaccgcttt    1920
tatggctctt ggtgctgaca ccgggccgtc cggctgctgg cttgtcgact tgtaagacaa    1980
ttgatatgga attggtgaaa cgaaaacgga ttgaggccat ccgaggacag attttgagca    2040
agctgcggct tgcctcgcca ccctcgcaag gggaagtccc accggacct ctaccagaag     2100 cagtcctagc gctgtacaac agtacaagag atagagtggc cggggaatcc gcagaaccag    2160
agcctgagcc tgaagccgat tattatgcaa aggaagtgac tagggtcctg atggtcgaga    2220
cccataacga aatctacgac aaattcaaac aaagtaccca ctctatctac atgttcttca    2280
acaccagtga gctaagagaa gccgtgcccg aacctgtgct tctttcccgc gcagaactcc    2340
gcctcttgag actcaaattg aaagttgaac aacacgtaga gctttaccag aaatactcta    2400
ataattcatg gcgatatctt tctaatcgtc tcctcgcccc atctgacagc cctgaatggc    2460
tctccttcga cgttacggga gttgtgcgcc agtggctcag cagaggcgga gagatagagg    2520
gctttcggct gagcgcacat agctctagcg actcaaggga caacacattg caagtggata    2580
ttaacggttt tacaactgga cggagagggg acctggcgac catccacggc atgaatagac    2640
ctttcctgct gctgatggct actccctgg agagggcaca gcacttacag tcttccagac     2700
accggcgcgc cctggataca aactactgct tcagctccac cgaaaagaac tgttgcgtgc    2760
ggcagctgta cattgacttc agaaaggatc tgggctggaa gtggattcat gagcccaagg    2820
ggtatcatgc caacttctgt cttgggccat gcccatacat ctggtcactg gatacccagt    2880
actccaaagt tctggccttg tacaatcaac acaaccctgg agcttccgcc gctccttgct    2940
gtgtgcccca agcccctaggag cccctgccca tcgtttatta tgtcgacgc aagcccaaag    3000 tagaacagct atcaaatatg atcgtgagaa gctgcaagtg tagctgataa acgcgtcgag    3060
catgcatcta gggcggccaa ttccgcccct ctccccccca ccctctccc tcccccccc     3120 ctaacgttac tggccgaagc cgcttggaat aaggccggtg tgcgtttgtc tatatgttat    3180
tttccaccat attgccgtct tttggcaatg tgagggcccg gaaacctggc cctgtcttct    3240
tgacgagcat tcctaggggt cttttcccctc tcgccaaagg aatgcaaggt ctgttgaatg    3300
tcgtgaagga agcagttcct ctggaagctt cttgaagaca acaacgtct gtagcgaccc     3360 tttgtagaca gcggaacccc ccacctggcg atagatgcct ctgcggccaa aagccacgtg    3420
tataagatac acctgcaaag gcggcacaac cccagtgcca cgttgtgagt tggatagttg    3480
tggaaagagt caaatggctc tcctcaagcg tattcaacaa ggggctgaag gatgcccaga    3540
aggtacccca ttgtatggga tctgatctgg ggcctcggtg cacatgcttt acatgtgttt    3600
agtcgaggtt aaaaaacgtc taggcccccc gaaccacggg gacgtggttt tcctttgaaa    3660
aacacgatga taatatgatg cacagctcag cactgctctg ttgcctggtc ctcctgactg    3720
```

```
gggtgagggc cagcccaggc cagggcaccc agtctgagaa cagctgcacc cacttcccag    3780
gcaacctgcc taacatgctt cgagatctcc gagatgcctt cagcagagtg aagactttct    3840
ttcaaatgaa ggatcagctg gacaacttgt tgttaaagga gtccttgctg gaggacttta    3900
agggttacct gggttgccaa gccttgtctg agatgatcca gttttacctg gaggaggtga    3960
tgccccaagc tgagaaccaa gacccagaca tcaaggcgca tgtgaactcc ctgggggaga    4020
acctgaagac cctcaggctg aggctacggc gctgtcatcg atttcttccc tgtgaaaaca    4080
agagcaaggc cgtggagcag gtgaagaatg cctttaataa gctccaagag aaaggcatct    4140
acaaagccat gagtgagttt gacatcttca tcaactacat agaagcctac atgacaatga    4200
agatacgaaa cgggagcggc gctactaact tcagcctgct gaagcaggct ggagacgtgg    4260
aggagaaccc tggacctatg tacagaatgc agctgctgag ctgcatcgcc ctgagcctgg    4320
ccctggtgac caacagcgca cccacgtcct ctagcaccaa gaagacccag ttacagttgg    4380
agcatctact tttagacctg caaatgattt tgaacggcat caacaactac aagaatccta    4440
aacttactcg catgcttacc ttcaaatttt acatgcccaa gaaggccacc gaactgaagc    4500
acttgcaatg tctggaggaa gaactcaagc cgctggagga agttctcaac ctcgcgcagt    4560
ccaagaattt ccacctccgg ccaagagacc tgatcagtaa cattaatgtg atagtgctgg    4620
agctgaaggg aagcgagact acatttatgt gcgagtacgc cgatgaaacc gctacaatcg    4680
tcgagttcct gaatagatgg atcacatttt gccagtcaat tatctctact ctgacatgat    4740
aactcgagtc tagagggccc gtttaaaccc gctgatcagc ctcgactgtg ccttctagtt    4800
gccagccatc tgttgtttgc ccctcccccg tgccttcctt gaccctggaa ggtgccactc    4860
ccactgtcct ttcctaataa aatgaggaaa ttgcatcgca ttgtctgagt aggtgtcatt    4920
ctattctggg gggtggggtg gggcaggaca gcaaggggga ggattgggaa gacaatagca    4980
ggcatgctgg ggatgcggtg ggctctatgg cttctactgg gcggttttat ggacagcaag    5040
cgaaccggaa ttgccagctg gggcgccctc tggtaaggtt gggaagccct gcaaagtaaa    5100
ctggatggct ttctcgccgc caaggatctg atggcgcagg gatcaagct ctgatcaaga    5160 gacaggatga ggatcgtttc gcatggccaa agaagacaat attgaaatgc aaggtaccgt    5220
tcttgaaacg ttgcctaata ccatgttccg cgtagagtta gaaaacggtc acgtggttac    5280
tgcacacatc tccggtaaaa tgcgcaaaaa ctacatccgc atcctgacgg gcgacaaagt    5340
gactgttgaa ctgaccccgt acgacctgag caaaggccgc attgtcttcc gtagtcgctg    5400
ataaattatt aacgcttaca atttcctgat gcggtatttt ctccttacgc atctgtgcgg    5460
tatttcacac cgcatacagg tggcactttt cggggaaatg tgcgcggaac ccctatttgt    5520
ttatttttct aaatacattc aaatatgtat ccgctcatga caataaccct gataaatg     5580 cttcaataat agcacgtgct aaaacttcat ttttaattta aaaggatcta ggtgaagatc    5640 cttttgata atctcatgac caaaatccct aacgtgagt tttcgttcca ctgagcgtca    5700
gaccccgtag aaaagatcaa aggatcttct tgagatcctt ttttctgcg cgtaatctgc    5760 tgcttgcaaa caaaaaaacc accgctacca gcggtggttt gtttgccgga tcaagagcta    5820
ccaactcttt ttccgaaggt aactggcttc agcagagcgc agataccaaa tactgttctt    5880
ctagtgtagc cgtagttagg ccaccacttc aagaactctg tagcaccgcc tacatacctc    5940
gctctgctaa tcctgttacc agtggctgct gccagtggcg ataagtcgtg tcttaccggg    6000
ttggactcaa gacgatagtt accggataag gcgcagcggt cgggctgaac ggggggttcg    6060
tgcacacagc ccagcttgga gcgaacgacc tacaccgaac tgagatacct acagcgtgag    6120
```

```
ctatgagaaa gcgccacgct tcccgaaggg agaaaggcgg acaggtatcc ggtaagcggc    6180
agggtcggaa caggagagcg cacgaggag cttccagggg gaaacgcctg gtatctttat    6240
agtcctgtcg ggtttcgcca cctctgactt gagcgtcgat ttttgtgatg ctcgtcaggg    6300
gggcggagcc tatggaaaaa cgccagcaac gcggcctttt tacggttcct gggcttttgc    6360
tggccttttg ctcacatgtt ctt                                            6383

<210> SEQ ID NO 30
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = a bulky hydrophobic amino acid such as
      tryptophan or isoleucine

<400> SEQUENCE: 30

Tyr Xaa Xaa Xaa
1

<210> SEQ ID NO 31
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(5)
<223> OTHER INFORMATION: Xaa = any amino acid

<400> SEQUENCE: 31

Asp Glu Xaa Xaa Xaa Leu Leu Ile
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: Xaa = any amino acid

<400> SEQUENCE: 32

Asp Xaa Xaa Leu Leu
1               5

<210> SEQ ID NO 33
<211> LENGTH: 4
<212> TYPE: PRT
<213> ORGANISM: Artificial Sequence
<220> FEATURE:
<223> OTHER INFORMATION: Synthetic

<400> SEQUENCE: 33

Arg Ala Lys Arg
1
```

```
<210> SEQ ID NO 34
<211> LENGTH: 4
<212> TYPE: PRT
<213> ORGANISM: Artificial Sequence
<220> FEATURE:
<223> OTHER INFORMATION: Synthetic

<400> SEQUENCE: 34

Arg Arg Arg Arg
1

<210> SEQ ID NO 35
<211> LENGTH: 4
<212> TYPE: PRT
<213> ORGANISM: Artificial Sequence
<220> FEATURE:
<223> OTHER INFORMATION: Synthetic

<400> SEQUENCE: 35

Arg Lys Arg Arg
1

<210> SEQ ID NO 36
<211> LENGTH: 4
<212> TYPE: PRT
<213> ORGANISM: Artificial Sequence
<220> FEATURE:
<223> OTHER INFORMATION: Synthetic

<400> SEQUENCE: 36

Arg Arg Lys Arg
1
```